(12) United States Patent
Hamada et al.

(10) Patent No.: US 8,232,069 B2
(45) Date of Patent: Jul. 31, 2012

(54) ANTIBODY DIRECTED AGAINST PAP2A AND USE THEREOF FOR DIAGNOSTIC AND THERAPEUTIC PURPOSES

(75) Inventors: Hirofumi Hamada, Sapporo (JP); Kiminori Nakamura, Hokkaido (JP); Kazunori Kato, Hokkaido (JP)

(73) Assignee: Sapporo Medical University, Hokkaido (JP)

( * ) Notice: Subject to any disclaimer, the term of this patent is extended or adjusted under 35 U.S.C. 154(b) by 1220 days.

(21) Appl. No.: 11/914,618

(22) PCT Filed: May 17, 2006

(86) PCT No.: PCT/JP2006/310406
§ 371 (c)(1),
(2), (4) Date: Nov. 16, 2007

(87) PCT Pub. No.: WO2006/123829
PCT Pub. Date: Nov. 23, 2006

(65) Prior Publication Data
US 2009/0214421 A1 Aug. 27, 2009

(30) Foreign Application Priority Data

May 17, 2005 (JP) ................................. 2005-143801
Jul. 11, 2005 (JP) ................................. 2005-202069

(51) Int. Cl.
*G01N 33/574* (2006.01)
(52) U.S. Cl. ......... 435/7.23; 436/64; 436/501; 530/350; 530/387.7; 530/388.8; 530/389.7
(58) Field of Classification Search ............. 435/6, 7.23; 436/64, 501; 530/350, 387.7, 388.8, 389.7; 536/23.5
See application file for complete search history.

(56) References Cited

U.S. PATENT DOCUMENTS

2004/0002067 A1* 1/2004 Erlander et al. ................... 435/6
2004/0146921 A1* 7/2004 Eveleigh et al. ................... 435/6
2011/0015090 A1* 1/2011 Majeti et al. ....................... 506/9

FOREIGN PATENT DOCUMENTS

JP 2002-330789 A 11/2002
WO WO 98/46730 A1 10/1998

OTHER PUBLICATIONS

Porkka et al. (J Pathol. Jan. 2001; 193 (1): 73-9).*
Roberts et al. (Biochim. Biophys. Acta. Aug. 24, 2000; 1487 (1): 33-49).*
Roessler et al. (Mol. Cell. Prot. 2006; 5 (11): 2092-2101).*
Roessler et al. (Clin. Can. Res. 2005; 11 (18): 6550-6557).*
Zolg et al. (Mol. Cell. Prot. 2004; 3 (4): 345-354).*
Porkka et al. (J. Pathol. Jan. 2001; 193 (1): 73-9).*
Hamada, Hirofumi, "Targeted gene therapy for cancer: Strategies and perspectives," Dai 64 Kai Nihon Gan Gakkai Gakujutsu Sokai Kiji, Aug. 15, 2005, p. 413, M18, and English translation (3 pages).
Nakamura et al., "Targeted gene therapy of pancreas using anti-PAP2a antibody," Dai 64 Kai Nihon Gan Gakkai Gakujutsu Sokai Kiji, Aug. 15, 2005, p. 436, W-68, with English translation (3 pages).
Sciorra et al., "Sequential Actions of Phosopholipase D and Phosphatidic Acid Phosphohydrolase 2b Generate Diglyceride in Mammalian Cells," Molecular Biology of the Cell, Nov. 1999, 10:3863-3876.
Kai et al., "Identification and cDNA Cloning of 35-kDa Phosphaticid Acid Phosphatase (Type 2) Bound to Plasma Membranes," J. Biol. Chem., Aug. 2, 1996, 271(31):18931-18938.
Nakamura et al., "PAP2a-Targeted Selective Gene Therapy for Pancreatic, Prostate, and Lung Cancers," J. Gene Med., Mar. 2006, 8(3):370-408, Abstract 46, pp. 388-389 of Abstracts from the 11th Meeting of the Japan Society of Gene Therapy, Jul. 28-30, 2005.
Nanjundan et al., "Pulmonary lipid phosphate phosphohydrolase in plasma membrane signaling platforms," Biochem. J., Sep. 15, 2001, 358(Pt.3):637-646.
Roberts et al., "Role of phosphatidic acid phosphatase 2a in uptake of extracellular lipid phosphate mediators," Biochimica et Biophysica Acta, Aug. 24, 2000, 1487(1):33-49.
Smyth et al., "Lipid Phosphate Phosphatases Regulate Lysophosphatidic Acid Production and Signaling in Platelets," J. Biol. Chem., Oct. 31, 2003, 278(44):43214-43223.
Tanyi et al., "Role of Decreased Levels of Lipid Phosphate Phosphatase-1 in Accumulation of Lysophosphatidic Acid in Ovarian Cancer," Clinical Cancer Research, Sep. 1, 2003, 9(10):3534-3545.
Cascallo et al., "Ras-dependent Oncolysis with an Adenovirus VAI Mutant," Cancer Research, Sep. 1, 2003, 63:5544-5550.
Kai et al., "Cloning and Characterization of Two Human Isozymes of $Mg^{2+}$-independent Phosphatidic Acid Phosphatase," J. Biol. Chem., Sep. 26, 1997, 272(39):24572-24578.
Leung et al., "Molecular Cloning of Two Alternatively Spliced Forms of Human Phosphatidic Acid Phosphatase cDNAs that are Differentially Expressed in Normal and Tumor Cells," DNA and Cell Biology, 1998, 17(4):377-385.
Tseng et al., "Systemic tumor targeting and killing by Sindbis viral vectors," Nature Biotechnology, Jan. 2004, 22(1):70-77. Ulrix et al., "Identification of the Phosphatidic Acid Phosphatase Type 2a Isozyme as an Androgen-regulated Gene in the Human Prostatic Adenocarcinoma Cell Line LNCaP," J. Biol. Chem., Feb. 20, 1998, 273(8):4660-4665.
Hamada, Hirofumi, "Gene Therapy by Restriction Growth Adenovirus, Gene therapy using conditionally replication-competent adenoviruses (CRCA)," Sapporo Medical University Revie Argicle, uploaded Aug. 31, 2004, http://www.sapmed.ac.jp/~hhamada/pages5-1-040831.htm, 4 pages, with English translation, 6 pages.
Hamada, Hirofumi, "Development of gene therapy aimed at the tumor-specific targeting," Reports of Research on Specific Field Relating to Cancer Research (CD-ROM), 2004, 175-178, with English translation, 5 pages.
Porkka et al., "Detection of differentially expressed genes in prostate cancer by combining suppression subtractive hybridization and cDNA library array," Journal of Pathology, 2001, 193:73-79.

* cited by examiner

*Primary Examiner* — Stephen Rawlings
(74) *Attorney, Agent, or Firm* — Foley & Lardner LLP

(57) ABSTRACT

The present invention aims at developing a gene delivery system which has a high selectivity to a target cell and can introduce and express a gene with high efficiency, particularly developing such a system for use in a gene delivery therapy using a viral vector. The present invention provides a method for targeting a drug, which comprises the step of delivering a drug containing a therapeutic gene to a target site using an anti-PAP2a antibody.

5 Claims, 65 Drawing Sheets

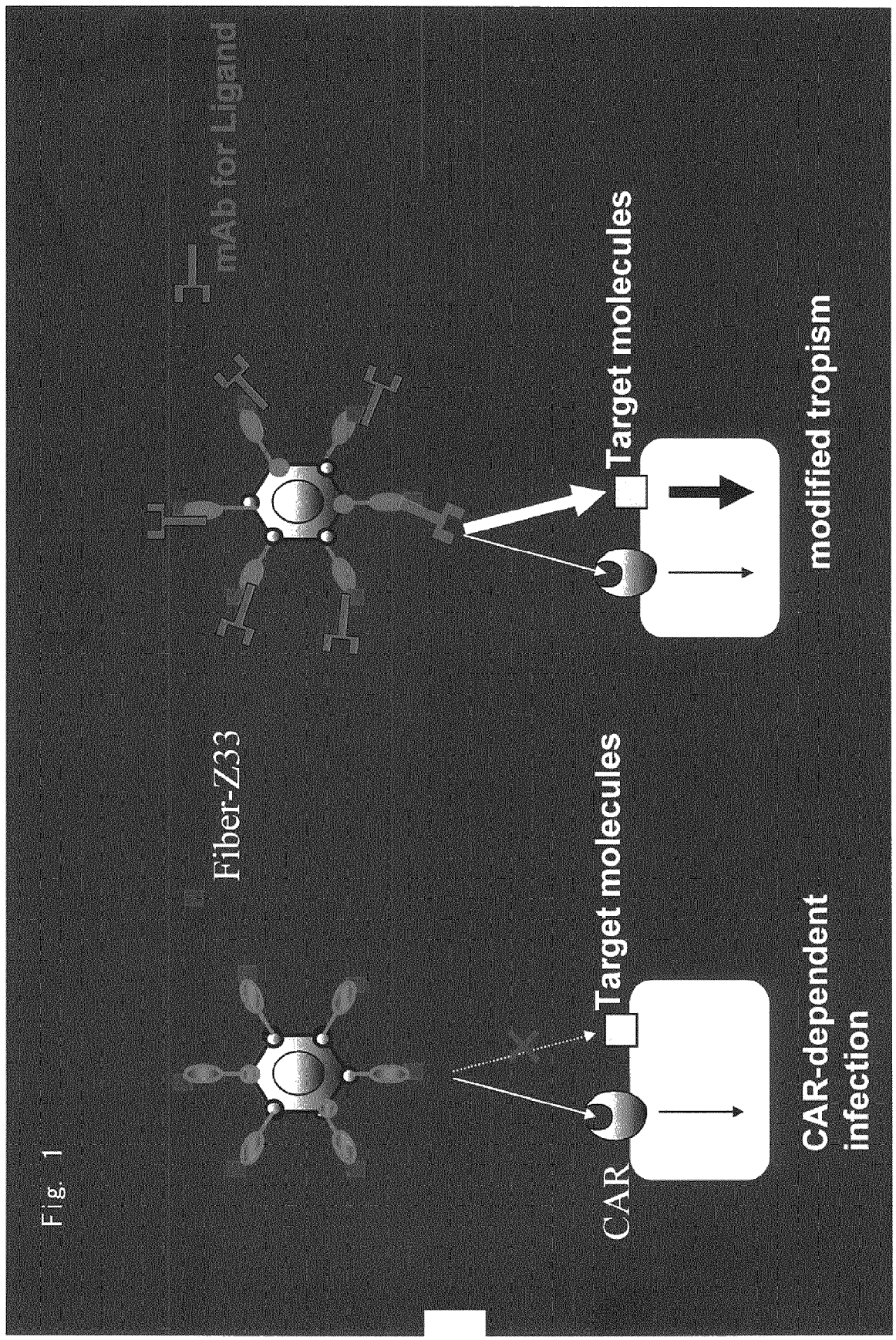

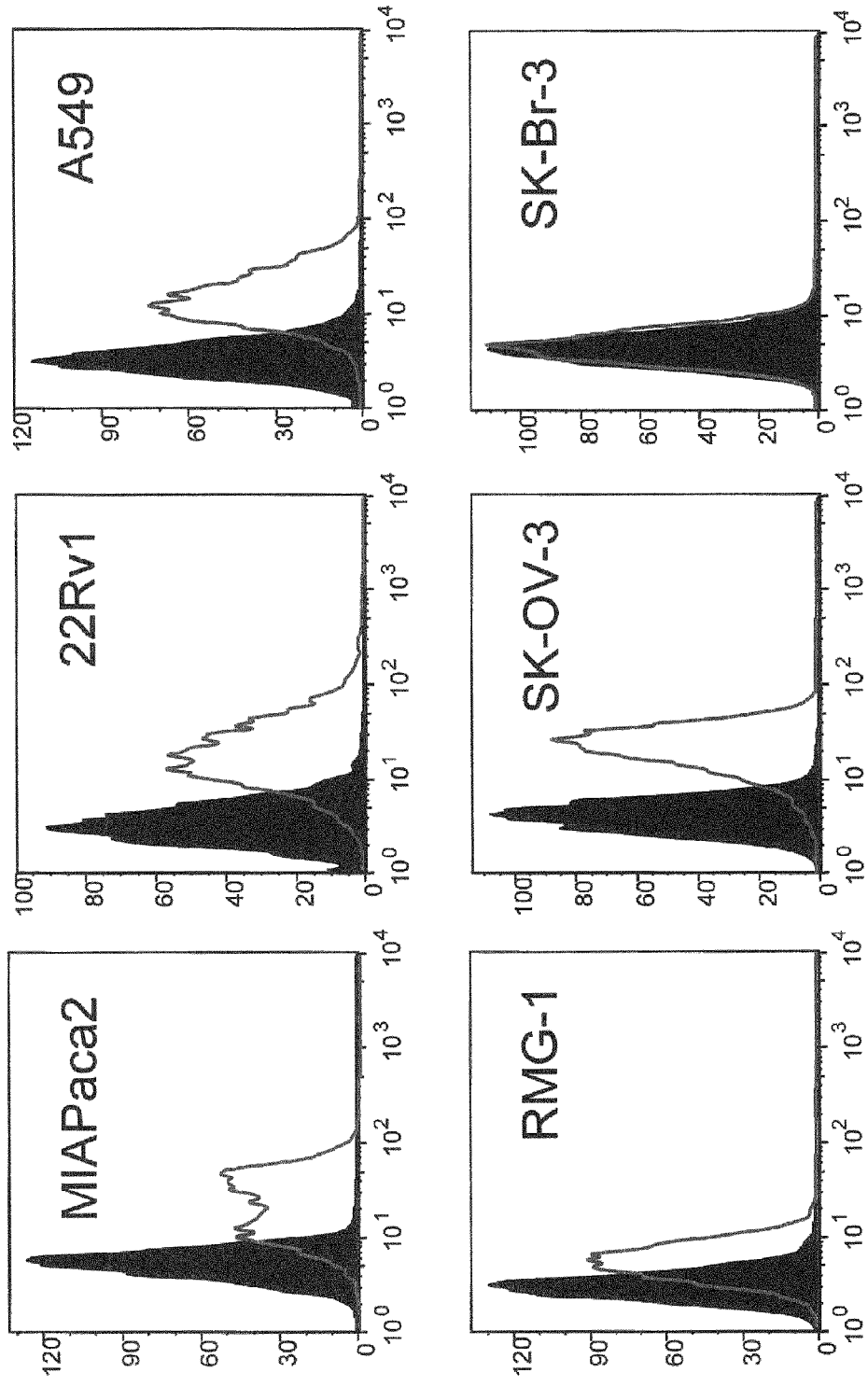
Fig. 3-3  S11 (anti-PAP2a)

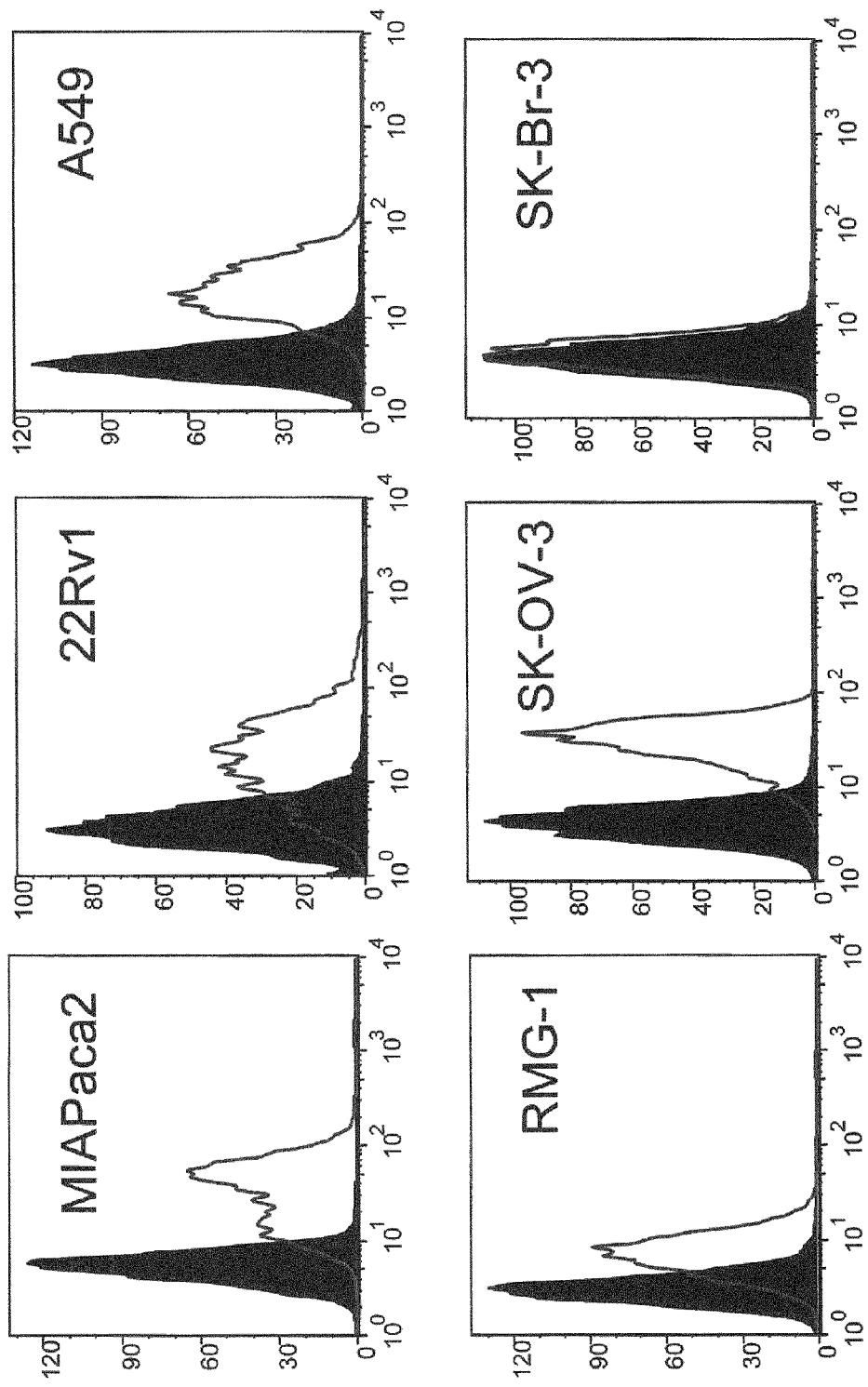
Fig. 3-4 T13 (anti-PAP2a)

Fig. 5

[S11-1]
gi|29171736    Mass: 32535

Phosphatidic acid phosphatase type 2A isoform 1 [Homo sapiens]

MFDKTRLPYV ALDVLCVLLA GLPFAILTSR HTPFQRGVFC NDESIKYPYK EDTIPYALLG

GIIIPFSIIV IILGETLSVY CNLLHSNSFI RNNYIATIYK AIGTFLFGAA ASQSLTDIAK

YSIGRLRPHF LDVCDPDWSK INCSDGYIEY YICRGNAERV KEGRLSFYSG HSSFSMYCML

FVALYLQARM KGDWARLLRP TLQFGLVAVS IYVGLSRVSD YKHHWSDVLT GLIQGALVAI

LVAVYVSDFF KERTSFKERK EEDSHTTLHE TPTTGNHYPS NHQP

The underlined sequences represent the hit peptide sequences.

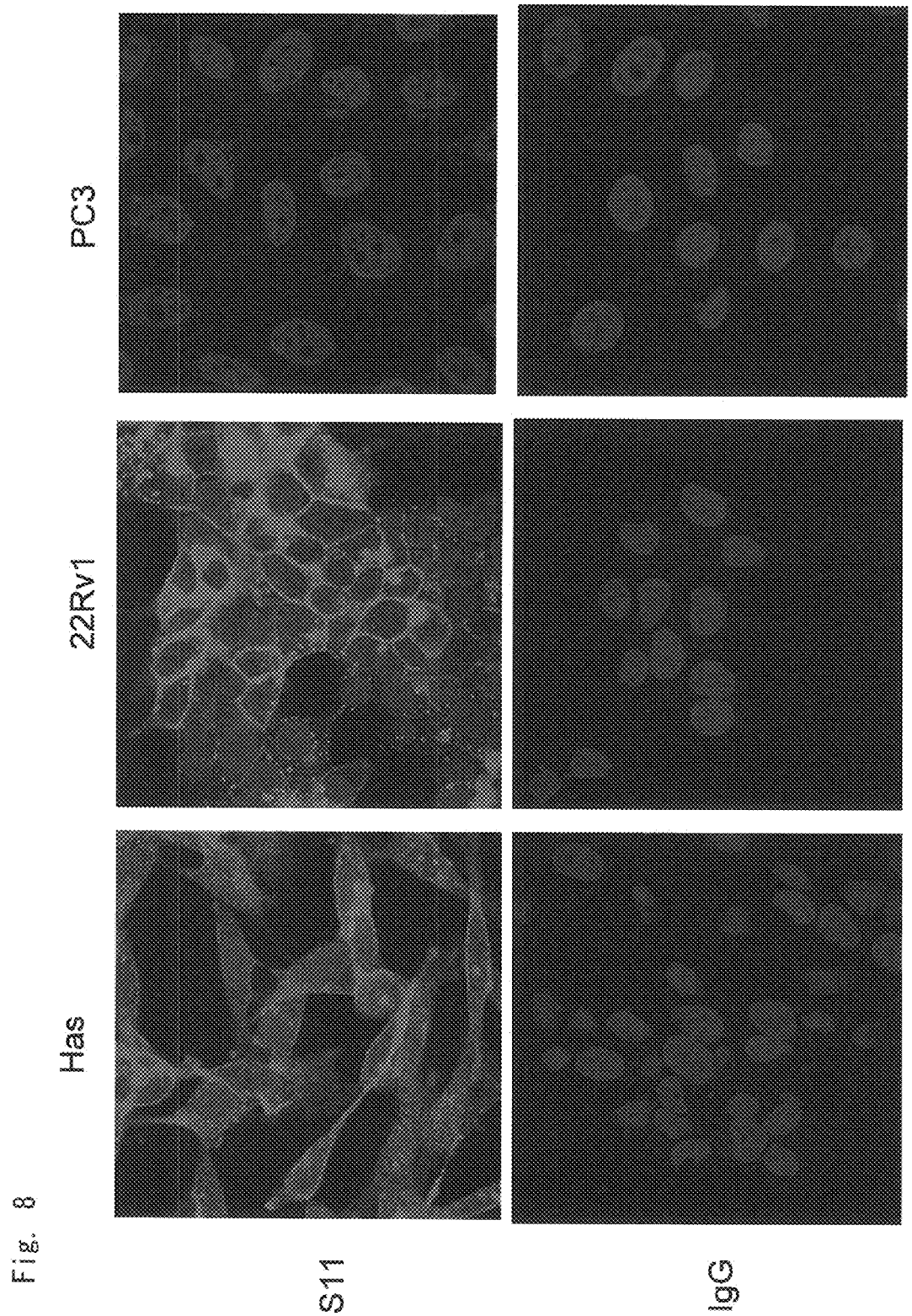

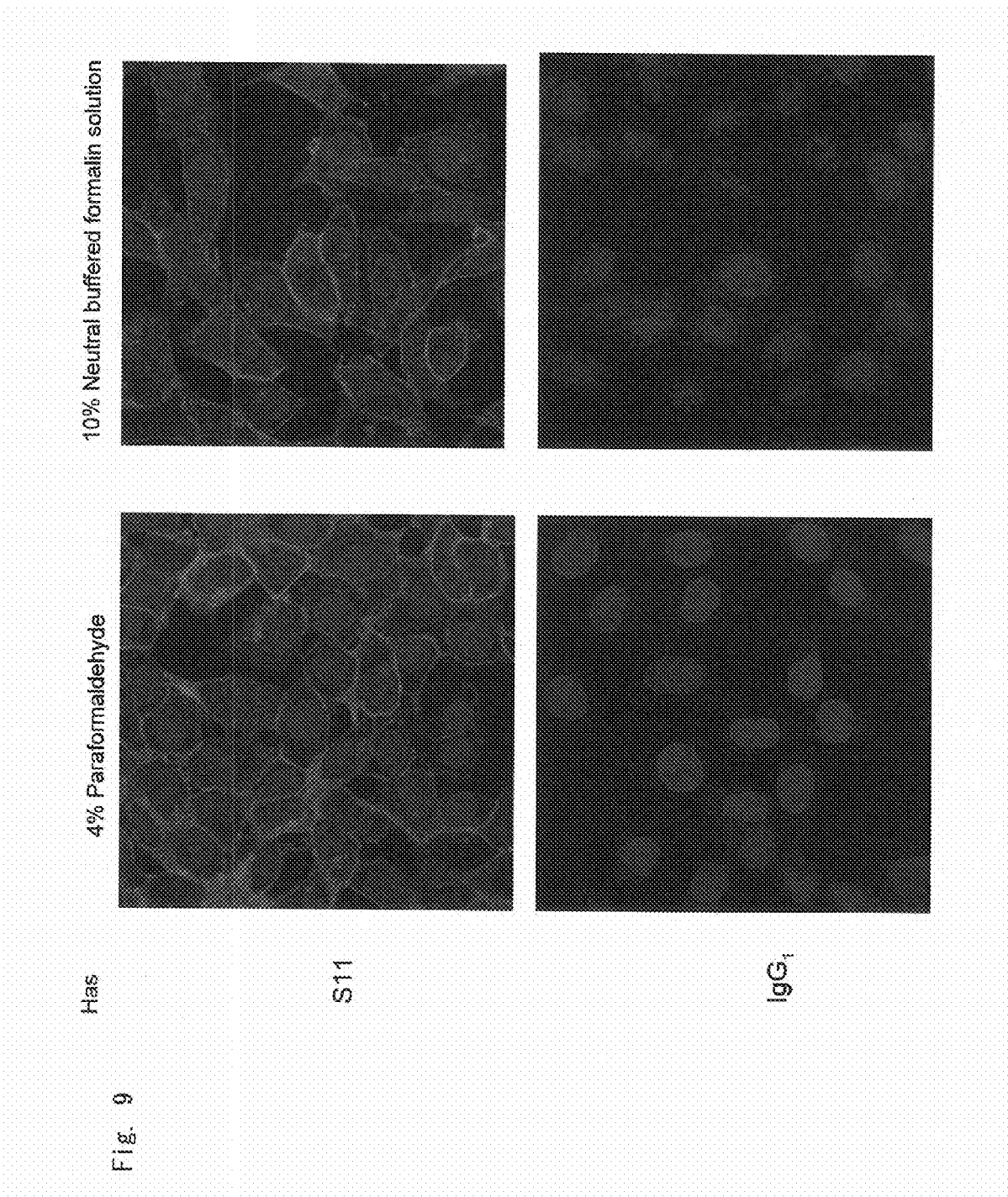

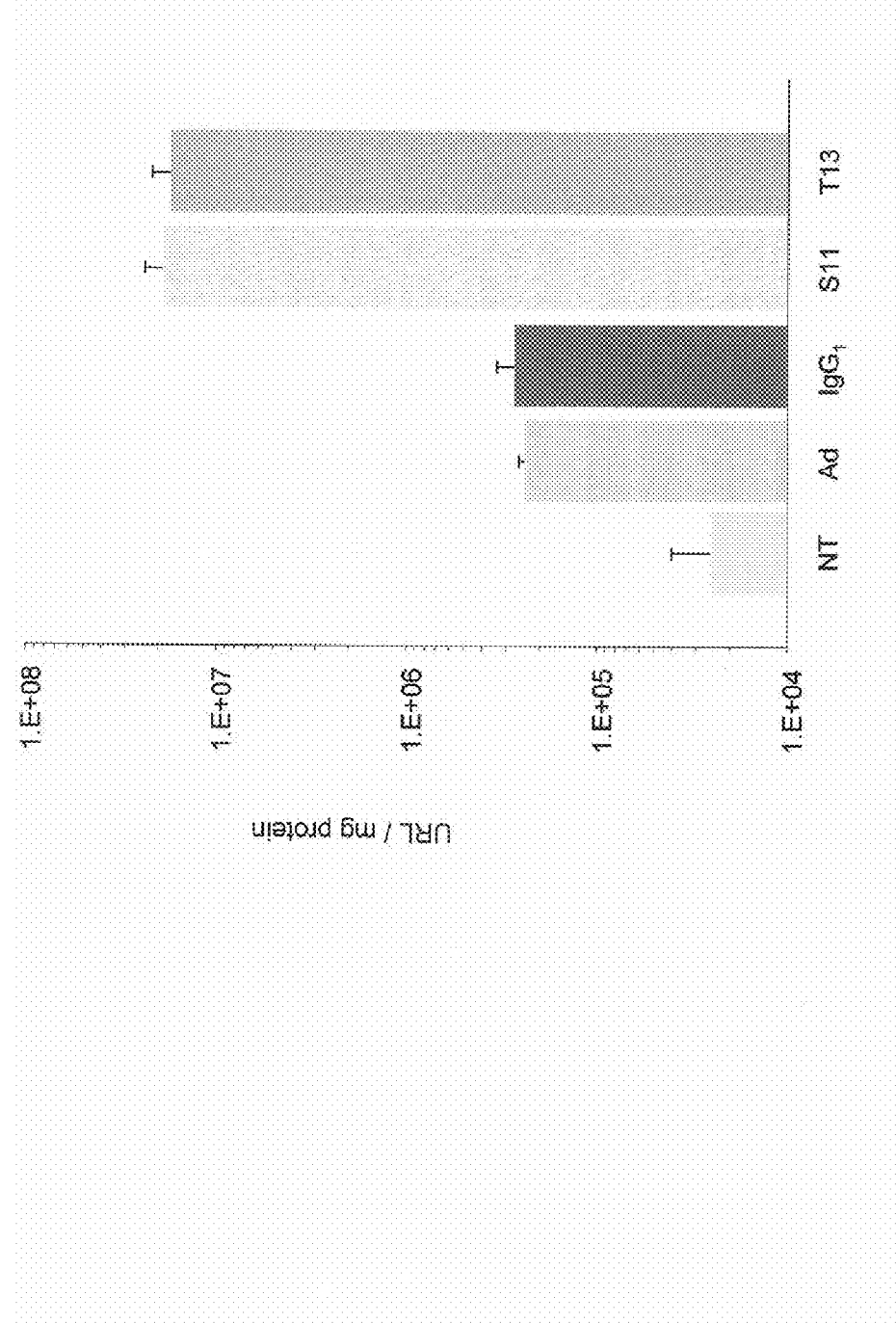
Fig. 10 Has

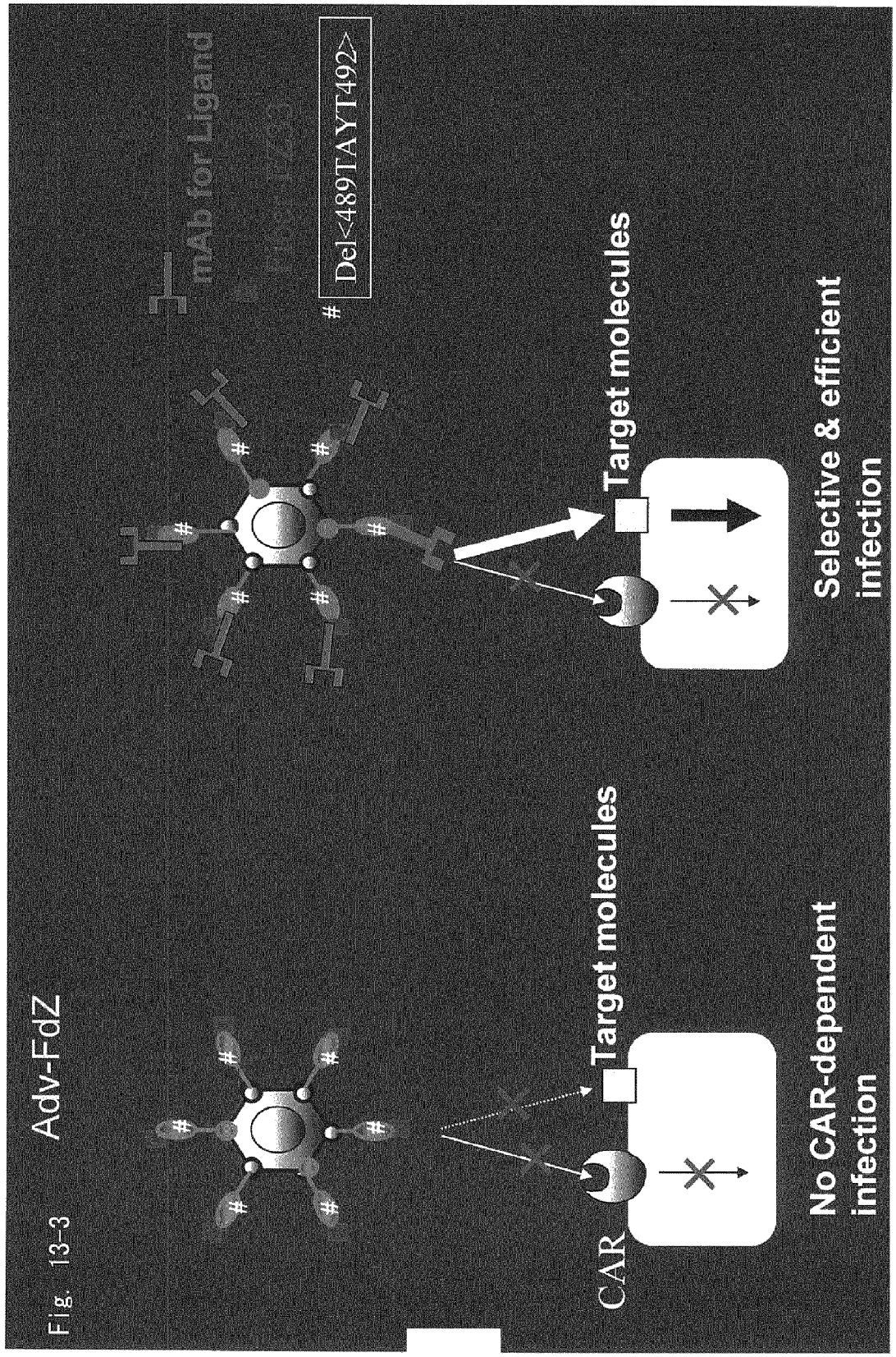

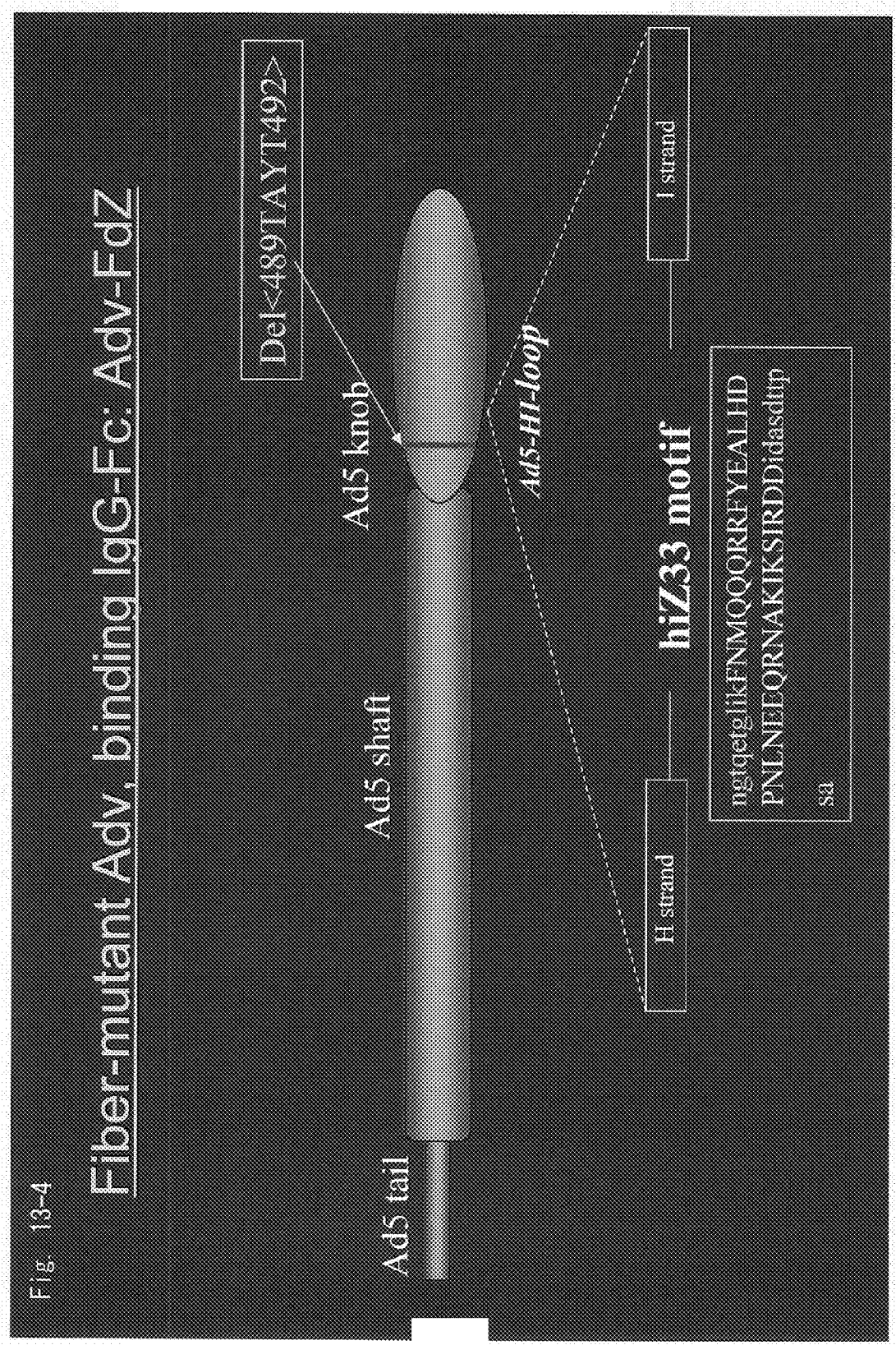

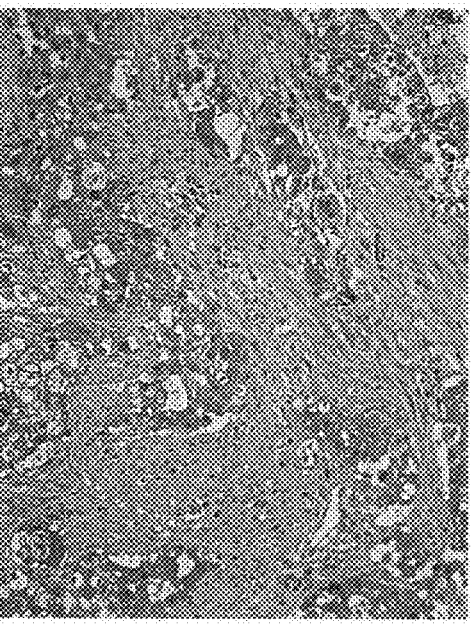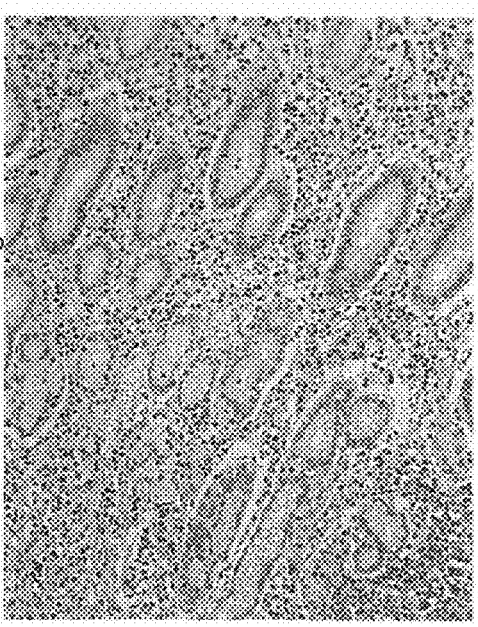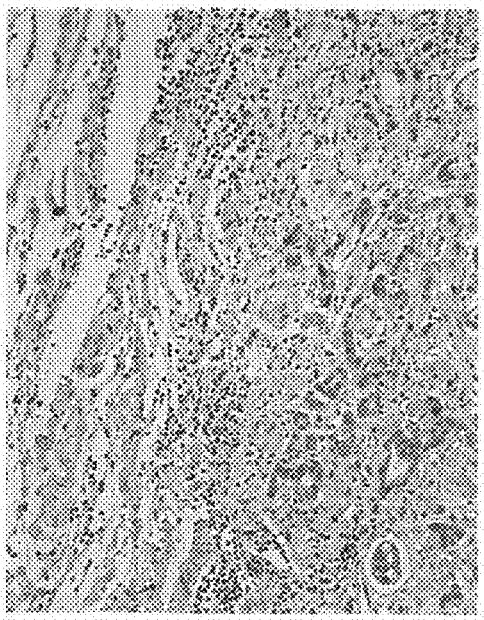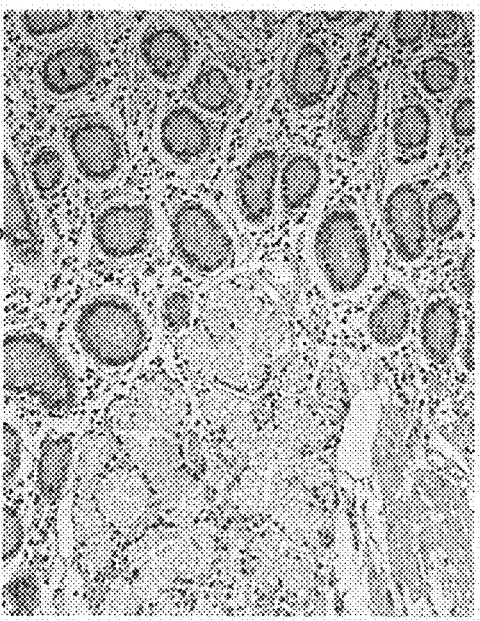
Fig. 14-1

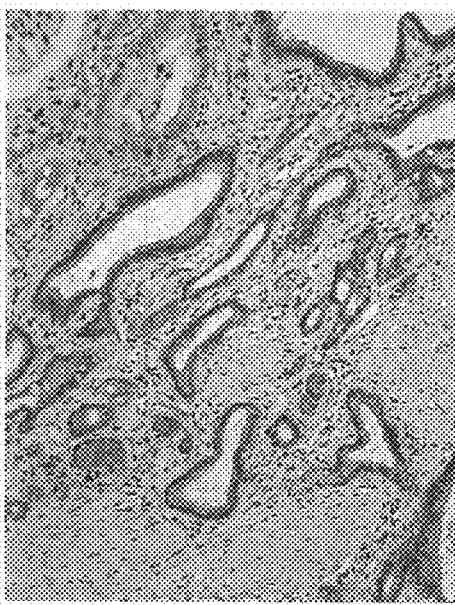
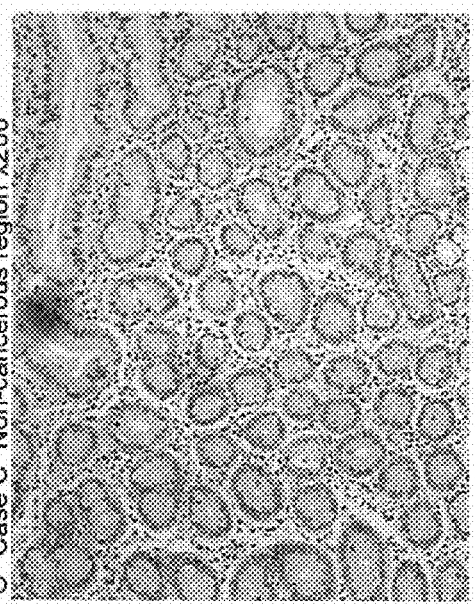
Fig. 14-2

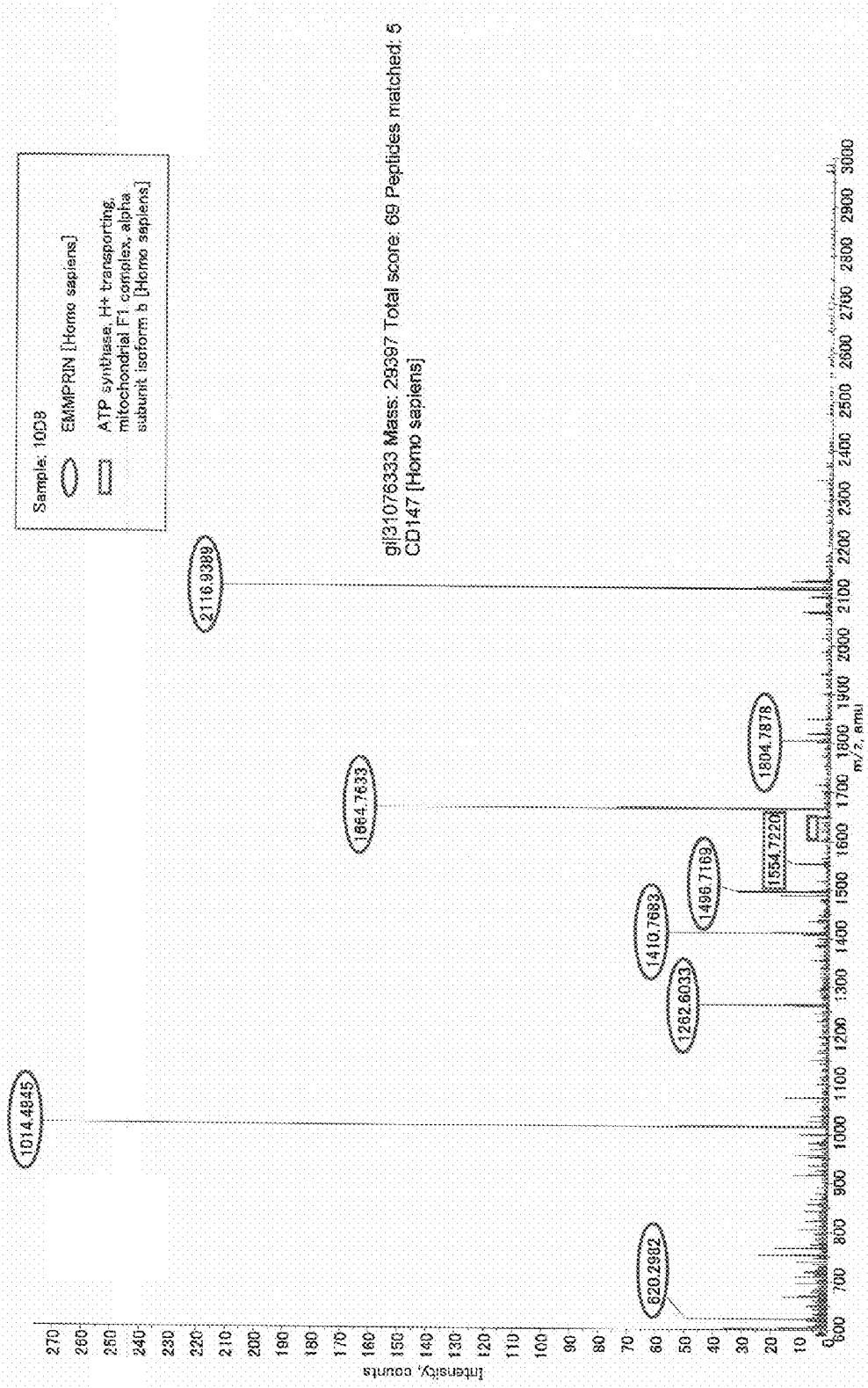

ANTIBODY DIRECTED AGAINST PAP2A AND USE THEREOF FOR DIAGNOSTIC AND THERAPEUTIC PURPOSES

CROSS-REFERENCE TO RELATED APPLICATIONS

This application is a National Stage application of PCT/JP2006/310406, filed May 17, 2006, which claims priority from Japanese application JP 2005-143801, filed May 17, 2005, and Japanese application JP 2005-202069, filed Jul. 11, 2005.

TECHNICAL FIELD

The present invention relates to antibodies against PAP2a and use thereof for diagnostic and therapeutic purposes. In particular, the present invention relates to production of monoclonal antibodies binding specifically to PAP2a, which are overexpressed in cancer tissues, including prostate cancer, pancreatic cancer, thyroid cancer, lung cancer, ovarian cancer, breast cancer, etc., as well as their use for diagnostic and therapeutic purposes.

BACKGROUND ART

So far the gene therapy for cancer has been generally achieved through intratumoral injection of therapeutic vectors. However, such topical administration is not effective for patients with metastatic tumor and recent development is directed to vectors which can specifically target metastatic tumor and makes systemic administration possible.

Sindbis viral vectors which can specifically infect metastasized tumor cells in BHK hamsters and mice to induce apoptosis (Tseng, J. C., Nature Biotechnol., 22:70-77, 2004), adenovirus VAI mutants showing cytotoxicity specifically to pancreatic cancer with ras gene mutation (Cascallo M. et al., Cancer Res., 63:5544-5550, 2003) and the like have already been reported.

Adenovirus is an icosahedron shape virus having double-stranded DNA in the genome and is classified into several categories serologically. Human adenovirus type 2 (Ad2) and human adenovirus type 5 (Ad5) are generally used for human gene therapy (e.g., JPA 2002-330789). Viral nucleic acid in adenovirus is surrounded by the protein coat called capsid. On the capsid surface, there are present 12 fibers with the tail and shaft on each vertex of its icosahedral structure and the knob at the terminus. These fibers are required for adenovirus to infect cells, and adenovirus binds to a cell surface receptor via these fibers. As such cell surface receptors, coxsackie adenovirus receptor (CAR) is known. Actually it is considered that most adenoviruses utilize CAR to adhere to cells.

Adenovirus can infect many cell-types that express CAR including normal cells and has been highly ranked for its use value as a vector. In contrast, the problem is pointed out that adenovirus infects not only targeted cells (e.g., tumor cells) but also surrounding normal cells when gene transfer is performed using an adenoviral vector. On the other hand, another problem arises that CAR is poorly expressed in pancreatic cancer cells, melanomas, etc. and adenovirus hardly infect them.

Therefore, the present inventors aimed to develop a gene transfer system by cancer-targeted viral vectors, which have high selectivity to targeted cells such as pancreatic cancer cells, etc. and can transfer and express a gene with high efficiency. To date the present inventors have prepared adenoviruses that express a reporter gene such as lacZ, EGFP, etc. using a FZ33 fiber-modified Ad5 virus, which carries a Z33 motif of protein A binding to the Fc domain of antibody in the HI loop of knob. Antibodies against membrane protein molecules CD40, CD20, or the like, which are highly expressed in leukemia cells lacking CAR expression, were previously attached to leukemia cells, recombinant adenovirus Ax3CAZ3-FZ33 expressing β-galactosidase was infected to the leukemia cells, and a gene transfer efficiency was assayed in terms of β-gal reporter gene expression as a marker. As a result, the inventors have discovered that gene expression is enhanced several fold for some of the antibodies used, as compared to control. However, targeted candidate molecules which can achieve selective and effective gene transfer to other tumor cells such as pancreatic cancer cells are not yet found.

Phosphatidic acid phosphatase (PAP) is an enzyme which catalyzes the conversion of phosphatidic acid (PA) to diacylglycerol (DG). PAP2a is an isozyme of phosphatidic acid phosphatase, was first identified in porcine and mouse (Kai et al., J. Biol. Chem., 1996, 271(31), 18931-18938), and then identified also in human (Kai et al, J. Biol. Chem., 1997, 272, 24572-24578).

It is reported that PAP2a is expressed in human normal tissues (especially, prostate gland) and prostate cancer (Leung, D. W., et al., DNA Cell Biol., 1998(4):377-85; Ulrix et al., J. Biol. Chem., 1998, 273(8):4660-4665), and Leung et al. suggested that PAP2a is down-regulated by tumorigenesis in many tissues. The invention disclosed in PCT application (WO 98/46730) by Leung et al. is also based on the finding that PAP2a is a cancer suppressor gene. According to Ultix et al., the expression in human tissues is ubiquitous but the highest level of expression was demonstrated in the prostate gland (Ultix et al., supra). It is reported that PAP2a expression in the prostate cancer culture cell line by Ultix et al. is androgen-regulated (Ultix et al., supra). However, biological importance of this protein (for example, why the protein is localized on the membrane surface, what role the protein plays in the prostate gland or prostate cancer cell line, etc.) still remains to be elucidated.

DISCLOSURE OF THE INVENTION

Under the circumstances described above, it has been desired to further develop a gene transfer system enabling the gene transfer and expression using viral vectors with high selectivity to various targeted cells and high efficiency and establish a methodology for such development.

When adenovirus carrying the FZ33 motif binding to the Fc domain of antibody was infected to pancreatic cancer cells and other various cancer cells, the present inventors used a monoclonal antibody prepared by immunizing mice with hamster Has cells, and performed screening of the monoclonal antibody, which can enhance the gene transfer efficiency by combination use when infected, using the reporter gene expression assay. As a result, the inventors could identify the monoclonal antibody-producing hybridomas, which can selectively enhance the multiplicity of infection of adenovirus.

Furthermore, the present inventors have identified an antigen specifically recognized by the monoclonal antibody, by means of mass spectrometry and homology search. As a result, the inventors have found that the antigen recognized by the above monoclonal antibody is PAP2a, and have come to accomplish the present invention.

That is, the present invention provides the following PAP2a antibody, and hybridomas producing the antibody.

(1) An antibody against PAP2a.

(2) The antibody according to (1) above, which is a monoclonal antibody.

(3) The antibody according to (2) above, which is a monoclonal antibody produced by the hybridoma deposited as Accession Number FERM P-20499 or FERM P-20498 to National Institute of Advanced Industrial Science and Technology, Patent Organisms Depository.

(4) A hybridoma producing the antibody according to (2) above.

(5) The hybridoma according to (4) above, which is the hybridoma deposited as Accession Number FERM P-20499 or FERM P-20498 to National Institute of Advanced Industrial Science and Technology, Patent Organisms Depository.

The present invention provides diagnostic agents comprising anti-PAP2a antibody described below.

(6) A diagnostic agent for cancer comprising an anti-PAP2a antibody.

(7) The diagnostic agent for cancer according to (6) above, wherein said anti-PAP2a antibody is an anti-PAP2a antibody produced by the hybridoma deposited as Accession Number FERM P-20499 or FERM P-20498 to National Institute of Advanced Industrial Science and Technology, Patent Organisms Depository.

(8) The diagnostic agent for cancer according to (6) or (7) above, wherein said anti-PAP2a antibody is labeled.

(9) The diagnostic agent for cancer according to (8) above, wherein the said anti-PAP2a antibody is labeled with radioisotopes, fluorogenic substrates, luminescent substrates, free radical substrates, particles, bacteriophages, cells, metals, enzymes or coenzymes.

(10a) The diagnostic agent for cancer according to any one of (6) to (9) above, wherein said cancer is a PAP2a-positive cancer (characterized by highly expressing PAP2a).

(10b) The diagnostic agent for cancer according to (10a) above, wherein said cancer is adenocarcinoma.

(10c) The diagnostic agent for cancer according to (10a) or (10b) above, wherein said cancer is pancreatic cancer, prostate cancer, thyroid cancer, lung cancer, ovarian cancer or breast cancer.

The present invention further provides the method for diagnosing cancer described below.

(11) A method for diagnosing cancer, which comprises the step of detecting and/or quantifying a PAP2a protein, its fragment, or a nucleic acid encoding the same, in a biological sample derived from a subject, as a diagnostic marker.

(12) The method according to (11) above, which comprises immunologically detecting and/or quantifying a PAP2a protein or its fragment in a biological sample derived from a subject using an anti-PAP2a antibody.

(13) The method according to (12) above, which comprises:

the step of contacting said biological sample with the anti-PAP2a antibody, and, the step of detecting and/or quantifying the binding of PAP2a in said biological sample with said anti-PAP2a antibody.

(14) The method according to (13) above, wherein said step of detection and/or quantification comprises the step of detecting and/or quantifying the binding of PAP2a with an anti-PAP2a antibody using a labeled anti-PAP2a antibody.

(15) The method according to any one of (11) to (14) above, wherein said biological sample is a tissue, cell, blood, urine, lymph fluid, spermatic fluid, saliva or sweat, derived from a subject.

(16) The method according to any one of (12) to (15) above, which follows an immunoassay selected from the group consisting of western blot assay, radioimmunoassay (RIA), enzyme-linked immunosorbent assay (ELISA), sandwich immunoassay, fluorescence immunoassay (FIA), time-resolved fluorescence immunoassay (TRFIA), enzyme-linked immunoassay (EIA), luminescence immunoassay (LIA), electrochemiluminescence immunoassay (ECLIA), latex agglutination assay, immunoprecipitation assay, precipitation reaction assay, gel-diffusion precipitation reaction assay, immunodiffusion assay, agglutination assay, complement fixation assay, immunoradiometric assay, fluoroimmunoassay and protein A immunoassay.

(17) The method according to any one of any one of (11) to (16) above, wherein said anti-PAP2a antibody is an anti-PAP2a antibody produced by the hybridoma deposited as Accession Number FERM P-20499 or FERM P-20498 to National Institute of Advanced Industrial Science and Technology, Patent Organisms Depository.

(18a) The method according to any one of (11) to (17) above, wherein said cancer is a PAP2a-positive cancer.

(18b) The method according to (18a) above, wherein said cancer is adenocarcinoma.

(18c) The method according to (18a) or (18b) above, wherein said cancer is pancreatic cancer, prostate cancer, thyroid cancer, lung cancer, ovarian cancer or breast cancer.

The present invention also provides method for detection and/or quantification described below.

(19) A method for immunologically detecting and/or quantifying cells expressing PAP2a on cell surfaces.

The present invention further provides agent for treating cancer comprising anti-PAP2a antibody described below.

(20) An agent for treating cancer comprising an anti-PAP2a antibody.

(21) The agent for treating cancer according to (20) above, wherein said anti-PAP2a antibody is an anti-PAP2a antibody produced by the hybridoma deposited to National Institute of Advanced Industrial Science and Technology, Patent Organisms Depository as Accession Number FERM P-20499 or FERM P-20498.

(22) The agent for treating cancer according to (21) above, wherein said anti-PAP2a antibody is a functional fragment of the anti-PAP2a antibody produced by the hybridoma deposited to National Institute of Advanced Industrial Science and Technology, Patent Organisms Depository as Accession Number FERM P-20499 or FERM P-20498.

(23) An agent for treating cancer according to any one of (20) to (22) above, wherein said anti-PAP2a antibody is bound chemically or by genetic engineering to any one of a viral vector carrying a radioisotope, a therapeutic protein, a low molecular agent or a therapeutic gene and a non-viral vector carrying a drug, or an optional combination thereof.

(24) The agent for treating cancer according to (23) above, wherein said anti-PAP2a antibody is bound to a viral vector.

(25) The agent for treating cancer according to (24) above, wherein said viral vector is a FZ33 fiber variant adenovirus.

(26) The agent for treating cancer according to (23) above, wherein said non-viral vector is selected from the group consisting of liposome vector, polymerized liposome, lipid vesicle, dendrimer, polyethylene glycol aggregate, polylysine, dextran, polyhydroxybutyric acid, Sendai virus envelope vector, plasmid vector and plasmid DNA naked vector.

(27) The agent for treating cancer according to (26) above, wherein said liposome vector is a liposome selected from the group consisting of saturated phospholipid, unsaturated phospholipid, phosphatidylcholine (PC), phosphatidylserine (PS), phosphatidylglycerol (PG), phosphatidylethanolamine (PE), dimethyldioctadecylammonium bromide (DDAB), dioleoyl phosphatidylethanolamine (DOPE), dioleoyl phosphatidylglycerol (DOPG) and dioleoyl phosphatidylserine (DOPS), or a liposome consisting of any combination of at least two of said liposomes.

(28) The agent for treating cancer according to any one of (20) to (23) above, wherein said anti-PAP2a antibody lyses a PAP2a expressing cell or inhibits its growth via an immunological effector cell.

(29) The agent for treating cancer according to any one of (20) to (23) above, wherein said anti-PAP2a antibody opsonizes a PAP2a expressing cell.

(30a) The agent for treating cancer according to any one of (20) to (29) above, wherein said cancer is a PAP2a-positive cancer.

(30b) The diagnostic agent for cancer according to (30a) above, wherein said cancer is adenocarcinoma.

(30c) The agent for treating cancer according to (30a) or (30b) above, wherein said cancer is pancreatic cancer, prostate cancer, thyroid cancer, lung cancer, ovarian cancer or breast cancer.

The present invention also provides method for targeting described below using an anti-PAP2a antibody.

(31) A method for targeting a drug, which comprises delivering a drug to a target site using an anti-PAP2a antibody.

(32) The method according to (31) above, wherein said anti-PAP2a antibody is an anti-PAP2a antibody produced by the hybridoma deposited as Accession Number FERM P-20499 or FERM P-20498 to National Institute of Advanced Industrial Science and Technology, Patent Organisms Depository.

(33) The method according to (32) above, wherein said anti-PAP2a antibody is a functional fragment of a monoclonal antibody produced by the hybridoma deposited as Accession Number FERM P-20499 or FERM P-20498 to National Institute of Advanced Industrial Science and Technology, Patent Organisms Depository.

(34) The method according to any one of (31) to (33) above, wherein said agent binds to said anti-PAP2a antibody chemically or by genetic engineering.

(35) The method according to any one of (31) to (34) above, wherein said drug comprises a radioisotope, a therapeutic protein, a low molecular agent or a therapeutic gene.

(36) The method according to (35) above, wherein said therapeutic gene is carried by a viral vector.

(37) The method according to (36) above, wherein said viral vector is fiber variant adenovirus.

(38) The method according to any one of (31) to (37) above, wherein said target site is a cell, tissue or organ where PAP2a is expressed specifically.

(39) The method according to any one of (31) to (38) above, wherein said target site is a pancreatic cell, prostate cancer cell, thyroid cancer cell, lung cancer cell, ovarian cancer cell or breast cancer cell.

The present invention further provides the method described below using anti-PAP2a antibody.

(40) A method for opsonizing a PAP2a expressing cell, which comprises using an anti-PAP2a antibody.

(41) A method for lysing a PAP2a expressing cell or inhibiting its growth via an immunological effector cell, which comprises using an anti-PAP2a antibody.

The present invention still further provides the method for screening or preparing a monoclonal antibody against the tissue-specific antigen described below.

(42) A method for screening a monoclonal antibody against a tissue-specific antigen, which comprises:

the step of immunizing a mammal with a cell expressing said tissue-specific antigen or said antigen, and allowing to fuse a lymphocyte from said immunized mammal with a myeloma cell to create a library of hybridomas, and, the step of contacting a fiber variant adenovirus modified to bind to the antibody with said cell in the presence of a product derived from said hybridoma selected from said library to infect said fiber variant adenovirus to said cell, and assaying the multiplicity of infection of said fiber variant adenovirus to said cell.

(42a) A method for screening a monoclonal antibody against a desired antigen, which comprises:

the step of obtaining a monoclonal antibody against said antigen, and, the step of contacting a fiber variant adenovirus modified to bind to said antibody with a cell expressing said antigen in the presence of said monoclonal antibody to infect said fiber variant adenovirus to said cell, and assaying the multiplicity of infection of said fiber variant adenovirus to said cell.

(42b) The method according to (42a) above, wherein the cell expressing said antigen is a cell transfected with a vector expressing said antigen.

(43) The method according to (42) above, wherein infection of said fiber variant adenovirus to said cell in the presence of a product derived from said hybridoma selected from said library is performed by:

(A) contacting the product derived from said hybridoma selected from said library with said cell and then contacting a fiber variant adenovirus modified to bind to the antibody with said cell;

(B) previously reacting the product derived from said hybridoma selected from said library with a fiber variant adenovirus modified to bind to the antibody and then contacting with said cell; or, (C) simultaneously administering the product derived from said hybridoma selected from said library and a fiber variant adenovirus modified to bind to the antibody thereby to contact with said cell.

(43a) The method according to (42a) above, wherein infection of said fiber variant adenovirus to said cell in the presence of said monoclonal antibody is performed by:

(A) contacting the monoclonal antibody with said cell and then contacting a fiber variant adenovirus modified to bind to the antibody with said cell;

(B) previously reacting the monoclonal antibody with a fiber variant adenovirus modified to bind to the antibody and then contacting with said cell; or, (C) simultaneously administering the monoclonal antibody and a fiber variant adenovirus modified to bind to the antibody thereby to contact with said cell.

(44) The method according to (42) or (43) above, wherein the step of assaying said multiplicity of infection includes assaying said multiplicity of infection of said fiber variant adenovirus to said cell by the reporter gene expression assay, wherein said fiber variant adenovirus expresses a reporter gene for assaying said multiplicity of infection upon said infection.

(44a) The method according to (44) above, wherein the monoclonal antibody is selected to provide an expression level of said reporter gene by at least two times higher than that of a control antibody.

(44b) The method according to (44) above, wherein the monoclonal antibody is selected to provide an expression level of said reporter gene by at least ten times higher than that of a control antibody.

(44c) A monoclonal antibody produced by the method according to (44a) or (44b) above.

(44d) The antibody according to (44c) above, which is an anti-PAP2a antibody.

(45) The method according to any one of (42) to (44) above, wherein said fiber variant adenovirus is a FZ33 fiber variant adenovirus.

(46) The method according to (45) above, wherein the reporter gene described above is lacZ or EGFP.

(47) The method according to any one of (42) to (46) above, wherein the cells described above is tumor cells.

(47a) The method according to (47) above, wherein said tumor cell is an adenocarcinoma cell.

(47b) The method according to (47) or (47a) above, wherein said tumor cell is a pancreatic cancer cell, prostate cancer cell, thyroid cancer cell, lung cancer cell, ovarian cancer cell or breast cancer cell.

(47c) The method according to any one of (42) to (46) above, wherein said tissue-specific antigen is a tumor-specific antigen.

(47d) The method according to (47c) above, wherein said tumor-specific antigen is PAP2a.

(47e) The method according to (42a) or (42b) above, wherein said cell is a CHO cell.

(47f) The method according to (42a) or (42b) above, wherein said antigen is CEA, human CD44 or human CD147.

The present invention further provides the following method for diagnosing cancer using an autoantibody.

(48) A method which comprises using an autoantibody against PAP2a as a diagnostic marker.

(49) The method according to (48) above, which comprises the step of detecting and/or quantifying an anti-PAP2a autoantibody in a biological sample collected from a subject.

(50a) The method according to (48) or (49) above, wherein said cancer is a PAP2a-positive cancer.

(50b) The method according to (50a) above, wherein said cancer is adenocarcinoma.

(50c) The method according to (50a) or (50b) above, wherein said cancer is pancreatic cancer, prostate cancer, lung cancer, ovarian cancer or breast cancer.

The present invention further provides a DNA encoding the following anti-PAP2a antibody, a vector carrying said DNA, a transformant obtained by transfecting the vector to a host cell, a method of producing the anti-PAP2a antibody, and the anti-PAP2a antibody produced by the method.

(51) A DNA encoding an anti-PAP2a antibody.

(52) A DNA encoding the H-chain V-region (including CDR1 to 3) or L-chain V-region (including CDR1 to 3) of an anti-PAP2a antibody.

(53) A vector comprising the DNA according to (51) or (52) above.

(54) A transformant, which is obtained by introducing the vector according to (53) above to a host cell.

(55) A method for producing an anti-PAP2a antibody, which comprises:
the step of culturing the transformant according to (54) above in an appropriate medium, and the step of collecting the anti-PAP2a antibody from the medium.

(56) An anti-PAP2a antibody produced by the method according to (55) above.

(57) An anti-PAP2a antibody according to (56) above, comprising the H-chain V-region (including CDR1 to 3) or L-chain V-region (including CDR1 to 3).

The present invention also provides an anti-PAP2a antibody having the following features.

(58) An anti-PAP2a antibody capable of enhancing the gene transfer efficiency by a viral vector to a specific cell.

(59) A humanized anti-PAP2a antibody comprising the H-chain V-region and L-chain V-region of an anti-PAP2a antibody.

(60) The humanized anti-PAP2a antibody according to (59) above, which is a human chimeric antibody or human CDR grafted antibody.

(61) A derivative in which an anti-PAP2a antibody is bound to a radioisotope, a therapeutic protein, a low molecular agent chemically or by genetic engineering.

The anti-PAP2a antibody of the present invention is useful for the diagnosis and treatment of PAP2a-positive cancers (especially adenocarcinoma).

The anti-PAP2a antibody of the present invention is particularly useful for the diagnosis and treatment of PAP2a-positive cancers, including at least pancreatic cancer, lung cancer, prostate cancer, thyroid cancer, ovarian cancer and breast cancer.

By concomitant use of the anti-PAP2a antibody of the present invention and a recombinant adenoviral vector having the binding domain to the Fc domain of antibody, the gene therapy using the adenoviral vector can be targeted not only for primary tumor but also for metastatic tumor.

The method of the present invention for identifying the antibody against a tissue (e.g., cancer)-specific antigen is useful for systematic search of the combination of target molecule candidates in the drug target therapy and antibodies against the same.

BRIEF DESCRIPTION OF THE DRAWINGS

FIG. 1 is a schematic representation of the targeted gene delivery using the recombinant adenoviral vector, Adv-FZ33 adenovirus, which is used in the present invention as a representative example.

FIG. 3-1 shows the results of FACS analysis showing reactions of the S11 antibody with various cell lines.

FIG. 3-2 shows the results of FACS analysis showing reactions of the T13 antibody with various cell lines.

FIG. 3-3 shows the results of FACS analysis showing reactions of the S11 antibody with various cell lines.

FIG. 3-4 shows the results of FACS analysis showing reactions of the T13 antibody with various cell lines.

FIG. 4 shows electrophoretic photographs showing the results of immunoprecipitation and silver stain.

FIG. 5 shows the results of mass spectrometry of the antigens recognized by the S11 antibody. Figure discloses SEQ ID NO: 1.

FIG. 7-1 shows graphs showing the results that plasmids expressing PAP2a (LPP1), PAP2b (LPP3) and PAP2c (LPP2), respectively, were transfected and examined by flow cytometry to determine which isoform of PAP the S11 antibody reacted with.

FIG. 7-2 is graphs showing the results that plasmids expressing PAP2a (LPP1), PAP2b (LPP3) and PAP2c (LPP2), respectively, were transfected and examined by flow cytometry to determine which isoform of PAP the T13 antibody reacted with.

FIG. 8 shows photographs of immunohistochemical staining showing reaction of the S11 antibody with cultured cell lines.

FIG. 9 shows photographs of immunohistochemical staining showing the examination results of fixation techniques for immunostaining of the S11 antibody.

FIG. 10 is graphs showing the multiplicity of infection of Ax3CAEGFP-FZ33 on Has cells when Has cells were infected with Ax3CAEGFP-FZ33, as the results of chemiluminescent β-Gal reporter gene assay.

FIG. 11-1B is graphs showing the results of multiplicity of infection of adenoviral vectors against pancreatic cancer cell Miapaca2, when evaluated by flow cytometry using EGFP-expressing Ax3 CAEGFP-FZ33, as in FIG. 11-1A.

FIG. 11-1C is graphs obtained from flow cytometry runs, which demonstrate the multiplicity of infection of Ax3CAEGFP-FZ33 on human prostate cancer cell 22Rv1 by comparison between when the cells were pre-treated with S11 and when the cells were pre-treated with control mouse IgG1.

FIG. 11-1D is graphs showing the results obtained from flow cytometry runs by comparing the multiplicity of infection of Ax3CAEGFP-FZ33 on another human prostate cancer cell PC3, between when the cells were pre-treated with control mouse IgG1 and when the cells were pre-treated with S11.

FIG. 11-2A is graphs showing the results of effects of T13 on the multiplicity of infection of FZ33 adenovirus for Has cells, which multiplicity of infection was evaluated by flow cytometry at vector doses of 300 vp/cell and 1000 vp/cell, using EGFP-expressing Ax3CAEGFP-FZ33.

FIG. 11-2B is graphs showing the results of effects of T13 on the multiplicity of infection of FZ33 adenovirus for pancreatic cancer cell Miapaca2, which multiplicity of infection was evaluated by flow cytometry at vector doses of 300 vp/cell and 1000 vp/cell, using EGFP-expressing Ax3CAEGFP-FZ33.

FIGS. 13-1 is a schematic representation of the plasmid vector pAx3 for producing the recombinant adenovirus which is used in the present invention as a typical example. Figure discloses SEQ ID NOS 35 and 34, respectively, in order of appearance.

FIGS. 13-2 is a schematic representation of the plasmid vector pAx3-FZ33 for producing the recombinant adenovirus which is used in the present invention as a typical example. Figure discloses SEQ ID NOS 33-34, respectively, in order of appearance.

FIG. 13-3 is a schematic view of the recombinant adenovirus vector Adv-FdZ which is used in the present invention as a typical example.

FIGS. 13-4 is a schematic view of the fiber region of recombinant adenovirus vector Adv-FdZ which is used in the present invention as a typical example. Figure discloses SEQ ID NOS 37 and 33, respectively, in order of appearance.

FIGS. 13-5 is a schematic view of the plasmid vector pAx31-FdZ for producing the recombinant adenovirus which is used in the present invention as a typical example. Figure discloses SEQ ID NOS 37, 33 and 36, respectively, in order of appearance.

FIG. 14-1 is microscopic photographs showing immunohistochemical staining of surgical specimens from two human pancreatic cancer cases A and B by the S11 antibody. The photographs at the upper column are staining of the region containing pancreatic cancer tissue and the photographs at the lower column are staining of the non-cancerous region around the pancreatic cancer tissue on the same slide.

FIG. 14-2 is microscopic photographs showing immunohistochemical staining of surgical specimens from human pancreatic cancer case C by the S11 antibody. The photographs at the upper column are staining of the region containing pancreatic cancer tissue and the photographs at the lower column are staining of the non-cancerous region around the pancreatic cancer tissue on the same slide.

FIG. 44B shows the results of mass spectrometry in determining the antigen for the 10D8 antibody.

BEST MODE FOR CARRYING OUT THE INVENTION

Figure 2:
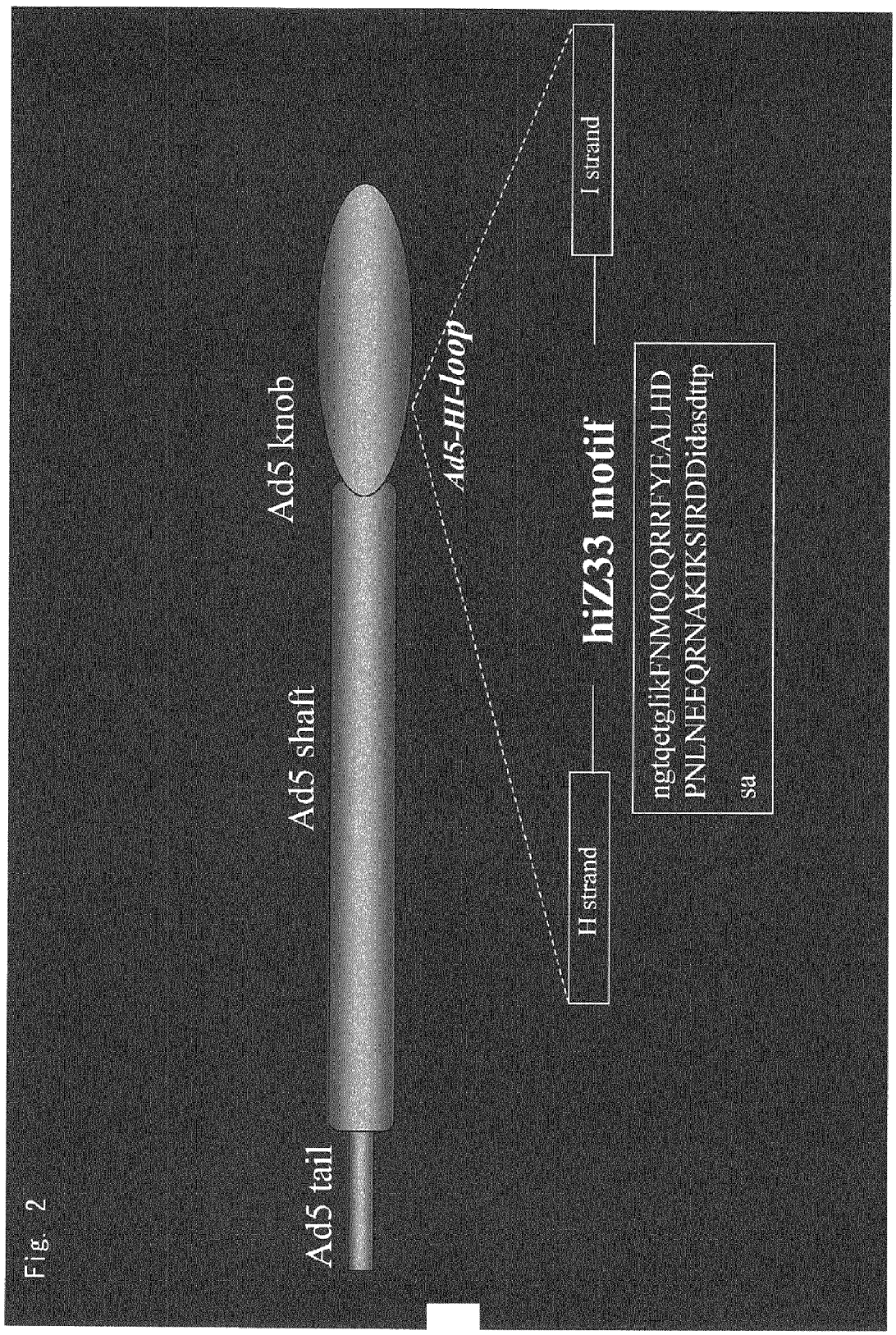
FIG. 2 is a schematic representation of the fiber region of recombinant adenoviral vector, Adv-FZ33 fiber-modified adenovirus, which is used in the present invention as a representative example. Figure discloses SEQ ID NO: 33.

According to the present invention, the monoclonal antibody enhancing the efficiency of gene transfer to target cells has been identified using a FZ33 fiber variant adenovirus. Further according to the present invention, it has been confirmed that the antigen for the monoclonal antibody is PAP2a.

The present inventors further evaluated the gene transfer to various cancer cells using the FZ33 fiber variant adenovirus in combination with the monoclonal antibody described above, and found that the gene transfer efficiency is markedly enhanced at least in pancreatic cancer cells and prostate cancer cells. Thus, the present invention provides the diagnosis of these cancers, which comprises using PAP2a as a maker, and/or the targeted therapy for these cancers targeting PAP2a.

By identification of the cancer-specific antigen and identification of the antibody capable of binding specifically to the antigen, a useful system for imaging and/or treatment of cancer is provided.

1. Anti-PAP2a Antibody

The present invention provides the antibody against PAP2a.

As used herein, "PAP2a (phosphatidic acid phosphatase type 2A isoform 1)," "PAP2a protein" or "PAP2a antigen" means the protein of 284 amino acid residues identified by the amino acid sequence (SEQ ID NO: 1) registered as accession number NP_003702 in the NCBI protein sequence database, and fragments of the protein, or derivatives thereof.

Herein, the term "derivatives" mean peptides or polypeptides containing mutation, substitution, deletion and/or addition of one or more (for example, several (e.g., six)) amino acid residues in the amino acid sequence of PAP2a protein or its fragments, and having substantially the same antigenicity as PAP2a protein. Herein, the term "substantially" means the degree of specificity which is specifically recognized by the anti-PAP2a antibody to the extent that can be used for the diagnosis and/or treatment of diseases characterized by PAP2a expression. Typical examples of the derivatives include sequence variability by PAP2a polymorphism, splicing, etc. Herein, the length of "fragment" is not limited as long as it is recognizable as an antigen binding specifically to the anti-PAP2a antibody, and the length is preferably at least 6 amino acids, more preferably at least 8 amino acids and most preferably at least 10 amino acids. These fragments may be any part of the PAP2a protein and preferably correspond to the epitope of PAP2a protein or contain the region corresponding to the epitope.

As used herein, the term "anti-PAP2a antibody" or "antibody against PAP2a" means an antibody binding specifically to PAP2a and includes a fragment of the antibody having substantially the same antigenic specificity as the original antibody (herein also called "a functional fragment") or derivatives thereof. The functional fragment of the antibody or its derivatives are intended to include functional fragments of the antibody such as Fab, Fab', F(ab')$_2$, single chain antibody (scFv), a disulfide stabilized V-region fragment (dsFv) or a CDR-containing peptide, or derivatives such as humanized antibody (e.g., CDR-grafted complete humanized antibody) and the like. The antibody used in the present invention can be produced by known methods as described below in detail, including immunization of animal followed by recovering sera (polyclonal) or spleen cells (for product hybridomas by fusion with appropriate cells).

As used herein, the antibody "binding specifically" to certain proteins or their fragments is intended to mean that the antibody binds to a particular amino acid sequence of these proteins or their fragments with substantially high affinity as compared to its affinity to other amino acid sequences. Herein, the term "substantially high affinity" means a high affinity to the extent that the particular amino acid sequence can be detected distinctly from the other amino acid sequences and typically refers to a binding affinity in terms of the binding constant (Ka) of at least $10^7$ M$^{-1}$, preferably at least $10^8$ M$^{-1}$, more preferably $10^9$ M$^{-1}$, much more preferably $10^{10}$ M$^{-1}$, $10^{11}$ M$^{-1}$, $10^{12}$ M$^{-1}$ or higher, e.g., up to $10^{13}$ M$^{-1}$ at the highest.

The anti-PAP2a antibody of the present invention can be a monoclonal antibody or a polyclonal antibody, preferably a monoclonal antibody. Preferred examples of the monoclonal antibody against PAP2a include monoclonal antibodies produced by the hybridomas deposited on Apr. 8, 2005 as Accession Nos. FERM P-20499 and FERM P-20498 to National Institute of Advanced Industrial Science and Technology, Patent Organisms Depository (Tsukuba Central 6, 1-1-1 Higashi, Tsukuba, Ibaraki, Japan).

Therefore, the present invention further provides the hybridomas which produce the monoclonal antibodies against PAP2a. More specifically, the present invention provides the hybridomas deposited on Apr. 8, 2005 as Accession Nos. FERM P-20499 and FERM P-20498 to National Institute of Advanced Industrial Science and Technology, Patent Organisms Depository.

Hereinafter, general methods for preparing monoclonal antibodies, polyclonal antibodies, antibody fragments, etc., which can be used to produce the anti-PAP2a antibody of the present invention, are described below.

Preparation of Monoclonal Antibody
Preparation of Monoclonal Antibody-Producing Cell The monoclonal antibody against PAP2a can be prepared as follows. PAP2a is administered to a mammal either solely or together with carriers or diluents to the site where antibody production is possible. In order to potentiate the antibody productivity upon the administration, complete Freund's adjuvants or incomplete Freund's adjuvants may be administered. The administration is usually carried out once in every two to six weeks and 2 to 10 times in total. Examples of the applicable mammals are monkeys, rabbits, dogs, guinea pigs, mice, rats, sheep and goats, with mice and rats being preferred.

In preparing the monoclonal antibody-producing cells, an individual of warm-blooded animals, e.g., mice, immunized with an antigen, for which an antibody titer is verified, is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting a labeled protein, which will be later described, with the antiserum followed by assaying the binding activity of the labeling agent bound to the antibody. Fusion can be operated by known methods, for example, according to the Koehler and Milstein method (Kohler and Milstein (1975) Nature 256: 495). Examples of the fusion accelerator are polyethylene glycol (PEG), Sendai virus, etc., of which PEG is preferably employed. Examples of myeloma cells are NS-1, P3U1, SP2/0, etc. and P3U1 is preferably employed. A preferred ratio of the count of the antibody-producing cells (spleen cells) used to the count of myeloma cells is within the range of approximately 1:1 to 20:1. When PEG (preferably, PEG 1000 to PEG 6000) is added in a concentration of approximately 10 to 80% followed by incubating at about 20 to 40° C., preferably at about 30 to 37° C. for about 1 to 10 minutes, an efficient cell fusion can be performed.

Various methods can be used for screening of the monoclonal antibody-producing hybridomas. Examples of such methods include a method which comprises adding the supernatant of hybridoma to a solid phase (e.g., microplate) adsorbed with an antigen of the protein directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase, and the like.

The monoclonal antibody can be selected by publicly known methods or by modifications of these methods. In general, selection can be effected in a medium for animal cells supplemented with HAT (hypoxanthine, aminopterin and thymidine). Any selection and growth medium can be used as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for incubation of a hybridoma (SFM-101, Nissui Seiyaku Co., Ltd.), etc. can be used for the selection and growth medium. Incubation is carried out generally at 20 to 40° C., preferably at about 37° C., for 5 days to 3 weeks, preferably 1 to 2 weeks. The incubation can be conducted normally under 5% carbon dioxide gas. The antibody titer of the culture supernatant of hybridomas can be determined in the same way as in the assay for the antibody titer in antisera described above.

Purification of Monoclonal Antibody

Separation and purification of the monoclonal antibody can be carried out by methods applied to conventional separation and purification of immunoglobulins, in the same way as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

Preparation of Polyclonal Antibody

The polyclonal antibody against PAP2a can be produced by publicly known methods or their modifications. For example, a complex of immunogen (protein antigen) and a carrier protein is prepared, and a mammal is immunized with the complex in a manner similar to the method described above for the production of monoclonal antibodies. The product containing the antibody against the protein of the present invention is collected from the immunized animal followed by separation and purification of the antibody. In the complex of an immunogen and a carrier protein used to immunize a mammal, the type of carrier protein and the mixing ratio of a carrier to hapten may be any type in any ratio, as long as the antibody is efficiently produced to the hapten immunized by crosslinking to the carrier. For example, bovine serum albumin, bovine thyroglobulins, keyhole limpet hemocyanin, etc. is coupled to hapten in a carrier-to-hapten weight ratio of approximately 0.1 to 20, preferably about 1 to about 5. A variety of condensing agents can be used for the coupling of a carrier to hapten. Glutaraldehyde, carbodiimide, maleimide activated ester, activated ester reagents containing thiol group or dithiopyridyl group, etc. are used for the coupling. The condensation product is administered to warm-blooded animals either solely or together with carriers or diluents to the site in which the antibody can be produced by the administration. In order to potentiate the antibody productivity upon the administration, complete Freund's adjuvant or incomplete Freund's adjuvant may be administered. The administration is usually made once approximately in every about 2 to 6 weeks and about 3 to about 10 times in total. The polyclonal antibody can be collected from the blood, ascites, etc., preferably from the blood, etc. of mammals immunized by the method described above. The polyclonal antibody titer in antiserum can be assayed by the same procedure as used for determination of the serum antibody titer described above. The separation and purification of the polyclonal antibody can be carried out in accordance with the method for the separation and purification of immunoglobulins performed as applied to the separation and purification of monoclonal antibodies described hereinabove.

Production of Antibody Fragment or Derivative

The Fab is an antibody fragment having a molecular weight of about 50,000 and having an antigen-binding activity, in which about a half of the N-terminal side of H chain and the full length L chain are bound together via a disulfide bond, and which is obtained by treating an IgG with a protease papain (it is cleaved at the 224 amino acid residue of the H chain). The Fab of the present invention can be prepared by treating the antibody binding specifically to PAP2a with a protease papain.

The F(ab')$_2$ is an antibody fragment having a molecular weight of about 100,000 and having an antigen-binding activity, which is slightly larger than the Fab bound via a disulfide bond of the hinge region, and which is obtained by treating an IgG with a protease or pepsin (it is cleaved at the 234th amino acid residue of the H chain). The F(ab')$_2$ of the present invention can be prepared by treating the antibody binding specifically to PAP2a with protease pepsin.

The Fab' is an antibody fragment having a molecular weight of about 50,000 and having an antigen-binding activity, in which the disulfide bond of the hinge region in the above F(ab')$_2$ is cleaved. The Fab' of the present invention can be prepared by treating the antibody binding specifically to PAP2a with a reducing agent dithiothreitol.

The Fab, F(ab') or Fab' can also be produced by inserting DNA encoding the Fab, F(ab') or Fab' fragment into an expression vector for prokaryote or an expression vector for eukaryote, and introducing the vector into a prokaryote or a eukaryote to express them (cf. e.g., Co M. S., et al., J. Immunol. (1994) 152, 2968-2976; Better M. & Horwitz A. H., Methods in Enzymology (1989) 178, 476-496; Plueckthun, A. & Skerra A. Methods in Enzymology (1989) 178, 497-515; Lamoyi E., Methods in Enzymology (1986) 121, 652-663; Rousseaux J., et al., Methods in Enzymology (1986) 121, 663-669; Bird R. E., et al., TIBTECH (1991) 9, 132-137, etc.).

The single chain antibody fragment (hereinafter sometimes abbreviated as scFv) is VH-P-VL or a VL-P-VH polypeptide, in which one heavy chain variable region (hereinafter abbreviated as VH) and one light chain variable region (hereinafter abbreviated as VL) chain are linked using an appropriate peptide linker (hereinafter abbreviated as P) (cf. e.g., Huston, J. S., et al., Proc. Natl. Acad. Sci. U.S.A. (1988) 85, 5879-5883). The single chain antibody of the present invention can be produced by obtaining a cDNA encoding VH and VL of the antibody binding specifically to PAP2a, constructing a DNA encoding the single chain antibody, inserting the DNA into an expression vector for prokaryote or an expression vector for eukaryote, and then introducing the expression vector into a prokaryote or a eukaryote to express the single chain antibody.

The disulfide stabilized V region fragment (hereinafter sometimes abbreviated as dsFv) refers to a fragment in which polypeptides prepared by substituting one amino acid residue in each of VH and VL with cysteine residue are linked via a disulfide bond between the cysteine residues. The amino acid residue to be substituted with cysteine residue can be selected based on a three-dimensional structure prediction of the antibody in accordance with the method shown by Reiter et al. (Protein Engineering, 7, 697-704 (1994)). As the VH and VL contained in the disulfide stabilized V region fragment used in the present invention, the antibody binding specifically to PAP2a, for example, any one of humanized antibody and human antibody can be used.

The disulfide stabilized V region fragment used in the present invention can be produced by obtaining a cDNA encoding VH and VL of the antibody binding specifically to PAP2a, constructing a DNA encoding the disulfide stabilized V region fragment, inserting the DNA into an expression vector for prokaryote or an expression vector for eukaryote, and then introducing the expression vector into a prokaryote or a eukaryote to express the fragment. A peptide comprising the complementary determining region (hereinafter abbreviated as CDR) is constructed by at least one region of the H chain and L chain CDRs. A plurality of CDRs can be linked directly or via an appropriate peptide linker.

The peptide comprising CDR of the present invention can be produced by obtaining a cDNA encoding VH and VL of the antibody binding specifically to PAP2a, constructing a DNA encoding CDR, inserting the DNA into an expression vector for prokaryote or an expression vector for eukaryote, and then introducing the expression vector into a prokaryote or eukaryote to express the peptide. The peptide comprising CDR can also be produced by chemical synthesis such as the Fmoc method (fluorenylmethoxycarbonyl method), the tBoc method (t-butyloxycarbonyl method), etc.

Humanized Antibody

Antibodies of non-human animals can be modified into human chimeric antibodies, human CDR-grafted antibodies, etc. by using recombinant gene technology and such humanized antibodies can also be used advantageously in the present invention. A human chimeric antibody is an antibody, which antibody variable region (hereinafter referred to as V region) is an antibody of non-human animal and its constant region (hereinafter referred to as C region) is a human antibody (Morrison S. L., et al., Proc. Natl. Acad. Sci. USA, 81 (21), 6851-6855, 1984). A human CDR-grafted antibody is an antibody in which the amino acid sequence of CDR in the V region of antibody of non-human animal is grated to a human antibody at a suitable site (Jones P. T., et al., Nature, 321

(6069), 522-525, 1986). When administered to human, humanized antibodies produce less side effects as compared to antibodies of non-human animals, and maintain long-lasting therapeutic effects. Humanized antibodies can also be prepared as various forms of molecules by recombinant gene technology. For example, when a γ1 subclass is used as the heavy chain (hereinafter H chain) C region of a human antibody, a humanized antibody which is stable in blood and has high effector activities such as antibody-dependent cytotoxicity, etc., can be produced (Co M. S. et al., Cancer Research, 56(5), 1118-1125, 1996). A humanized antibody having high effector activities is useful when destruction of targets such as cancer is desired. On the other hand, where a target neutralizing function alone is required or side effects due to target destruction by effector activities are concerned, a γ4 subclass is suitably used as the H chain C region of a human antibody, since the γ4 subclass generally has low effector activities (Bruggemann M., et al., Journal of Experimental Medicine, 166(5), 1351-1361, 1987; Bindon C. I., et al., Journal of Experimental Medicine, 168(1), 127-142, 1988) so that side effects can be avoided and furthermore, extension of blood half-life can be expected, as opposed to a mouse antibody (Stephens S., et al., Immunology, 85(4), 668-674, 1995). In addition, antibody fragments having smaller molecular weight such as Fab, Fab', F(ab')$_2$, scFv (Bird R. E., et al., Science, 242(4877), 423-426, 1988), dsFv (Webber K. O., et al., Molecular Immunology, 32(4), 249-258, 1995) and CDR-containing peptides (Monfardini C., et al., Journal of Biological Chemistry, 271(6), 2966-2971, 1996) produced from antibodies including humanized antibodies by using protein engineering or genetic engineering can also be used. These antibody fragments have smaller molecular weight as compared to whole antibody molecules, and are excellent in penetration into target tissues (Cancer Research, 52, 3402-3408, 1992).

Antibodies in which a radioisotope, a therapeutic protein, a low molecular agent, etc. is bound to the antibody (including, e.g., a humanized antibody, a human antibody and their antibody fragments) binding specifically to PAP2a of the present invention chemically or by genetic engineering can be produced by binding a radioisotope, a therapeutic protein, a low molecular agent, etc. to at the N-terminal or C-terminal side of the H chain or L chain of the antibodies or antibody fragments binding specifically to PAP2a, at appropriate substituents or side chains of the antibodies and antibody fragments, or at sugar chains in the antibodies and antibody fragments chemically or by genetic engineering (see, e.g., KOTAI-KOGAKU-NYUMON, authored by Osamu Kanemitsu, Chijin Shokan, 1994).

2. Diagnostic and Therapeutic Drug

In another aspect, the present invention provides a diagnostic agent for cancer comprising the anti-PAP2a antibody. The present invention also provides a therapeutic drug for cancer comprising the anti-PAP2a antibody. As used herein, the term "cancer" and "tumor" are used interchangeably as having the same meaning.

As will be specifically described in EXAMPLES herein, the diagnostic or therapeutic drug comprising the anti-PAP2a antibody of the present invention is suitable for the diagnosis or treatment of any disease characterized by overexpression of PAP2a (a cancer preferably including adenocarcinoma, in particular, prostate cancer, lung cancer, pancreatic cancer, ovarian cancer, thyroid cancer or breast cancer).

The anti-PAP2a antibody of the present invention for use in diagnosis or treatment of a cancer may be labeled, if necessary, with a marker substance for monitoring, etc. (e.g., a radioisotope, a fluorescent substance, etc.) in the diagnostic or therapeutic drug of the present invention.

In the diagnostic or therapeutic drug of the present invention, the anti-PAP2a antibody of the present invention can be an agent having neutralizing activities by itself to attenuate the antigen activities, and can also be bound, if necessary, to other agents (e.g., a radioisotope, a therapeutic protein, a low molecular agent, etc., or a viral vector or non-viral vector for gene delivery into a target) for enhancing therapeutic effects through chemical bond or by genetic engineering. Herein, "chemical bond" is intended to include ionic bond, hydrogen bond, covalent bond, bond by intermolecular interactions, bond by hydrophobic interactions, etc. The term "binding by genetic engineering" is intended to include, for example, a binding mode between an antibody and a therapeutic protein when a fused protein consisting of the antibody and the therapeutic protein is constructed by technology such as genetic recombination, etc.

Production of antibody preparations for diagnostic use in vivo and how-to-use are well known in the art. For example, indium 111-labeled antibodies bound to chelators (antibody-chelators) are described for use in imaging by radioimmunoscintography of carcinoembryonic antigen-expressed tumors (Sumerdon, et al., Nucl. Med. Biol., 1990 17:247-254). In particular, these antibody-chelators are used in detecting tumors in patients suspected of having recurrent colorectal cancer (Griffin et al., J. Clin. One., 1991 9:631-640). Antibodies with paramagnetic ions as labels used in magnetic resonance imaging are also described (Lauffer, R. B., Magnetic Resonance in Medicine, 1991 22:339-342).

Antibodies against PAP2a can be used as well. More specifically, labeled antibodies binding specifically to PAP2a can be injected to patients suspected of having a cancer for the purpose of diagnosing of the disease status, stage, etc. of the patient. The label used can be selected depending upon the imaging modality used. For example, radioactive labels such as indium-111 ($^{111}$In), technetium-99m ($^{99m}$Tc) or iodine-131 ($^{131}$I), etc. can be used for planar scans or single photon emission computed tomography. Positron emitting labels such as fluorine-18 ($^{18}$F) can be used for positron emission tomography. Paramagnetic ions such as gadolinium (III) or manganese (II) can be used for magnetic resonance imaging. By monitoring localization of the label, the spread of cancer can be determined. Based on the amount of label within organs or tissues, the presence or absence of cancer in the organs or tissues can be determined.

Preferably, the anti-PAP2a antibody in the diagnostic or therapeutic drug of the present invention is thus bound to a radioisotope, a therapeutic protein, a low molecular agent, a viral vector bearing a therapeutic gene, or the like, chemically or by genetic engineering.

Examples of the "radioisotope" include radioisotope halogen atoms such as fluorine-18, iodine-125 ($^{125}$I), iodine-131, etc. These radioisotope halogen atoms can be labeled as well to antibodies or peptides and widely used as radioisotope diagnostic agent or radioisotope therapeutic agent. Iodization with, e.g., $^{125}$I or $^{131}$I can be performed by publicly known methods such as the chloramine T method, etc., thereby to attach to the antibodies or antibody fragments.

For diagnosis, technetium-99m, indium-111, gallium-67 ($^{67}$Ga), etc. can also be used and yttrium-90 ($^{90}$Y), rhenium-186 ($^{186}$Re), rhenium-188 ($^{188}$Re), etc. can be used for therapy. When the antibody is labeled with a radioisotope, a metal chelator is usually employed. As the metal chelator, EDTA, DTPA, a diaminodithio compound, cyclam, DOTA, etc. are known. These chelators can be used for labeling by a method in which the chelators is previously bound to the antibody followed by labeling with a radioisotope metal and a method in which a radioisotope metal chelate is formed and then bound to the antibody.

Suitable examples of the "therapeutic protein" are cytokines which activate immunity-mediating cells and include human interleukin 2, human granulocyte-macrophage-colony stimulating factor, human macrophage colony stimulating factor, human interleukin 12, etc. The therapeutic protein directly kills cancer cells and lysine or toxins such as diphtheria toxin, etc. can be used. As to fused antibodies to the therapeutic protein, the fused antibodies can be produced by conjugating a cDNA encoding the therapeutic protein to a cDNA encoding the antibody or antibody fragment, constructing a fused DNA encoding the fused antibody, inserting the DNA into an expression vector for prokaryote or an expression vector for eukaryote, and then introducing the expression vector into a prokaryote or eukaryote to express the fused antibody.

The "low molecular agent" as used herein is intended to mean compounds for the diagnosis or treatment except for the "radioisotopes," "therapeutic proteins," etc. Examples of the "low molecular agent" are anticancer agents including alkylating agents such as nitrogen mustard, cyclophosphamide, etc.; metabolic antagonists such as 5-fluorouracyl, methotrexate, etc.; antibiotics such as daunomycin, bleomycin, mitomycin C, daunorubicin, doxorubicin, etc.; plant alkaloids such as vincristine, vinblastine, vindesine, etc.; hormone drugs such as tamoxifen, dexamethasone, and the like (Practice of Oncology, edited by Japanese Society of Clinical Oncology, published by Cancer & Chemotherapy Publishers INC. (1996)); anti-inflammatory agents including steroid agents such as hydrocortisone, prednisone, etc.; non-steroidal drugs such as aspirin, indomethacin, etc.; immunomodulators such as aurothiomalate, penicillamine, etc.; immunosuppressors such as cyclophosphamide, azathiopurine, etc.; antihistaminic agents such as chlorpheniramine maleate, clemastine, etc.; and the like (Inflammation and Anti-inflammatory Therapy, Ishiyaku Publishing Co., 1982); and the like. Examples of the method for conjugating daunomycin to an antibody include a method in which daunomycin and an amino group of the antibody are conjugated via glutaraldehyde, a method in which an amino group of daunomycin and a carboxyl group of the antibody are conjugated via a water-soluble carbodiimide, and the like.

Examples of the "viral vector" which can be used include a viral modified in a way that can be conjugated with the anti-PAP2a antibody of the present invention (e.g., a FZ33 fiber-modified adenovirus). A gene exhibiting therapeutic effects (therapeutic gene), for example, an effect of inducing apoptosis of cancer cells, etc., is incorporated into such a modified viral vector at the target site (e.g., cancer) such as a cell growth-related gene, apoptosis-related gene, immunosuppressing gene, etc. When the viral vector conjugated with the anti-PAP2a antibody is administered together with the anti-PAP2a antibody to a patient who needs gene therapy, the viral vector can be targeted to the site where its antigen (i.e., PAP2a) recognized by the anti-PAP2a antibody is present.

3. Production of Recombinant Adenovirus

The recombinant adenoviral vector typically used in the present invention can be prepared by molecular biological techniques well known in the art. For general techniques for molecular biology, reference can be made to, e.g., Sambrook, J., et al., Molecular Cloning. A laboratory Manual, 2nd Ed., Cold Spring Harbor Laboratory Press, 1989; Ausbel, F. et al., Current Protocols in Molecular Biology, Green Publishing Associates and Wiley-Interscience, 1987; IDENSHI-KOGAKU JIKKEN NOTO, edited by Takaaki Tamura, 2nd revised edition, entire two series, published by YODOSHA, 2001, etc. To produce the recombinant adenovirus, there can be utilized a method in which a genome-terminal protein complex (hereinafter abbreviated as DNA-TPC) bearing the terminal protein covalently bonded to both ends of a viral genome is used, for instance, the Yoshida et al. method (Yoshida, et al., Hum. Gene Ther., 9:2503-1515 (1998)). These techniques are all well known to those skilled in the art. According to a typical method, first, a desired gene is incorporated into a cosmid cassette such as pAxCw, pAxCAwt, etc. to prepare a cosmid. On the other hand, DNA-TPC is prepared from virus and previously digested with an appropriate restriction enzyme. Next, the aforesaid cosmid and DNA-TPC treated with a restriction enzyme are cotransfected to appropriate host cells, e.g., 293 cells. Subsequently, the cells are cultured under appropriate conditions for a given period of time. Thus, recombinant adenovirus particles released in a medium can be recovered.

The recombinant adenovirus particles typically used in the present invention can be prepared in large quantities by transfecting a nucleic acid molecule for recombinant adenovirus expression to an appropriate culture cell as described above, further culturing the cell and recovering the supernatant. If necessary, the recovered adenovirus can be further subcultured a number of times as required to prepare adenoviral vector particles in larger quantities. Cells suitable for growth and recovery adenovirus, conditions for transfection, culture conditions of the transfected cells, media, etc. are well known to those skilled in the art. For example, when adenovirus lacking the E1A or E1B region frequently used generally is grown, cells like 293 cells which constantly express E1A and E1B can be used. If necessary, concentration and purification can be performed using cesium chloride density gradient centrifugation. By concentration, a viral solution of a titer as high as about $10^9 \sim 10^{11}$ particles/ml can be obtained.

In the nucleic acid molecule for recombinant adenovirus expression, which is typically used in the present invention, a foreign gene can be incorporated and the incorporated gene can be introduced into a target cell efficiently. The foreign gene incorporated into the nucleic acid molecule for recombinant adenovirus expression typically used in the present invention includes a gene encoding a molecule showing cytotoxicity directly or indirectly to a target cell, a cell growth factor, a cell growth suppressing factor, an apoptosis regulating gene, a cancer suppressing gene, a cell cycle controlling gene, an immunomodulating gene, etc. In addition, a suicide gene to be used in combination of a non-toxic prodrug can also be incorporated. Such a combination includes a combination of herpes simplex virus-thymidine kinase (HSVtk) and ganciclovir (HSVtk/GCV), a combination of cyto sine deaminase and 5-fluorocytosine (CD/5FC), a combination of uracyl phosphoribosyl transferase (UP) and 5-fluorouracyl (5FU) (UP/5FU), and a system wherein HSVtk and UP are combined (UPTK15FU+GCV). These foreign genes are generally replaced by the E1 region and/or the E3 region of the adenovirus genome or inserted into these regions.

For production of the fiber-modified recombinant adenovirus, reference can be made to the published reports (Yoshida et al., Hum. Gene Ther., 1998; Nakamura et al., Hum. Gene Ther. 2002; Nakamura et al., J. Virol. 2003, etc.).

Non-limiting examples of the vector preferably used in the present invention include a FZ33 fiber-modified adenovirus modified to conjugate to an antibody at the Fc domain, a modified adenovirus in which an antibody is bound to adenovirus in an optional manner (covalent bond, biotin-avidin crosslinking, virus enclosed by polyethylene glycol with an antibody chemically bound, etc.), and the like. As illustratively outlined in FIG. 2, the FZ33 fiber-modified adenovirus is an adenovirus in which a reporter gene such as lacZ, EGFP, etc. is incorporated using as a basis the FZ33 fiber-modified Ad5 virus containing the Z33 motif (FNMQQQRRFYEAL-HDPNLNEEQRNAKIKSIRDD (SEQ ID NO: 21)) from protein A bound to the Fc domain of an antibody in the HI loop site (ngtqetglik (SEQ ID NO: 30)—idasdttpsa (SEQ ID NO: 31)) of the knob. This is a non-limiting example and those skilled in the art can understand that various variant viruses modified at the envelope or capsid of various viruses such as other viruses (e.g., retrovirus, lentivirus, herpes simplex virus, sindbis virus, measles virus, Sendai virus, reovirus, poxvirus, poliovirus, coxsackie virus, adenovirus-associated virus, etc.) and other modified viruses in which an antibody is bound to the various viruses described above in an optional manner (e.g., covalent bond, biotin-avidin crosslinking, virus enclosed by polyethylene glycol with an antibody chemically bound, etc.) can also be used in combination with the anti-PAP2a antibody. Those skilled in the art can also understand that not only viral vectors but also non-viral vectors such as liposome vector, Sendai virus envelope vector, plasmid DNA naked vector, etc, can also be used in combination with the anti-PAP2a antibody, in the form of modified non-viral vectors wherein an antibody is bound in any manner (a method of binding an antibody-bound molecule such as FZ33, chemical covalent bond, biotin-avidin crosslinking, a vector enclosed by polyethylene glycol with an antibody chemically bound, etc.).

Use of the viral vectors modified to be capable of binding to the anti-PAP2a antibody of the present invention provides the following advantages. Generally when a viral vector is used, targeting is directed to cells, which express a originally recognized by the virus on the cell surface (for example, CAR for adenovirus, a high-affinity laminin receptor (LAMR) for sindbis virus, CD155 for poliovirus, ICAM/DAF for coxsackie virus A21, SLAM/CD46 for measles virus, etc.). Accordingly, it is generally difficult to introduce any effective gene targeting using a viral vector into cells which fails to express or poorly express a cell surface receptor specific to the virus used. By using the viral vector modified to be capable of binding or bind to the anti-PAP2a antibody of the present invention, however, the targeting entry and expression of a therapeutic gene can be facilitated using the viral vector, as far as the cells express PAP2a even though the cells fail to express its cell surface receptor intrinsic to the virus.

For production of the recombinant adenovirus used in the present invention, reference can be made to the following literatures.

Yoshida Y., Sadata A., Zhang W., Shinoura N. and Hamada H., "Generation of fiber-mutant recombinant adenoviruses for gene therapy of malignant glioma." Human Gene Therapy, 9(17): 2503-2515, 1998.

Nakamura T., Sato K. and Hamada H., "Effective Gene Transfer to Human Melanomas via Integrin-Targeted Adenoviral Vectors." Hum. Gene Ther., 13(5): 613-626, 2002.

Nakamura T., Sato K. and Hamada H., "Reduction of natural adenovirus tropism to the liver by both ablation of fiber-Coxsackie virus and adenovirus receptor interaction and use of replaceable short fiber." J. Virol., 77(4): 2512-2521, 2003.

Uchida H., Tanaka T., Sasaki K., Kato K., Dehari H., Ito Y., Kobune M., Miyagishi M., Taira K., Tahara H., Hamada H., "Adenovirus-Mediated Transfer of siRNA against Survivin Induced Apoptosis and Attenuated Tumor Cell Growth in Vitro and in Vivo." Mol. Ther., 10(1): 162-71, 2004.

Volpers C. et al. "Antibody-mediated targeting of an adenovirus vector modified to contain a synthetic immunoglobulin G-binding domain in the capsid." J. Virol., 77: 2093-2104, 2003.

Braisted A. C. and Wells J. A., "Minimizing a binding domain from Protein A." Proc. Natl. Acad. Sci. USA, 93:5688-5692, 1996.

4. Drug Targeting

As is clearly noted from the description 2. above, an agent useful for the diagnosis and/or treatment of a disease can be delivered to a target site of the disease, using the anti-PAP2a antibody of the present invention. Thus, the present invention provides a method for delivering an agent useful for the diagnosis and/or treatment of a disease to a target site of the disease, using the anti-PAP2a antibody of the present invention.

Examples of the "agent" include the radioisotopes, therapeutic proteins, low molecular agents, therapeutic genes, etc. described hereinabove.

As a typical example, the anti-PAP2a antibody of the present invention is bound to the fiber-modified adenoviral vector in which a therapeutic gene capable of binding to the anti-PAP2a antibody is incorporated. Thus, the multiplicity of infection to the targeted cells can be enhanced as compared to intrinsic adenovirus receptor (CAR)-dependent infection only, and delivery of a therapeutic gene into a target site can be effectively performed using the fiber-modified adenovirus.

In the present invention, the "target site" includes cells, tissues, organs, etc. which highly express PAP2a when compared to normal cells, especially tumor cells where PAP2a is highly expressed, as compared to normal cells. Non-limiting examples of such cells include preferably adenocarcinoma cells, and more preferred examples for the purpose of the present invention can include pancreatic cancer cells, lung cancer cells, prostate cancer cells, thyroid cancer cells, ovarian cancer cells, breast cancer cells, etc.

5. Treatment of Disease Mediated by Effector Cell Using Anti-PAP2a Antibody of the Invention and Opsonization In a further aspect, the present invention provides a therapeutic agent for a disease (e.g., cancer) characterized by overexpression of PAP2a, which acts to lyse a PAP2a expressing cell or inhibit its growth via an immunological effector cell when the anti-PAP2a antibody contained in the therapeutic agent of the present invention as an effective component is administered to a subject, and a method for treating the disease, which comprises administering such a therapeutic agent to a subject.

The term "immunological effector cell" is used herein in the meaning as generally used in the art and particularly refers to an immune cell which is involved in the effector phase of an immune response, as opposed to the cognitive and activation phases of an immune response. Non-limiting examples of the immunological effector cell include T cells (e.g., cytolytic T cells (CTL), helper T cells (Th)), NK cells, NK-like T cells, B cells, monocytes, macrophages, dendritic cells, Kupffer cells, Langerhans cells, polymorphonuclear leukocytes (e.g., neutrophils, eosinophils, basophils and mast cells), and the like. For example, the anti-PAP2a antibody of the present invention can bind to the Fc receptor on the surface of the immunological effector cells. Effector cells express specific Fc receptors and exhibit specific immune functions, for example, a neutrophil can induce antibody-dependent cell-mediated cytotoxicity ADCC. As such, an immunological effector cell can phagocytose or lyse a PAP2a expressing cell.

In a still further aspect, the present invention provides a therapeutic agent for a disease (e.g., cancer) characterized by overexpression of PAP2a, which acts to opsonizes a PAP2a expressing cell when the anti-PAP2a antibody contained in the therapeutic agent of the present invention as an effective component is administered to a subject, and a method for treating the disease, which comprises administering such a therapeutic agent to a subject.

For example, the anti-PAP2a antibody of the present invention can be a bispecific or multispecific molecule comprising at least one first binding specificity for PAP2a and a second binding specificity for a second target epitope. For example, the second target epitope described above can be an Fc receptor such as human FcγRI, a human Fcα receptor, etc. The present invention thus includes bispecific and multi specific molecules capable of binding both to FcγR, FcαR or FcεR-expressing effector cells (e.g., monocytes, macrophages, polymorphonuclear cells, etc.), and to target cells expressing PAP2a. The second target epitope described above can also be a complement-binding region. The anti-PAP2a antibody includes bispecific and multi specific molecules capable of binding both to effector cells (e.g., monocytes, macrophages, polymorphonuclear cells, etc.), which express a complementary receptor via a complement, and target cells, which express PAP2a. These bispecific and multispecific molecules can target PAP2a expressing cells to effector cell and induce Fc receptor-mediated effector cell activities, such as phagocytosis of PAP2a expressing cells, ADCC, cytokine release, generation of superoxide anions, etc.

6. Method for Detecting and/or Quantifying PAP2a

In one aspect, the present invention provides a method for diagnosing cancer, which comprises the step of detecting and/or quantifying a PAP2a protein, its fragment, or a nucleic acid encoding the same, in a biological sample derived from a subject, as a diagnostic marker.

As used herein, the term "subject" is intended to mean a human subject suffering from a disease characterized by overexpression of PAP2a, typically cancer, or suspected of having such a disease, or at risk for such a disease. Representative examples of "cancer" which fits the purpose of the present invention preferably include, but not limited to, adenocarcinoma, more preferably pancreatic cancer, prostate cancer, lung cancer, thyroid cancer, ovarian cancer and breast cancer.

As used herein, the term "biological sample" is intended to mean cells, tissues, organs, body fluids, etc. collected from a subject for inspection. Body fluids include blood, lymphatic fluids, sperm, saliva, sweat and the like. Blood include blood products such as serum, plasma, etc., as well as whole blood. More specifically, biological samples may be cancer cells (or cancer tissues), preferably pancreatic cancer cells, prostate cancer cells, thyroid cancer cells, lung cancer cells, ovarian cancer cells or breast cancer cells, and most preferably pancreatic cancer cells and lung cancer cells.

In one aspect, the present invention provides a method for immunologically detecting and/or quantifying PAP2a in a biological sample derived from a subject, using the anti-PAP2a antibody.

In a preferred embodiment, the method of the present invention comprises
(1) the step of contacting the biological sample with the anti-PAP2a antibody, and,
(2) the step of detecting and/or quantifying the binding of PAP2a in said biological sample with said anti-PAP2a antibody.

The method can be used for diagnosis of diseases characterized by higher expression of PAP2a than in normal cells, typically cancer including adenocarcinoma, more preferably pancreatic cancer, prostate cancer, thyroid cancer, lung cancer, ovarian cancer, breast cancer, etc. Usually, the level (or amount) of PAP2a in a biological sample is evaluated based on the level (or amount) of the conjugate of PAP2a and the anti-PAP2a antibody. The level of PAP2a in a biological sample is compared with the level assayed with a normal human control and based on its change (or difference), it is diagnosed if cancer is present. Usually, a higher level of PAP2a than in normal human control indicates the presence of cancer. In this case, the PAP2a level as high as usually at least 2 times, preferably about 5 times, indicates a positive result that the subject suffers from cancer. Alternatively, the presence of PAP2a itself in a biological sample can be indicative of cancer in the subject.

In biological samples derived from human, assay technologies which can be used to determine the expression level of proteins like PAP2a are well known to those skilled in the art. Such assay methods include enzyme-linked immunosorbent assay (ELISA), western blot analysis, radioimmunoassay, binding protein competitive assay, reverse transcription-PCR (RT-PCR) assay, immunohistochemical assay, in situ hybridization assay and proteomics approach. Among others, ELISA is frequently preferred for diagnosis of gene expression protein in biological fluids.

In the beginning ELISA comprises preparing an antibody, preferably a monoclonal antibody binding specifically to PAP2a, if not readily available from commercial sources. In addition, a reporter antibody, which binds specifically to PAP2a, is generally prepared. The reporter antibody is attached to a detectable reagent such as a radioactive, fluorescent or enzymatic reagent, for example horseradish peroxidase enzyme, alkaline phosphatase, etc.

To carry out ELISA, an antibody binding specifically to PAP2a is incubated on a solid support, e.g. a polystyrene dish, etc. to bind the antibody. Any free protein binding sites on the dish are then coated by incubating with a non-specific protein such as bovine serum albumin. Next, the sample to be analyzed is incubated in the dish, while PAP2a binds to the specific antibody attached to the polystyrene dish. Unbound sample is washed out with buffer. A reporter antibody specifically targeted to PAP2a and linked to a detectable reagent such as horseradish peroxidase is placed in the dish, and the reporter antibody binds to any monoclonal antibody bound to PAP2a. Next, unbound reporter antibody is washed out. Reagents for peroxidase activity, including a calorimetric substrate are then added to the dish. Immobilized peroxidase, linked to the PAP2a antibody, produces a colored reaction product. The amount of color developed in a given time period is proportional to the amount of PAP2a protein present in the sample. Generally, quantitative results are obtained by referring to a standard curve.

A competitive assay can also be employed, in which an antibody binding specifically to PAP2a is attached to a solid support and labeled PAP2a, and samples derived from the patient and human control are passed over the solid support and the detected amount of label attached to the solid support can be correlated to a quantity of PAP2a in the sample.

In addition to the respective assay methods illustratively shown above, any immunological assay method such as sandwich enzyme immunoassay, fluoroimmunoassay (FIA), time-resolved fluorescence immunoassay (TRFIA), enzyme-linked immunoassay (EIA), luminescence immunoassay (LIA), electrochemiluminescence immunoassay (ECLIA), latex agglutination assay, immunoprecipitation assay, precipitation reaction assay, gel-diffusion precipitation reaction assay, immunodiffusion assay, agglutination assay, complement fixation assay, immunoradiometric assay, fluorescence immunoassay and protein A immunoassay, etc. can be used in the present invention.

In terms of using PAP2a as a diagnostic marker, the nucleic acid method using the entire or a part of the nucleic acid sequence of PAP2a as a hybridization probe can also be used to detect PAP2a mRNA as a marker for cancer including lung cancer. Polymerase chain reaction (PCR) and other nucleic acid methods, such as ligase chain reaction (LCR), nucleic acid sequence based amplification (NASABA), etc. can be used to detect malignant cells for diagnosis and monitoring of various malignancies. For example, reverse-transcriptase PCR (RT-PCR) is a powerful technique that can be used to detect the presence of a specific mRNA population in a complex mixture of thousands of other mRNA species. In RT-PCR, a mRNA species is first reverse transcribed to complementary DNA (cDNA) using a reverse transcriptase as the enzyme, and the cDNA is then amplified as in a standard PCR reaction. RT-PCR can thus reveal by amplification the presence of a single species of mRNA. Accordingly, if the mRNA is highly specific to the cell that produces the same, RT-PCR can be used to identify the presence of a specific type of cell. The real time PCR method can also be used to diagnose cancer of a subject using PAP2a as a marker, in comparison between the subject and a healthy subject after quantifying a nucleic acid (e.g., mRNA) encoding PAP2a.

Furthermore, PAP2a can also be used as a marker to monitor the process of progression of cancer of a subject or the therapeutic process. Such a cancer may be any kind so long as it is a PAP2a-positive cancer. PAP2a can be advantageously used for diagnosis of PAP2a-positive adenocarcinoma, more specifically, PAP2a-positive lung cancer, pancreatic cancer, prostate cancer, thyroid cancer, ovarian cancer, breast cancer, etc. For example, by a combination of fractionation and concentration (enrichment) of cells using antibodies and magnetic beads with the detection method of mRNA with high sensitivity by RT-PCR, several tumor cells present in, for example, 5 ml of blood from a subject can be detected. Diagnosis of tumor with high sensitivity and specificity can be made by detecting tumor cells present in blood and detecting or assaying the expression level of its PAP2a or mRNA level. For these methods, reference can be further made to the following reference literatures.

Zieglschmid V, Hollmann C, Bocher O., "Detection of disseminated tumor cells in peripheral blood." Crit. Rev. Clin. Lab. Sci., 2005; 42(2):155-96.

Waguri, N., Suda, T., Nomoto, M., Kawai, H., Mita, Y., Kuroiwa, T., Igarashi, M., Kobayashi, M., Fukuhara, Y., Aoyagi, Y., "Sensitive and specific detection of circulating cancer cells in patients with hepatocellular carcinoma; detection of human telomerase reverse transcriptase messenger RNA after immunomagnetic separation." Clin. Cancer. Res., 2003 Aug. 1; 9(8):3004-11.

Zhang, Y. L., Feng, J. G., Gou, J. M., Zhou, L. X., Wang, P., "Detection of CK20mRNA in peripheral blood of pancreatic cancer and its clinical significance." World J. Gastroenterol., 2005 Feb. 21; 11(7):1023-7.

Demel, U., Tilz, G. P., Foeldes-Papp, Z., Gutierrez, B., Albert, W. H., Bocher, O., "Detection of tumor cells in the peripheral blood of patients with breast cancer. Development of a new sensitive and specific immunomolecular assay." J. Exp. Clin. Cancer Res., 2004 September; 23(3):465-8.

Hybridization to clones or oligonucleotides arrayed on a solid support (namely, gridding) can also be used to both detect the expression of and quantify the level of expression of that gene. According to this approach, a cDNA encoding the PAP2a gene is fixed to a substrate. The substrate can be of any suitable material including but not limited to glass, nitrocellulose, nylon or plastic. At least a part of the DNA encoding the PAP2a gene is attached to the substrate and then incubated with an analyte, which may be RNA isolated from the tissue of interest or its complementary DNA (cDNA) as a copy of the RNA. Hybridization of the DNA bound to the substrate to the analyte can be detected and quantified by several means including but not limited to radioactive labeling or fluorescence labeling of the analyte or a secondary molecule designed to detect the hybrid. Non-limiting examples of the label which can be used in the present invention include a radioisotope, a fluorogenic substrate, a luminescent substrate, a free radical substrate, a particle, bacteriophage, a cell, a metal, an enzyme, a co-enzyme, etc. Quantification of the level of gene expression can be performed by comparison of the intensity of a signal from the analyte with that determined from known standards. The standards can be obtained by in vitro transcription of the target gene, quantification of the yield, and generation of a standard curve using the material.

In proteomics approach, two-dimensional electrophoresis is a technique well known to those skilled in the art. More specifically, individual proteins from a sample such as serum can be isolated by sequential separation by different properties of these proteins on polyacrylamide gels. First, proteins are separated by size using an electric current. The current acts uniformly on all proteins so that smaller proteins move more rapidly on the gel than larger proteins. In the two dimension, a current is applied perpendicularly to the one dimension to separate proteins based on the specific electric charge carried by each protein, not based on the size of a protein. Since two proteins with different sequences cannot be identical in terms of both size and charge, the result of two-dimensional separation is a square gel in which each protein occupies a unique spot. Analysis of the spots with chemical or antibody probes or subsequent protein microsequencing can reveal the relative abundance of a given protein and identity the proteins in the sample.

The methods for detection and/or quantification described above in detail can be carried out on samples derived from various cells, body fluids and/or tissue extracts (homogenates or solubilized tissues) obtained from patients or subjects, including tissue biopsy and autopsy materials. Body fluids useful for the present invention include blood, urine, saliva, or any other body secretions or their derivatives. Blood includes whole blood, plasma, serum or any derivatives from blood.

7. Method for Detecting and/or Quantifying Anti-PAP2a Autoantibody

In another aspect, the present invention provides a method for detecting and/or quantifying an autoantibody against PAP2a (anti-PAP2a autoantibody) in a biological sample from a subject.

The anti-PAP2a autoantibody in a biological sample from a subject can be detected by any of many methods, typically immunological assays, including, for example, Western blotting, radioimmunoassay, ELISA, sandwich immunoassay, fluoroimmunoassay (FIA), time-resolved fluorescence immunoassay (TRFIA), enzyme-linked immunoassay (EIA), luminescence immunoassay (LIA), electrochemiluminescence immunoassay (ECLIA), latex agglutination assay, immunoprecipitation assay, gel-diffusion precipitation reaction assay, immunodiffusion assay, agglutination assay, complement fixation assay, immunoradiometric assay, protein A immunoassay, etc.

Such immunoassay can be performed by various methods. For example, one method to perform such assay involves immobilization of the PAP2a protein to a solid support and detection of the anti-PAP2a antibody specific for the same. The PAP2a protein used for the assay of the present invention can be produced by DNA technology well known in the art.

For example, a DNA encoding the PAP2a protein is introduced into an appropriate expression vector by genetic recombinant technology, whereby the PAP2a protein can be expressed in a large scale. Preferably, fused proteins which facilitate the labeling, immobilization or detection of PAP2a are genetically manipulated (see the technology described in, e.g., Sambrook, et al., 1989, Molecular Cloning: A Laboratory Manual, Cold Spring Harbor Press, Cold Spring Harbor, N.Y.). In another method, the PAP2a protein can be purified from natural sources. For example, the PAP2a protein is purified from prostate cancer cells using protein separation techniques well known in the art. Such purification techniques include but are not limited to molecular sieve chromatography and/or ion exchange chromatography. In practice, a microtiter plate is advantageously used as a solid support for the PAP2a protein.

8. Method of Systematic Search for Target Molecule Candidate in Drug Targeting Therapy The methods specifically described in EXAMPLES herein by way of example for the production of S11 and T13-producing hybridomas and subsequent identification of the antigen are generally useful as a method of systematic search for target molecule candidates in drug target therapy. According to the antibody screening method of the present invention, the antibodies extremely optimized as a diagnostic marker for targeted therapy with high sensitivity and high specificity, and the corresponding antigen molecules can be screened directly and rapidly.

Accordingly, the present invention provides a method of systematic search for target molecule candidates in drug target therapy. More specifically, the present invention provides a method for identifying a monoclonal antibody against a tissue-specific antigen, and a method for identifying the tissue-specific antigen. Preferably, the tissue is a tumor tissue.

In one embodiment, the present invention provides a method for preparing a hybridoma producing a monoclonal antibody against a tissue-specific antigen, and the method comprises:

(1) the step of immunizing a mammal with a cell expressing a tissue-specific antigen or said antigen, and allowing to fuse a lymphocyte from the immunized mammal with a myeloma cell to create a library of hybridomas, and, (2) the step of contacting a fiber variant adenovirus modified to bind to the antibody with said cell in the presence of a product derived from the hybridoma selected from the above library to infect the fiber variant adenovirus to the cell, and assaying the multiplicity of infection of the fiber variant adenovirus to the cell, and, (3) the step of comparing the multiplicity of infection with that of the case where the hybridoma-derived product (antibody, etc.) is not contacted with the cells, selecting a hybridoma with an enhanced multiplicity of infection and cloning the hybridoma.

The present invention also provides a method for screening or preparing a monoclonal antibody against a tissue-specific antigen. The screening method comprises:

(1) the step of immunizing a mammal with a cell expressing a tissue-specific antigen or said antigen, and allowing to fuse a lymphocyte from the immunized mammal with a myeloma cell to create a library of hybridomas, and, (2) the step of contacting a fiber variant adenovirus modified to bind to the antibody with the cell in the presence of a product derived from the hybridoma selected from the library to infect the fiber variant adenovirus to the cell, and assaying the multiplicity of infection of the fiber variant adenovirus to the cell.

Herein, the tissue described above is preferably tumor and the cell is preferably a tumor cell.

Known antibodies (e.g., antibodies produced from the hybridomas deposited to Authority Depositories or commercially available antibodies) may be used as the product (e.g., antibody, etc.) derived from the hybridoma. In that case, the step (1) described above involves acquisition of known antibodies.

Herein, the fiber variant adenovirus is infected to the cell in the presence of the product derived from the hybridoma selected from the library described above, preferably by:

(A) contacting the product derived from the hybridoma selected from the library described above with the cell and the contacting with the fiber variant adenovirus modified to bind to the antibody with the tumor cell described above, or, (B) previously reacting the product derived from the hybridoma selected from the library described above with the fiber variant adenovirus modified to bind to the antibody and then contacting with the cell described above, or, (C) simultaneously administering the product derived from the hybridoma selected from the library described above and the fiber variant adenovirus modified to bind to the antibody to the tumor cell thereby to contact with the cell described above.

The cell described above is preferably a tumor cell.

In the screening method described above, the multiplicity of infection is evaluated and the hybridoma with an enhanced multiplicity of infection, as compared to the case where the hybridoma-derived product (antibody, etc.) is not contacted with the cell, is selected and cloned to give the desired monoclonal antibody. The step of selecting the hybridoma producing the objective monoclonal antibody preferably includes evaluation of the said multiplicity of infection of the fiber variant adenovirus to the cell by reporter gene expression assay. Herein, the fiber variant adenovirus is designed to be capable of expressing a reporter gene for evaluating the multiplicity of infection in the infection described above. The reporter gene expression assay can also be performed by assaying the expression of reporter gene EGFP using a spectrophotometer or flow cytometry. Herein, in the selection of the hybridoma with an enhanced multiplicity of infection, a monoclonal antibody showing the reporter gene expression level as high as at least 2-fold when compared to the case where a control antibody is used, preferably at least 10-fold, more preferably at least 20-fold, more preferably at least 30-fold, more preferably at least 40-fold and most preferably at least 50-fold is selected. As used herein, the "control antibody" refers to antibodies obtained by the existing general procedures, or an antibodies currently commercially available in general, for example, mouse-anti-CEA antibody from IBL (lot No 9G-717) against CEA, and the like.

In an alternative for the reporter gene expression assay, when lacZ is used as a reporter gene, expression of the lacZ gene product can be assayed using a commercially available chemiluminescent β-Gal reporter assay kit (e.g., Galacto Light Plus Reporter Gene Assay System (manufactured by Roche: Code No. T1011), etc.). When a luciferase gene is used as the reporter gene, the expression can be assayed by using Luciferase assay system (Promega, Cat No. E1500) as a commercially available luciferase assay system.

In the method described above, the fiber variant adenovirus modified to bind to the antibody includes, for example, a FZ33 fiber-modified adenovirus containing a Z33 motif of protein A binding to the Fc domain of antibody in the HI loop region of the knob. In the method described above, not only the FZ33 fiber-modified adenovirus but also a vector which is imparted by a property capable of binding to the antibody with at least a certain level of affinity (e.g., a binding affinity showing the binding constant (Ka) of at least $10^7 M^{-1}$, preferably at least $10^8 M^{-1}$ and more preferably $10^9 M^{-1}$ or more), irrespective of type. The fiber variant adenovirus includes, for example, a modified adenovirus of FZ33, etc. modified by binding an antibody binding molecule such as Z33, etc. or peptide to adenovirus in an optional manner (Z33, etc. is covalently bonded, Z33, etc. is crosslinked by biotin-avidin, virus is enclosed by polyethylene glycol with Z33, etc. chemically bound thereto) and the like.

In addition, fiber variant adenovirus lacking the site to be bound to the CAR receptor of the fiber of adenovirus, namely, vectors which are imparted with the property enabling to bind to the antibody with at least a certain level of affinity based on fiber variant adenoviruses prepared by referring to reference literatures such as Kirby, I. et al., J. Virol., 73: 9508-9514, 1999; Mizuguchi et al., Gene Therapy, 9: 769-776, 2002; Roelvink, P. W., et al., Science, 286: 1568-1571, 1999; etc. can be used as well for the purpose of the present invention.

Figures 1, 3:
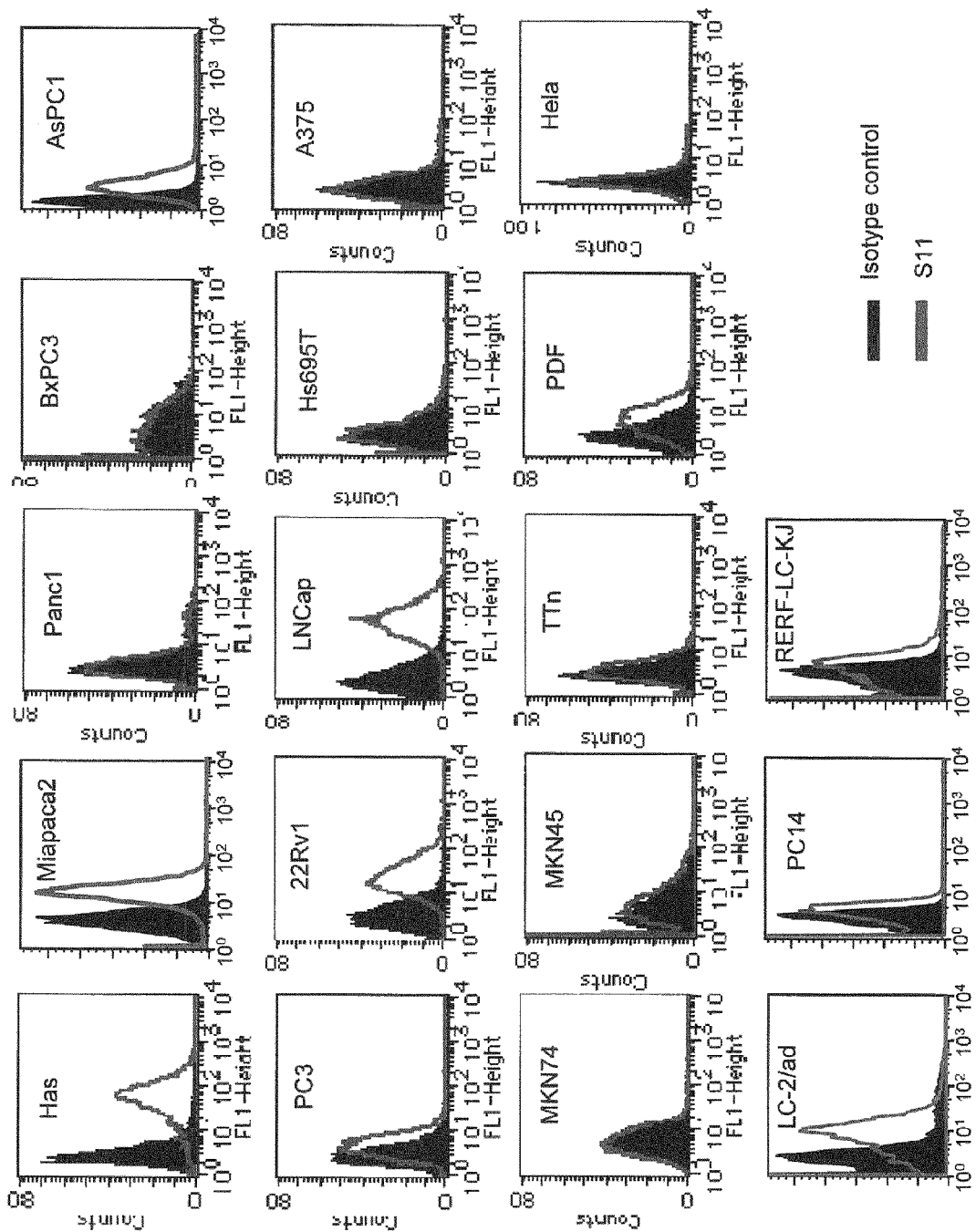
Figures 2, 3:
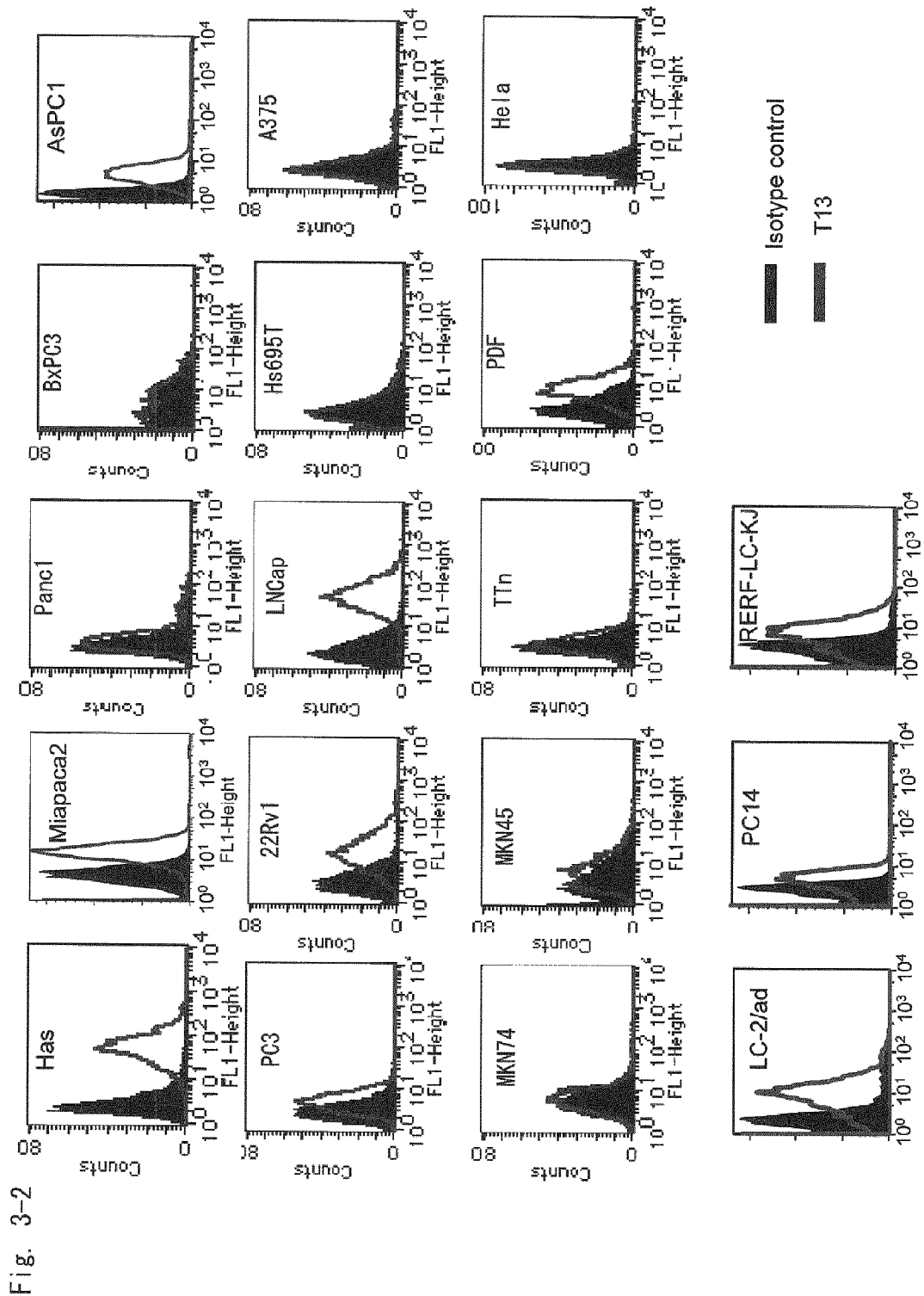
Figures 1, 13:
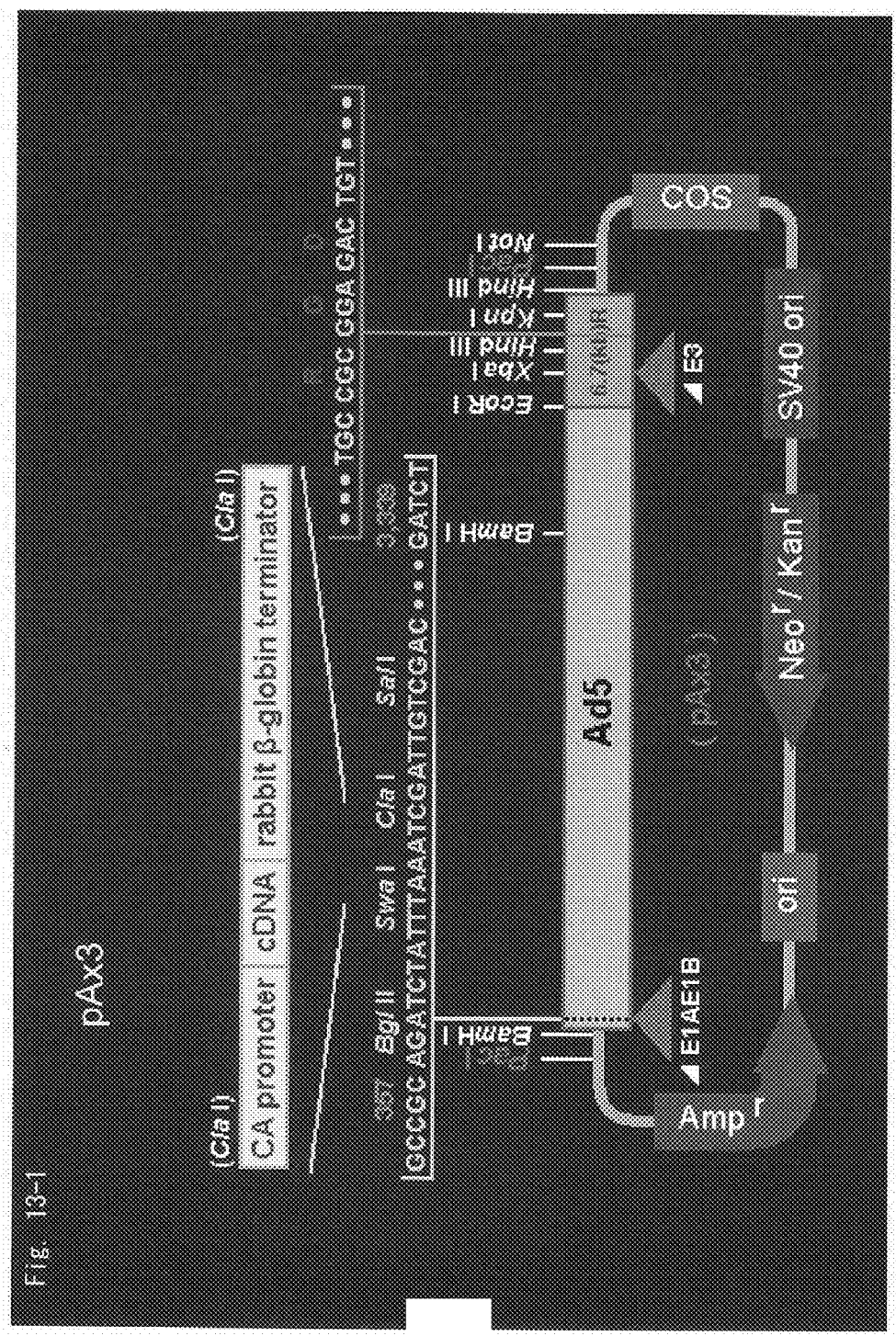
Figures 2, 13:
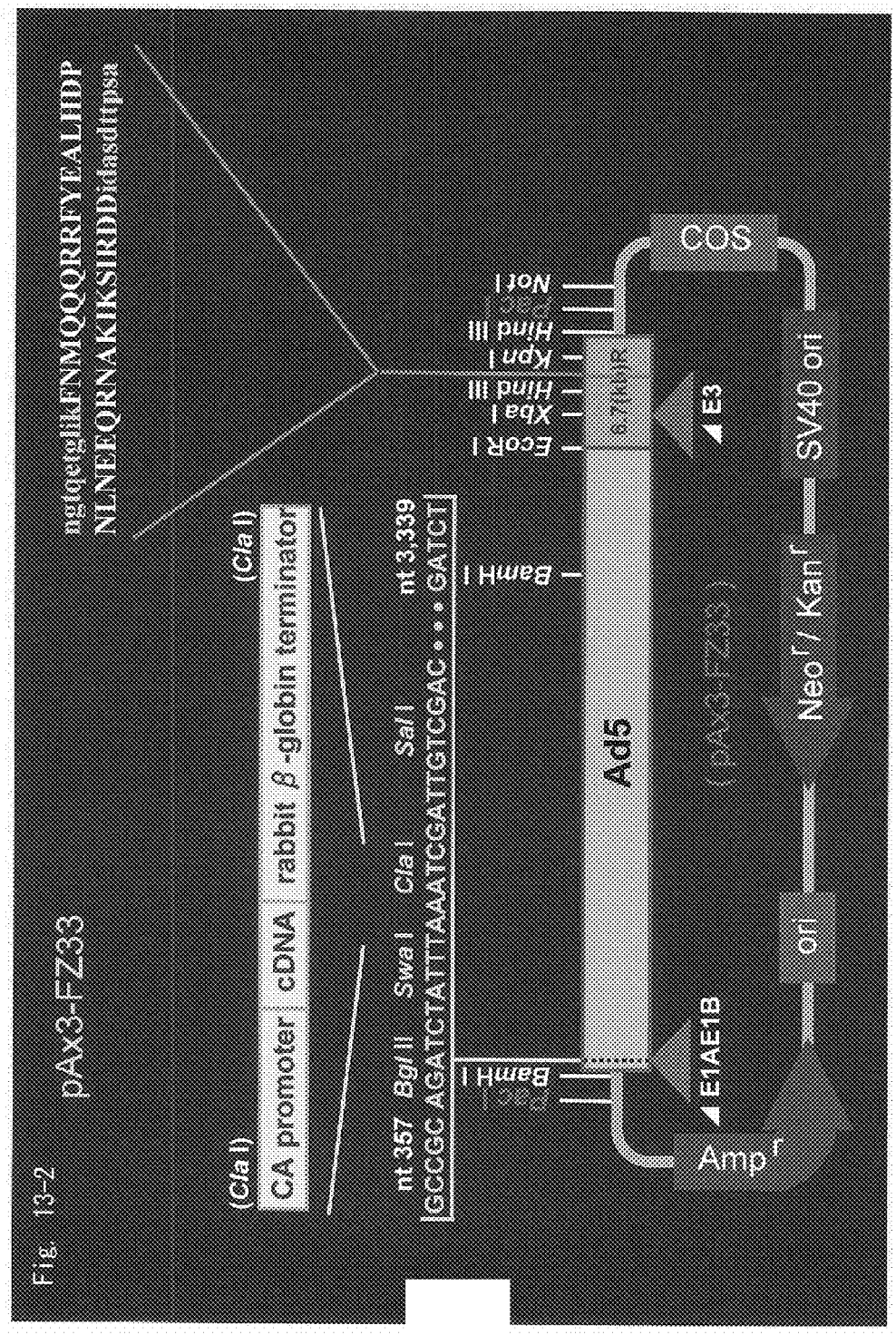

FIG. 13-3 is a schematic view of targeted molecule search using the fiber variant adenovirus Adv-FdZ lacking the binding site to CAR receptor of the fiber of such an adenovirus.

Figure 4:
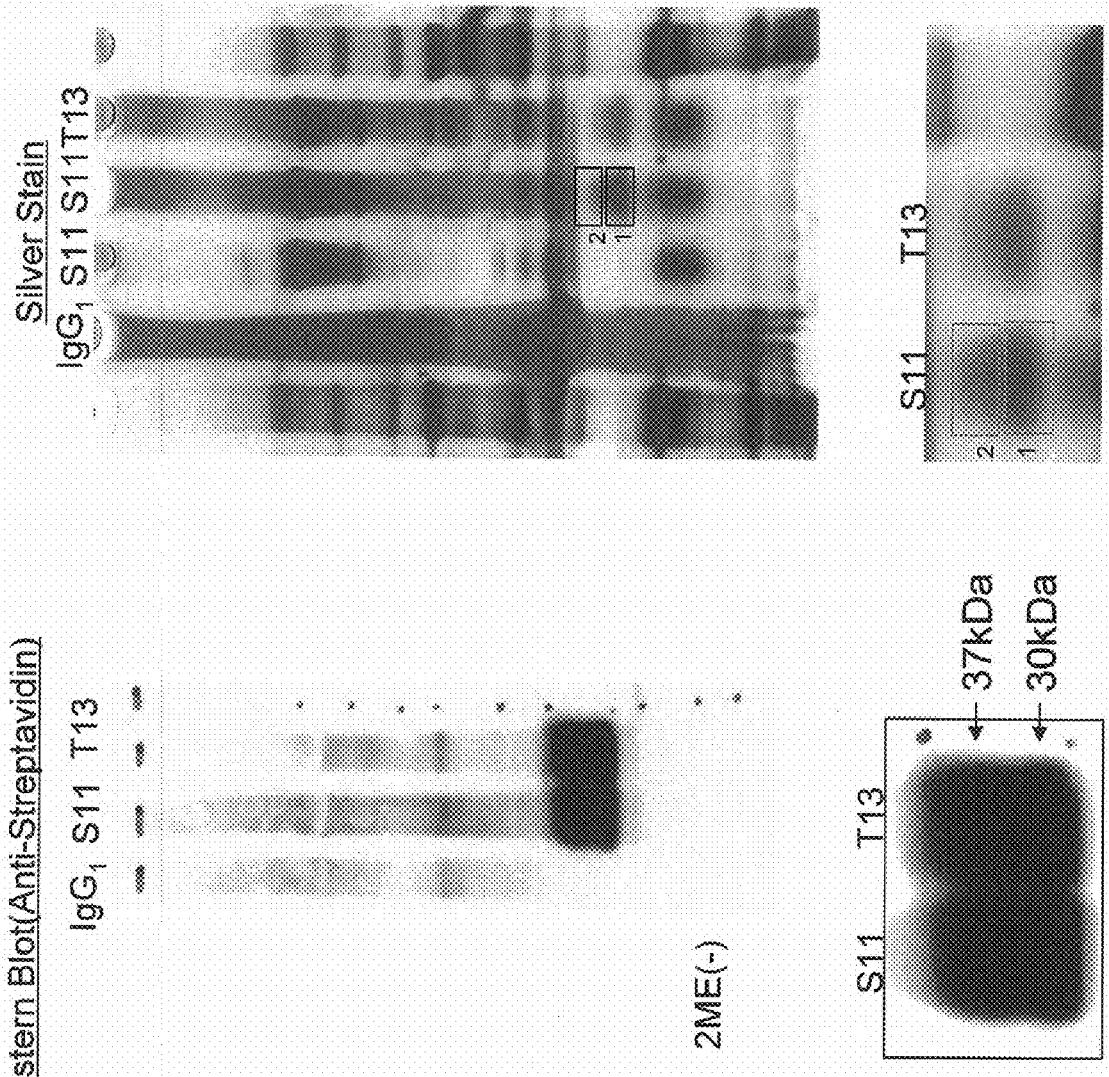
Figures 5, 13:
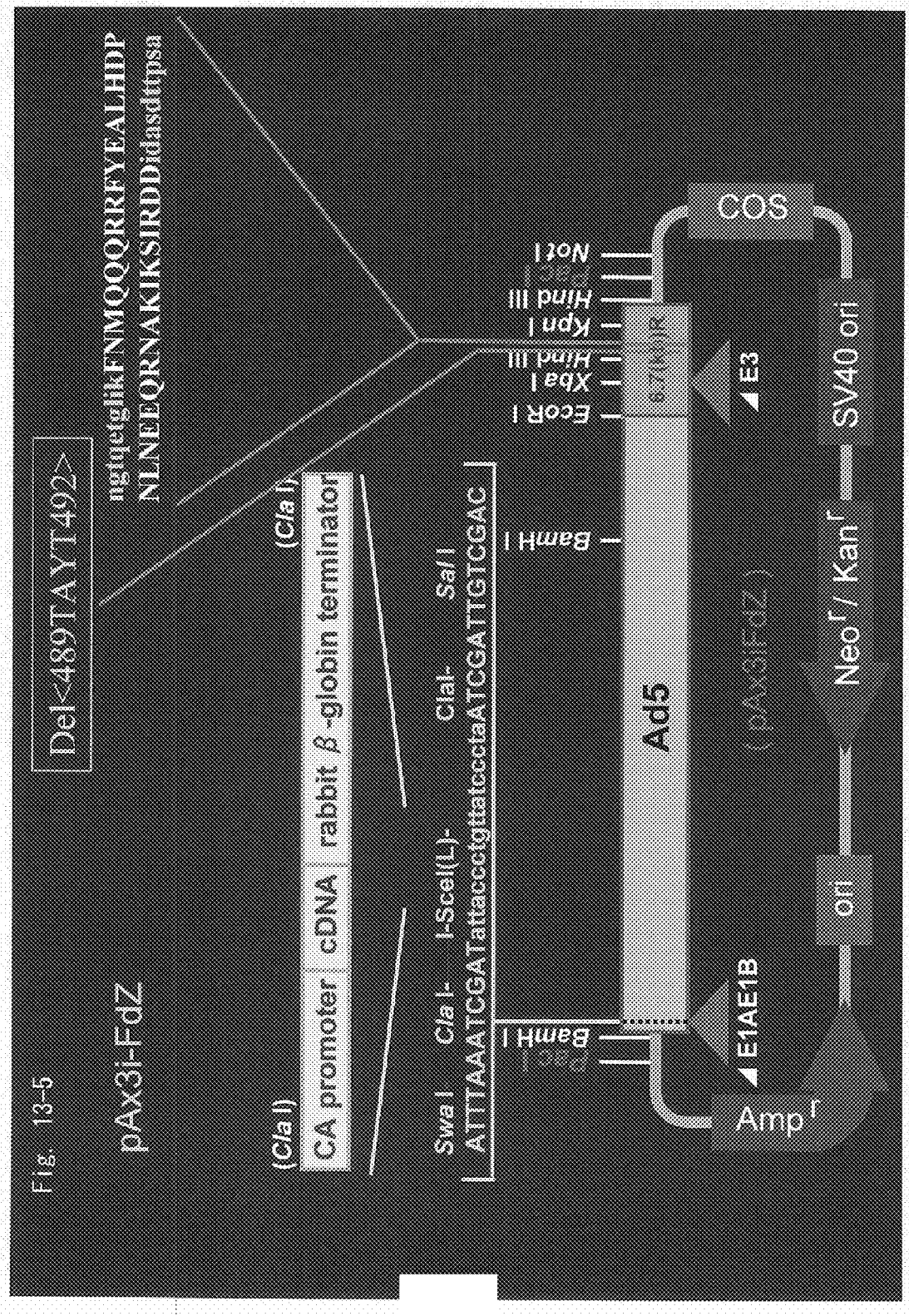

FIG. 13-4 is a schematic view showing the structure of the fiber region of Adv-FdZ, wherein the 489-492 amino acids TAYT (SEQ ID NO: 37) from the N-terminus of the fiber of human type 5 adenovirus are missing. FIG. 13-5 is a schematic view showing one example of plasmid vectors for preparing adenovirus having this deficient fiber. The pAx3iFdZ plasmid shown here is the same as pAx3-FZ33 except for the two points that the cloning site with E1 replacement has the I-SceI restriction enzyme site and the 489-492 amino acids TAYT (SEQ ID NO: 37) are lacking. By using this plasmid pAx3iFdZ, adenoviral vectors which lack the binding site to CAR receptor and enable gene transfer having high target selectivity can be produced. Since Adv-FdZ lacks the binding sit to CAR receptor, gene transfer with higher selectivity can be performed.

In addition, the fiber variant adenovirus may be vectors which lack the reactivity with a population of integrin molecules and are imparted with the property enabling to bind to the antibody with at least a certain level of affinity, based on penton base protein-modified adenoviruses. Furthermore, fiber variant adenoviruses lacking uptake of adenovirus into the liver, namely, vectors which are imparted with the property enabling to bind to the antibody with at least a certain level of affinity, based on fiber-modified adenoviruses prepared by referring to reference literatures such as Smith, T. A. et al (Smith, T. A., Idamakanti, N., Rollence, M. L., Marshall-Neff, J., Kim, J., Mulgrew, K., Nemerow, G. R., Kaleko, M., Stevenson, S. C., Adenovirus serotype 5 fiber shaft influences in vivo gene transfer in mice. Hum. Gene Ther., 2003 May 20; 14(8):777-87), etc. can be used as well for the purpose of the present invention.

These are non-limiting examples and variant viruses modified at the envelope or capsid of other viruses (e.g., retrovirus, lentivirus, herpes simplex virus, sindbis virus, measles virus, Sendai virus, reovirus, poxvirus, poliovirus, coxsackie virus, adenovirus-associated virus, etc.) and modified viruses in which an antibody binding molecule such as Z33, etc. or peptide is bound to the various viruses described above in an optional manner (Z33, etc. is covalently bonded, Z33, etc. is crosslinked by biotin-avidin, virus is enclosed by polyethylene glycol with Z33, etc. chemically bound thereto) can also be used for the method of the present invention. Alternatively, not only viral vectors but also non-viral vectors modified by binding an antibody binding molecule or peptide to the non-viral vectors such as liposome vector, Sendai virus envelope vector, plasmid DNA naked vector, etc. in an optional manner (the antibody binding molecule is chemically bound via covalent bond or crosslinked by biotin-avidin, a vector is enclosed by polyethylene glycol with an antibody binding molecule chemically bound thereto, etc.) can be advantageously used in the present invention.

The reporter gene includes, for example, a fluorescent protein such as lacZ, EGFP, etc., a luciferase gene, etc. These reporter genes can be detected using the reporter gene assay system well known to those skilled in the art. The multiplicity of infection of the FZ33 fiber-modified adenovirus prepared to express, e.g., lacZ can be assayed using a commercially available chemiluminescent β-Gal reporter assay kit (e.g., Galacto Light Plus Reporter Gene Assay System (manufactured by Roche: Code No. T1011), etc.). For the luciferase quantification system, the assay can be performed using a Luciferase assay system (Promega, Cat No. E1500), etc. In the fluorescent protein such as EGFP, etc., the expression level can be assayed using a spectrophotometer or flow cytometry.

For the production and purification of the monoclonal antibody for use in the drug target therapy described above, reference can be made to the following literature.

Hamada H. and Tsuruo T. "Functional role for the 170- to 180-kDa glycoprotein specific to drug-resistant tumor cells as revealed by monoclonal antibodies." Proc. Natl. Acad. Sci. USA, 83: 7785-7789, 1986.

Hamada, H. and Tsuruo, T. "Determination of membrane antigens by a covalent crosslinking method with monoclonal antibodies." Anal. Biochem., 160: 483-488, 1987.

Hamada, H., Hagiwara, K., Nakajima, T. and Tsuruo, T., "Phosphorylation of the Mr 170,000 to 180,000 glycoprotein specific to multidrug-resistant tumor cells: Effects of verapamil, trifluoperazine, and phorbol esters." Cancer Res., 47: 2860-2865, 1987.

Hamada, H. and Tsuruo, T., "Purification of the 170- to 180 kilodalton membrane glycoprotein associated with multidrug resistance: The 170- to 180-kilodalton membrane glycoprotein is an ATPase." J. Biol. Chem., 263: 1454-1458, 1988.

Mishell, B. B., Shiigi, S. M. eds. "Selected Methods in Cellular Immunology" W.H. Freeman and Co., San Francisco, 1980 (translated into Japanese under SAIBO MENEKI JIKKEN SOSA=HO, translated by Imai, et al., published by Rikogakusha Publishing, 1982)

Birch, J. R. and Lennox, E. S. eds. "Monoclonal antibodies: Principles and Applications." Wiley-Liss, New York, 1995.

Goding, J. W., "Monoclonal antibodies: Principles and practice." Academic Press, London, 1983.

Goding, J. W., "Monoclonal antibodies: Principles and practice." Third ed. Academic Press, London, 1996

In a further embodiment, the present invention provides a method for identifying a tissue (e.g., tumor)-specific antigen. The method for identifying a tissue-specific antigen according to the present invention comprises the step of identifying an antigen protein binding specifically to the monoclonal antibody purified from the hybridoma-derived product and determining its amino acid sequence, and the step of performing homology search for the amino acid sequence on a sequence database to identify the antigen protein.

The step of identifying the antigen protein described above includes immunoprecipitation between the antigen and the monoclonal antibody described above, western blot analysis, etc. The step of determining the amino acid sequence can be performed by amino acid sequencing using any known amino acid sequencing methods (e.g., amino acid sequencing using a gas-phase sequencer (e.g., Procise 490cLC ABI, HP241 HP, etc.), separation of peptides obtained by enzymatic cleavage or chemical degradation by HPLC, peptide mapping by gel electrophoresis, amino acid sequence analysis of peptides separated on HPLC using a mass spectrometry device, etc.); preferably, amino acid sequences are determined by mass spectrometry.

In the method described above, homology search on a sequence database can be performed by using programs (e.g., FASTA, BLAST, MASCOT, etc.) and sequencing databases (e.g., PIR, SWISS-PROT, NCBI, etc.), which are well known to those skilled in the art.

By the method for identifying a monoclonal antibody against a tissue-specific antigen and the method for identifying the tissue-specific antigen described above, there is provided a methodology for systematically searching the combination of a target and an antibody practically available for targeted therapy to specific cells, e.g., cancer cells.

9. Sequencing and Cloning of Target Molecule and Antibody in Target Therapy

The amino acid sequences of the antibody and target molecule identified by the method of the present invention described above and the nucleotide sequences encoding the same can be determined by sequencing method well known to those skilled in the art.

For the amino acid sequencing, amino acid sequencing using a gas-phase sequencer (e.g., Procise 490cLC ABI, HP241 HP, etc.), separation of peptides obtained by enzymatic cleavage or chemical degradation by HPLC, peptide mapping by gel electrophoresis, amino acid sequence analysis of peptides separated on HPLC using a mass spectrometry device, etc. can be used. For the nucleotide sequencing, methods for determining nucleotide sequences such as circle sequencing using PCR, etc., which are well known to those skilled in the art, can be used.

Once the nucleotide sequences of a DNA of the target molecule obtained or the antibody against the same are determined, the antibody of the present invention can be produced by genetic engineering based on the determined sequence or fusion products with other molecules can be prepared. The objective DNA can be mass-produced by cloning using plasmid vectors or other molecular biological techniques well known to those skilled in the art (see, e.g., Sambrook, J. et al., Molecular Cloning. A laboratory Manual, 2nd Ed., Cold Spring Harbor Laboratory Press, 1989, etc.).

10. Pharmaceutical Preparation and Method for Administration of Pharmaceutical Preparation The therapeutic agent comprising the antibody of the present invention and therapeutic agent comprising the antibody of the present invention which is bound, chemically or by genetic engineering, to any viral vector carrying any one of a radioisotope, therapeutic protein, low molecular agent and therapeutic gene or any combination thereof, can be prepared into pharmaceutical preparations by known techniques.

In preparing the therapeutic agent of the present invention into pharmaceutical preparations, if necessary, pharmaceutically acceptable carriers can be added in a conventional manner. The carriers include but are not limited to, for example, a surfactant, an excipient, a coloring material, a flavoring material, a preservative, a stabilizer, a buffering agent, a suspending agent, an isotonic agent, a binder, a disintegrator, a lubricant, a fluidity accelerator, a corrigent, etc., and other conventional carriers can also be appropriately used. Specific examples are light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, middle chain triglyceride, polyoxyethylene castor oil 60, sucrose, carboxymethylcellulose, corn starch, inorganic bases, etc.

Dosage forms of the therapeutic agent of the present invention include, for example, oral preparations including tablets, fine powders, pills, powders, granules, subtle granules, soft and hard capsules, film coating agents, pellets, sublingual agents, pastes, etc. and parenteral preparations including injections, suppositories, transdermal agents, ointments, plasters, topical liquid, etc., and optimum dosage forms can be selected by those skilled in the art, depending upon route of administration, subject to be administered, etc. A substance which inhibits the function (or expression) of the PAP2a protein as the effective component can be incorporated into the pharmaceutical composition in an amount of 0.1 to 99.9 wt %.

The dose of the effective component in the agent of the present invention may vary depending upon subject to be administered, target organ, conditions, route of administration, etc. In oral administration, it is administered to the patient (as 60 kg body weight) in a daily dose of about 0.1 to 1,000 mg, preferably about 1.0 to 100 mg and more preferably about 1.0 to 50 mg. In parenteral administration, its single dose may vary depending upon subject to be administered, target organ, conditions, route of administration, etc. When it is administered to the patient (as 60 kg body weight) in the form of, e.g., an injectable preparation, it is generally advantageous to administer the effective component in a single dose of about 0.01 to about 30 mg, preferably about 0.1 to about 20 mg and more preferably about 0.1 to about 10 mg per day. However, the dose can be appropriately determined by doctors' or veterinarians' judgment, considering kind of dosage form, route of administration, age and body weight of the patient, conditions of the patient, etc.

The pharmaceutical preparations thus obtained can also be administered to, e.g., human or other mammals (e.g., rats, rabbits, sheep, swine, bovine, cats, canine, monkeys, etc.). For animal species other than human, the corresponding dose as converted per 60 kg weight can be administered.

The cells, tissues, organs or kind of cancer targeted by the therapeutic agent of the present invention are not limited to particulars but the therapeutic agent is preferably used for the treatment of adenocarcinoma, more preferably adenocarcinoma of prostate, pancreas, thyroid, ovary, breast, etc.

The viral vector particles typically used in the present invention can be used for the treatment, especially treatment of tumor, as one of the components of a pharmaceutical composition in combination with the anti-PAP2a antibody. Where the combination of recombinant adenovirus particles and the anti-PAP2a antibody is used for treatment, they may be used singly but in general they are used together with pharmaceutically acceptable carriers. Such carriers include the carriers described hereinabove and preferably water or an aqueous isotonic solution such as physiological saline, glucose, human albumin, etc. In addition, additives, preservatives, antiseptics, balancing agents, etc., which are generally used pharmaceutically, can also be added. The pharmaceutical composition thus prepared can be administered in an appropriate dosage form and route of administration, depending upon disease to be treated. Dosage form includes, for example, emulsions, syrup, capsules, tablets, granules, injections, ointments, etc. Where the anti-PAP2a antibody-virus vector particles of the present invention or the pharmaceutical composition comprising the same is administered for the purpose of treatment, it is generally preferred to administer the virus particles to an adult in a single dose of $10^3$ to $10^{15}$ but the dose may be varied depending upon disease conditions or properties of target cells/tissues. The frequency of dosing may be once to several times per day. The dosing period may be one day to several months or longer. Alternatively, administration of one to several times is made one set and a number of sets may also be administered intermittently over a long period of time. The virus vector particles or viral vector nucleic acid molecules used in the present invention can be used for the detection of specific cells and/or tissues or diagnosis of disease conditions. For example, the viral vector particles obtained by incorporating a detectable marker gene into the nucleic acid molecule of viral vector and transfecting the same to an appropriate host cell can be used for detection/diagnosis of tumor cells in combination with the anti-PAP2a antibody. When the anti-PAP2a antibody is labeled with a detectable label, the labeled product can be used for detection and diagnosis of tumor cells.

Hereinafter, the present invention will be described in more detail with reference to EXAMPLES but the scope of the present invention is not deemed to be limited to the following EXAMPLES.

EXAMPLES

Example 1

Production of Adenovirus FZ33 Series

In the laboratory of the inventors, FZ33 variant adenovirus was produced by genetic engineering using the materials and procedures described in Yoshida, et al. (Yoshida, et al., Human Gene Therapy, 9(17): 2503-2515, 1998), Nakamura, et al. (Nakamura, T., et al., Hum. Gene Ther., 13(5): 613-626, 2002), etc., basically in accordance with the method of Volpers, et al. (Volpers, C., et al., J. Virol., 77: 2093-2104, 2003). The amino acid sequence Z33 reported by Braisted et al., (Braisted, A. C. and Wells, J. A., Proc. Natl. Acad. Sci. USA, 93: 5688-5692, 1996) was used as the sequence of FZ33 motif.

A. Production of Plasmid pAx3 Containing an RGD-Modified Fiber and the Genome at the Left End of Adenovirus FIG. 13-1 is a schematic representation of plasmid vector pAx3 for producing recombinant adenovirus as a representative example in the present invention. The pAx3 plasmid contains 357 bp from the left end nt1-357 of the genome in human type 5 adenovirus but lacks nt 358-3328 and contains F-RGD mutation in the HI loop of fiber (Nakamura, et al., 2002, supra).

Specifically, the adenoviral vector pAx3 was produced as described below.

First, a 399 bp DNA fragment containing 357 bp from the left end of the adenovirus genome having the nucleotide sequence described later was prepared by PCR using the following primers.

The 5'-end primer:
(SEQ ID NO: 2)
CCGCAATTGTTAATTAAGGATCCCCATCATCAATAATATACCTTA,
and the 3'-end primer:
(SEQ ID NO: 3)
CCATCGATTTAAATAGATCTGCGGCCCTAGACAAATATTACGCGC were used.

The 5'-end primer contains the recognition sequences of respective restriction enzymes, i.e., caattg for MunI, TTAAT-TAA for PacI and ggatcc for BamHI.

The 3'-end primer contains the recognition sequences of respective restriction enzymes, i.e., ATCGAT for ClaI, ATT-TAAAT for SwaI and AGATCT for BglII.

Using the primers described above, PCR was performed using as a template genomic DNA of human type 5 adenoviral recombinant virus (pAx-FRGD virus (cf. Nakamura, et al., 2002, supra)) to obtain the 401 bp PCR fragment represented by SEQ ID NO: 4 and containing 357 bp from the left end of the adenovirus genome.

(SEQ ID NO: 4)
ccgcaattgTTAATTAAggatcccCATCATCAATAATATACCTTATTTTG

GATTGAAGCCAATATGATAATGAGGGGGTGGAGTTTGTGACGTGGCGCGG

GGCGTGGGAACGGGGCGGGTGACGTAGTAGTGTGGCGGAAGTGTGATGTT

GCAAGTGTGGCGGAACACATGTAAGCGACGGATGTGGCAAAAGTGACGTT

TTTGGTGTGCGCCGGTGTACACAGGAAGTGACAATTTTCGCGCGGTTTTA

GGCGGATGTTGTAGTAAATTTGGGCGTAACCGAGTAAGATTTGGCCATTT

TCGCGGGAAAACTGAATAAGAGGAAGTGAAATCTGAATAATTTTGTGTTA

CTCATAGCGCGTAATATTTGTCTAGGGCCGCagatctatttaaatcgat gg

The PCR fragment described above was digested with restriction enzymes MunI (MfeI) and ClaI. The resulting DNA fragment of about 400 bp was used to produce pWE357 PacI. Using plasmid pWE15 purchased from Clontech, Inc., the fragment above was incorporated into the EcoRI and ClaI sites (EcoRI and MunI generate the sticky end AATT and ligation is possible). The plasmid obtained was named pWE357 PacI.

Next, using the ClaI/EcoRI fragment containing about 24 kb of human type 5 adenovirus genome from pAx-FRGD (plasmid described in Nakamura et al., 2002, supra) and the EcoRI/RsrII fragment containing the 6.7 kb adenovirus genome corresponding to the FRGD fiber, the three fragments were ligated into ClaI/RsrII site of the plasmid pWE357 PacI (the ClaI/RsrII fragment containing 357 bp from the left end of the adenovirus genome) and the pAx3 plasmid was obtained. This name is short for pAx357.

The fiber of pAx3 plasmid is not wild type but FRGD-modified. The 166 bp in the HI loop region containing F/RGD mutation (CDCRGDCFC (SEQ ID NO: 32)) is as shown in SEQ ID NO: 5 and is contained in ligation with SacII (CD-CRGDCFC (SEQ ID NO: 32)), AseI, XhoI, BamHI, MluI and SalI as the restriction enzyme site.

(SEQ ID NO: 5)
TGTGACTGCCGCGGAGACTGTTTCTGCCCAAGTGCATACTCTATGTCATT

TTCATGGGACTGGTCTGGCCACAACTACATTAATGAAATATTTGCCACCT

CGAGTTACACTTTTTCATACATTGCCCAAGAATAAGGATCCACGCGTGTC

GACAAGAATAAAGAAT

B. Production of Plasmid Containing FZ33 Fiber Mutation
1) PCR in the HI loop
For the purpose of inserting a fragment with the Z33 motif in the HI loop of the human type 5 adenoviral fiber knob, a fragment containing the HI loop bearing the AgeI site (AC-CGGT) and the NheI site (GCTAGC) within the HI loop to facilitate cloning was artificially produced by PCR.
a) Production of the First Half of the hiAN Fragment Using primers #2091 and #2092 described below as the 5' prime and 3' primer, respectively, PCR was carried out using pWE6.7R-F/wt-2 (plasmid described in Nakamura et al., 2002, supra) as a template to produce the first half of the fragment. The fragment was digested with restriction enzymes KpnI and EcoRI to produce pSKII+hiAN.

The nucleotide sequences of primers #2091 and #2092 are as follows.

2091 (KpnI), 37b
(SEQ ID NO: 6)
cggggtaccaatatctggaacagttcaaagtgctcat

2092 (FZ33, AgeI), 47b
(SEQ ID NO: 7)
cggaattcggcgcgccaccggtttcctgtgtaccgtttagtgtaatg The nucleotide sequence of the product of 314 bp obtained by PCR above is represented by SEQ ID NO: 8.

(SEQ ID NO: 8)
cggggtaccaaTATCTGGAACAGTTCAAAGTGCTCATCTTATTATAAGAT

TTGACGAAAATGGAGTGCTACTAAACAATTCCTTCCTGGACCCAGAATAT

TGGAACTTTAGAAATGGAGATCTTACTGAAGGCACAGCCTATACAAACGC

TGTTGGATTTATGCCTAACCTATCAGCTTATCCAAAATCTCACGGTAAAA

CTGCCAAAAGTAACATTGTCAGTCAAGTTTACTTAAACGGAGACAAAACT

AAACCTGTAACACTAACCATTACACTAAACGGTACACAGGAAaccggtgg cgcgccgaattccg b) Production of the Second Half of the hiAN Fragment Using primers #2093 and #2068 described blow as the 5' primer and 3' primer, respectively, PCR was carried out using pWE6.7R-F/wt-2 (plasmid described in Yoshida et al., 1998, supra) as a template to produce the second half of the fragment. The fragment was digested with restriction enzymes EcoRI and BamHI to produce pSKII+hiAN.

The nucleotide sequences of primers #2093 and #2068 are as follows.

2093 (FZ33, NheI), 52b
(SEQ ID NO: 9)
ccgaattccgctagcgacacaactccaagtgcatactctatgtcattttc
at

2068 (26b)
(SEQ ID NO: 10)
atatggtaccgggaggtggtgaatta

The nucleotide sequence of the PCR product of 974 bp obtained by PCR above using #2093 and #2068 is represented by SEQ ID NO: 11.

(SEQ ID NO: 11)
ccgaattccgctagcgacacaactccaagtgcatactctatgtcattttc atGGGACTGGTCTGGCCACAACTACATTAATGAAATATTTGCCACCTCGA

GTTACACTTTTTCATACATTGCCCAAGAATAAGGATCCACGCGTGTCGAC

AAGAATAAAGAATCGTTTGTGTTATGTTTCAACGTGTTTATTTTTCAATT

GCAGAAAATTTCAAGTCATTTTTCATTCAGTAGTATAGCCCCACCACCAC

ATAGCTTATACAGATCACCGTACCTTAATCAAACTCACAGAACCCTAGTA

TTCAACCTGCCACCTCCCTCCCAACACACAGAGTACACAGTCCTTTCTCC

CCGGCTGGCCTTAAAAAGCATCATATCATGGGTAACAGACATATTCTTAG

GTGTTATATTCCACACGGTTTCCTGTCGAGCCAAACGCTCATCAGTGATA

TTAATAAACTCCCCGGGCAGCTCGCTTAAGTTCATGTCGCTGTCCAGCTG

CTGAGCCACAGGCTGCTGTCCAACTTGCGGTTGCTCAACGGGCGGCGAAG

GGGAAGTCCACGCCTACATGGGGGTAGAGTCATAATCGTGCATCAGGATA

GGGCGGTGGTGCTGCAGCAGCGCGCGAATAAACTGCTGCCGCCGCCGCTC

CGTCCTGCAGGAATACAACATGGCAGTGGTCTCCTCAGCGATGATTCGCA

CCGCCCGCAGCATGAGACGCCTTGTCCTCCGGGCACAGCAGCGCACCCTG

ATCTCACTTAAATCAGCACAGTAACTGCAGCACAGCACCACAATATTGTT

CAAAATCCCACAGTGCAAGGCGCTGTATCCAAAGCTCATGGCGGGACCA

CAGAACCCACGTGGCCATCATACCACAAGCGCAGGTAGATTAAGTGGCGA

CCCCTCATAAACACGCTGGACATAAACATTACCTCTTTTGGCATGTTGTA

ATTCACCACCTCCCGGTACCatat

The nucleotide sequence of the 136 bp fragment obtained by digesting the above fragment with EcoRI and BamHI is as shown below.

(SEQ ID NO: 12)
gaattccgctagcgacacaactccaagtgcatactctatgtcattttcat

GGGACTGGTCTGGCCACAACTACATTAATGAAATATTTGCCACCTCGAGT

TACACTTTTTCATACATTGCCCAAGAATAAGGATCC

2) Production of pSKII+hiAN Plasmid

Three fragments, namely, the first half fragment and second half fragment of the hiAN fragment obtained in 1) above and the fragment of about 3 kb obtained by digesting with KpnI and BamHI of pBluescriptII+® (cloning vector, Stratagene) followed by treatment with alkaline phosphatase CIAP (alkaline phosphatase derived from calf intestine, hereafter abbreviated as CIAP) were ligated to produce the pSKII+hiAN plasmid, cleotide sequence between KpnI and BamHI is as shown in SEQ ID NO: 13.

The length of the PCR fragment between KpnI and BamHI is about 439 bp. The confirmed nucleotide sequence between KpnI and BamHI is as shown in SEQ ID NO: 13.

(SEQ ID NO: 13)
ggtaccaaTATCTGGAACAGTTCAAAGTGCTCATCTTATTATAAGATTTG

ACGAAAATGGAGTGCTACTAAACAATTCCTTCCTGGACCCAGAATATTGG

AACTTTAGAAATGGAGATCTTACTGAAGGCACAGCCTATACAAACGCTGT

TGGATTTATGCCTAACCTATCAGCTTATCCAAAATCTCACGGTAAAACTG

CCAAAAGTAACATTGTCAGTCAAGTTTACTTAAACGGAGACAAAACTAAA

CCTGTAACACTAACCATTACACTAAACGGTACACAGGAAaccggtggcgc gccGAATTCcgctagcgacacaactccaagtgcatactctatgtcatttt catGGGACTGGTCTGGCCACAACTACATTAATGAAATATTTGCCACCTCG

AGTTACACTTTTTCATACATTGCCCAAGAATAAGGATCC

3) Production of pSKII+Z33 Plasmid

Using primers #2085 (48 base) and #2086 (48 base) as the 5' primer and 3' primer, respectively, PCR was carried out using synthetic oligonucleotide #2087 (86 base) as a template to obtain the Z33 motif-containing DNA fragment with the AgeI site and the NheI site at both ends as the PCR fragment of 132 bp. The digestion product of this Z33 motif fragment with restriction enzymes AgeI and NheI was cloned into the pSKII+hiAN plasmid between the AgeI site and the NheI site to confirm the nucleotide sequence. Thus, the pSKII+Z33 plasmid was obtained.

The nucleotide sequences of primers #2085 and #2086 and the template #2087 are given below.

2085 (Z33), 48b
(SEQ ID NO: 14)
gaaaccggtctcatcaagtttaacatgcagcagcagcgccgcttttac

2086 (Z33), 48b
(SEQ ID NO: 15)
gtcgctagcatctatgtcgtcgcgaatgctcttaatcttggcgttgcg

2087 (Z33), 86b
(SEQ ID NO: 16)
atgcagcagcagcgccgcttttacgaggccttgcacgacccaacctgaa
cgaggagcagcgcaacgccaagattaagagcattcg The nucleotide sequence of the above 132 bp fragment obtained by PCR is shown below.

(SEQ ID NO: 17)
GAAACCGGTCTCATCAAGTTTAACATGCAGCAGCAGCGCCGCTTTTACGA

GGCCTTGCACGACCCCAACCTGAACGAGGAGCAGCGCAACGCCAAGATT

AAGAGCATTCGCGACGACATAGATGCTAGCGAC

This is translated into the encoded amino acid sequence, as shown below.

(SEQ ID NO: 18)
ETGLIKFNMQQQRRFYEALHDPNLNEEQRNAKIKSIRDDIDASD

The nucleotide sequence of 538 bp from KpnI to BamHI containing the HI loop is shown below.

(SEQ ID NO: 19)
ggtaccaatatctggaacagttcaaagtgctcatcttattataagatttg acgaaaatggagtgctactaaacaattccttcctggacccagaatattgg aactttagaaatggagatcttactgaaggcacagcctatacaaacgctgt tggatttatgcctaacctatcagcttatccaaaatctcacggtaaaactg ccaaaagtaacattgtcagtcaagtttacttaaacggagacaaaactaaa cctgtaacactaaccattacactaaacggtacacaggaa<u>ACCGGT</u>CTCAT

CAAGTTTAACATGCAGCAGCAGCGCCGCTTTTACGAGGCCTTGCACGACC

CCAACCTGAACGAGGAGCAGCGCAACGCCAAGATTAAGAGCATTCGCGAC

GACATAGAT<u>GCTAGC</u>gacacaactccaagtgcatactctatgtcattttc atgggactggtctggccacaactacattaatgaaatatttgccacctcga gttacacttttttcatacattgcccaagaataaggatcc The underlined sequences are ACCGGT or the AgeI site and GCTAGC or the NheI site. The sequence indicated by capitals is the nucleotide sequence containing the sequence encoding Z33 produced by PCR.

The nucleotide sequence described above is translated into the amino acid sequence encoded by the same, which is shown below.

(SEQ ID NO: 20)
VPISGTVQSAHLIIRFDENGVLLNNSFLDPEYWNFRNGDLTEGTAYTNAV

GFMPNLSAYPKSHGKTAKSNIVSQVYLNGDKTKPVTLTITLNGTQ<u>ETGLI</u>

<u>KFNMQQQRRFYEALHDPNLNEEQRNAKIKSIRDDIDAS</u>DTTPSAYSMSFS

WDWSGHNYINEIFATSSYTFSYIAQE

The 33 amino acids shown by the underlined FNMQQQR-RFYEALHDPNLNEEQRNAKIKSIRDD (SEQ ID NO: 21) is the amino acid sequence of FZ33 reported. The additional underlined sequences are the amino acid sequences (TG and AS, respectively) encoded by ACCGGT or the AgeI site and GCTAGC or the NheI site, respectively.

4) Production of pWE6.7R-FZ33 Plasmid

Three fragments, namely, the fragment from XbaI to BstXI containing the region encoding the N-terminal portion of the fiber in the pWE6.7R-F/wt-2 plasmid, the fragment from BamHI to XbaI containing the region up to the right end of human type 5 adenovirus genome of the pWE6.7R-F/wt-2 plasmid and the fragment from BstXI to BamHI containing Z33 motif of the pSKII+Z33 plasmid were ligated to produce the pWE6.7R-FZ33 plasmid.

5) Production of pAx3-FZ33 Cosmid Plasmid

Three fragments, namely, the fragment containing 357 bp from the left end of human type 5 adenovirus genome from RsrII to ClaI of pAx3 (3956 bp fragment), the fragment of about 24 kbp corresponding to the central portion of human type 5 adenovirus from ClaI to EcoRI and the fragment from EcoRI to RsrII of pWE6.7R-FZ33 containing the right fiber portion of adenovirus genome were ligated to give the pAx3-FZ33 cosmid plasmid (about 35 kbp). FIG. 13-2 is a schematic representation of the plasmid.

6) Production of pAx3-CAZ3(L)-FZ33

Plasmid pCAZ3, which expresses beta-galactosidase, is a plasmid described in Nakamura et al, 2002 (supra). A fragment (about 5153 bp) that was obtained from the plasmid pCAZ3 by digesting beta-galactosidase expression cassette with restriction enzymes BamHI and BglII and then blunting the digested end with T4 DNA polymerase was cloned into the pAx3-FZ33 cosmid plasmid at the SwaI site (CIAP-treated). The one that transcription of the beta-galactosidase expression cassette was reverse to the direction of transcription of E1 genome in adenovirus, namely, in the leftward direction was selected and named pAx3-CAZ3(L)-FZ33.

7) Production of pAx3-CAEGFP(L)-FZ33 pCAEGFP was obtained as follows. pEGFP-N1 purchased from Clontech was used for the region encoding EGFP (enhanced green fluorescence protein) and digested with restriction enzyme NotI, blunted with T4 DNA polymerase at the digested end and then treated further with restriction enzyme EcoRI. The EGFP-containing fragment was ligated to DNA obtained by digesting the pCAcc plasmid described in Yoshida et al., 1998 (supra) with BglII, blunting the digested end with T4 DNA polymerase and then treated with restriction enzyme EcoRI. Thus, the pCAEGFP plasmid was obtained.

In addition, the EGFP expression cassette was digested with restriction enzyme ClaI and excised as the DNA fragment of about 2986 bp from pCAEGFP described above. The DNA fragment was ligated to the pAx3-FZ33 cosmid plasmid at its ClaI site (CIAP-treated). The one that transcription of the EGFP expression cassette was reverse to the direction of transcription of E1 genome in adenovirus, namely, in the leftward direction was selected and named pAx3-CAEGFP (L)-FZ33.

C. Production of Recombinant Adenovirus

Recombinant adenovirus Ax3-CAZ3(L)-FZ33 expressing beta-galactosidase and recombinant adenovirus Ax3-CAE-GFP(L)-FZ33 expressing EGFP were produced as follows, respectively.

The cosmid plasmids pAx3-CAZ3(L)-FZ33 and pAx3-CAEGFP(L)-FZ33 were digested with restriction enzyme PacI, respectively, and the resulting DNA was transfected to adenovirus producing cell HEK293 cells by the method already reported (Uchida, et al., Mol. Ther., 10(1):162-171, 2004) to obtain the recombinant adenovirus.

Specifically, for the generation of recombinant adenovirus, each cosmid was transfected into 293 cells by lipofection using Lipofectamine® 2000 Reagent (transfection reagent, Invitrogen) to produce recombinant adenovirus. Plaques arising from the transfected 293 cells were isolated and evaluated by restriction enzyme digestion of the viral genome and sequencing of the expression units. The resulting adenoviral vectors were expanded in 293 cells and purified by cesium chloride ultracentrifugation. Purified viruses were dialyzed in phosphate buffered saline (PBS) with 10% glycerol and stored at −70° C. until use. To determine the viral concentration (vp/ml), the viral solution was incubated in 0.1% sodium dodecyl sulfate (SDS) and $A_{260}$ was measured (C. Nyberg-Hoffman, et al., Sensitivity and reproducibility in adenoviral infectious titer determination. Nat. Med., 3 (1997), pp. 808-811). The concentration was determined as vp/ml=$A_{260}$×($1.1 \times 10^{12}$). Before use, contamination with replication-competent viruses in the viral stock was ruled out by PCR analysis using the following primers (W. W. Zhang, et al., Detection of wild-type contamination in a recombinant adenoviral preparation by PCR. Biotechniques, 18 (1995), pp. 444-447).

```
Primers specific to E1A:
Forward primer:
5'-ATTACCGAAGAAATGGCCGC-3',      (SEQ ID NO: 22)

Reverse primer:
5'-CCCATTTAACACGCCATGCA-3';      (SEQ ID NO: 23)

Primers specific to E1B:
Forward primer:
5'-CGGCTGCTGTTGCTTTTTTG-3',      (SEQ ID NO: 24)

Reverse primer:
5'-GTATCTTCATCGCTAGAGCC-3';      (SEQ ID NO: 25)

Primers specific to E2B (positive control):
Forward primer:
5'-TCGTTTCTCAGCAGCTGTTG-3',      (SEQ ID NO: 26)

Reverse primer:
5'-CATCTGAACTCAAAGCGTGG-3'       (SEQ ID NO: 27)
```

Adenoviral infection was performed basically according to the procedure described supra (H. Uchida, et al., 5-Fluouracil efficiently enhanced apoptosis induced by adenovirus-mediated transfer of caspase-8 in DLD-1 colon cancer cells. J. Gene Med., 5 (2003), pp. 287-299).

For the production of recombinant adenovirus Adv-FZ33 series, reference is appropriately made to the literatures cited herein.

Example 2

Construction of Monoclonal Antibody Library

BALB/c mice were immunized with the hamster cell line Has cells to construct a library of monoclonal antibodies against Has cells. More specifically, approximately a million of Has cells were intraperitoneally administered to BALB/c mice every 1 week or every 2 weeks 4 times or more. For final immunization (booster), mice were intravenously injected with the same amount of cells via the tail vein. Three days after the final booster immunization, cell fusion was performed using mouse myeloma cells (P3U1) and polyethylene glycol to generate hybridomas. All manipulations including procedures of cell fusion, selection of hybridomas in HAT selection media, subcloning of hybridomas, method of inducing ascites cancer in mice by intraperitoneal injection of hybridomas in mice, purification of mouse immunoglobulin from mouse ascites, etc. were all performed by the standard methods already reported (e.g., Hamada, H. and Tsuruo, T., PNAS, 83(20): 7785-9, 1986).

The procedures for purifying mouse immunoglobulin from mouse ascites are shown below.

(Purification of Antibodies)

(1) Recover the mouse ascites.
(2) Centrifuge at 1500 rpm for 5 minutes.
(3) Recover the supernatant.
(4) Centrifuge at 3000 rpm for 5 minutes.
(5) Recover the supernatant (about 10 ml).
(6) Filter the recovered supernatant through a filter (pore diameter: 0.45 µm).
(7) React the filtrate at room temperature for 30 minutes in a batch method using 1 ml of Protein G-Sepharose gel.
(8) Wash with 10 ml of binding buffer.
(9) Apply the washed gel to a column.
(10) Wash with 10 ml of binding buffer.
(11) Elute with 6 ml of elution buffer for recovery (1 ml of each fraction is recovered per 100 µl of 1M Tris buffer (pH 7.5)).
(12) Recover fractions shown $OD_{280}$=0.3 or more.
(13) Dialyze the recovered fractions to PBS overnight.
(14) Filter through a filter with a pore diameter of 0.22 µm.
(15) Measure $OD_{280}$ ($OD_{280}$ 1.5=1 mg/ml in IgG).

For constructing the library of monoclonal antibodies described above, reference is appropriately made to the literatures cited herein.

Example 3

Screening of Targeted Antibody

Staining and Chemiluminescence Assay of Beta-Galactosidase

The resulting antibody (hybridoma supernatant) was reacted with Has cells, which had been previously seeded in a 96-well plate, and then infected with FZ33 fiber-modified adenovirus Ax3CAZ3-FZ33 expressing LacZ as a reporter gene. After twenty four hours or 48 hours, expression was confirmed by chemiluminescent β-Gal reporter gene assay and overexpressed hybridomas were cloned. Subcloning was repeated twice and clones of the hybridomas obtained from two different clones were named S11 and T13, respectively. The S11 and T13 hybridomas were deposited on Apr. 8, 2005 with National Institute of Advanced Industrial Science and Technology, International Patent Organism Depositary (IPOD) under FERM P-20499 and FERM P-20498, respectively.

The procedures are described below more specifically.

(1) Day −1:
Has cells are seeded in a 96-well plate at $3 \times 10^3$ cells/well.
(2) Day 0:
The hybridoma supernatant is added to each well in 50 µl/well, followed by reacting at 4° C. for an hour.

The cells are washed twice with 100 μl/well of phosphate buffered saline (PBS(−)).

The cells are infected with Ax3CAZ-FZ33 particles at 3×10³/cell.

The cells are washed once with 100 μl/well of PBS(−).

The medium is exchanged [and cell culture (100 μl/well of DMEM supplemented with 10% fetal bovine serum (FBS)) is added] followed by incubation at 37° C. for 24 hours (or 48 hours).

(3) Day 1 or 2:

Chemiluminescent β-Gal reporter gene assay is performed. The assay was performed on Wallac 1420 ARVO (Perkin Elmer) using Galacto Light Plus Reporter Gene Assay System: (Roche:T1001). Hereinafter, the method for preparing antibodies using the antibodies and Adv-FX33 adenovirus described in EXAMPLES 2 and 3 is sometimes referred to as "the method for screening Adv-FZ33 of the present invention."

Example 4

Identification of Antigens for Antibody S11 and Antibody T13

The antigens for antibody 111 and antibody T13 were identified by the following procedures.
(1) The cells were analyzed by flow cytometry using a FACSCalibur (Becton Dickinson Co.) to determine which cells expressed the resulting antibody.
(2) After the cell surface was biotinylated, the cells were reacted with each antibody for immunoprecipitation. SDS-PAGE was performed followed by blotting onto a membrane using western blotting. The biotinylated protein was stained with anti-avidin HRP and the molecular weight of antigen was identified.
(3) Using about 1×10⁹ Has cells, immunoprecipitation was performed. After separation by SDS-PAGE, silver stain was performed for visualization and the objective antigen band corresponding to the molecular weight of the antigen described above was excised.
(4) The gel was trypsinized, desalted and analyzed by TOF and MS/MS, followed by database search for protein identification.

Hereinafter, the main procedures and results are described more specifically.
A. Flow Cytometry The cells were evaluated by flow cytometry using a FACSCalibur (Becton Dickinson Co.) to determine which cells expressed the resulting antibody. The cells were washed twice with PBS containing 0.1% bovine serum albumin (BSA). The cells were reacted with a monoclonal antibody such as S11 or T13, control mouse IgG1 or the like and then labeled with goat anti-mouse IgG antibody, as a secondary antibody, conjugated with fluorescein isothiocyanate. Mouse IgG1 (eBioscience, P3 strain) was used as an isotype-matched control. The results are shown in FIGS. 3-1, 3-2 and 3-3.

FIG. 3-1 indicates the results of FACS analysis showing the reactivities of S11 with various cell lines. Positive reactivities were observed in Has cells, a part of human pancreatic cancers AsPC1 and Miapaca2, a part of prostate cancers 22Rv1 and LNCap, and a part of human lung cancer LC-2/ad. Weakly positive reactivities were observed in PC3 prostate cancer and PDF (primary dermal fibroblast), PC14 lung cancer and RERF-LC-KJ lung cancer. The other cells were negative. Since the positive cells recognized by the S11 antibody were clearly distinguished from the negative cells which were not recognized by the S11 antibody, it was strongly supported that the sensitivity and specificity of the diagnosis using the S11 antibody with PAP2a as a marker were high and the specificity for the target therapy using the S11 antibody targeting PAP2a was high. As such, this EXAMPLE reveals that the antibodies and antigen molecules extremely optimized for target therapy, which are highly sensitive and specific as diagnostic markers, can be screened directly and rapidly by using the antibody screening method of the present invention. In the figures, Has is a hamster cell line; Miapaca2, Panc1, BxPC3 and AsPC1 are human pancreatic cancer cells; PC3, 22Rv1 and LNCap are human prostate cancer cells; Hs695T and A375 are human malignant melanoma cells; MKN74 and MKN45 are human gastric cancer cells; TTn is a human esophagus cancer cell, PDF is a human primary culture fibroblast, Hela is a human ovarian cancer cell; and LC-2/ad, PC14 and RERF-LC-KJ are human lung cancer cells (same as in the following figures).

FIG. 3-2 indicates the results of FACS analysis showing the reactivities of T13 with various cell lines. T13 showed entirely the same staining pattern as in S11. Positive reactivities were observed in Has cells, a part of pancreatic cancers AsPC1 and Miapaca2, a part of prostate cancers 22Rv1 and LNCap, and a part of human lung cancer LC-2/ad. Weakly positive reactivities were observed in PC3 prostate cancer, PDF (primary dermal fibroblast), PC14 lung cancer and RERF-LC-KJ lung cancer. The other cells were negative. Since the positive cells recognized by the T13 antibody were clearly distinguished from the negative cells which were not recognized by the T13 antibody, it was strongly supported that the sensitivity and specificity of the diagnosis using the T13 antibody with PAP2a as a marker were high and the specificity for the target therapy using the T13 antibody targeting PAP2a was high. As such, this EXAMPLE reveals that the antibodies and antigen molecules extremely optimized for target therapy, which are highly sensitive and specific as diagnostic markers, can be screened directly and rapidly by using the antibody screening method of the present invention.

FIG. 3-3 indicates the results of FACS analysis showing the reactivities of the S11 antibody with various cell lines. Positive reactivities were observed in human pancreatic cancer Miapaca2, prostate cancer 22Rv1, human lung cancer A549 and human ovarian cancer cell SK-OV-3. The reactivity was weakly positive in human ovarian cancer cell RMG-1 and negative in human breast cancer cell SK-Br-3. In the figure, Miapaca2 is a human pancreatic cancer cell, 22Rv1 is a human prostate cancer cell, A549 is a human lung cancer cell, RMG-1 is a human ovarian cancer cell, SK-OV-3 is a human ovarian cancer cell and SK-Br-3 is a human breast cancer cell (same as in the following figures).

FIG. 3-4 indicates the results of FACS analysis showing the reactivities of the T13 antibody with various cell lines. The T13 antibody showed entirely the same staining pattern as in the S11 antibody shown in FIG. 3-3. That is, positive reactivities were observed in human pancreatic cancer Miapaca2, prostate cancer 22Rv1, human lung cancer A549 and human ovarian cancer cell SK-OV-3. The reactivity was weakly positive in human ovarian cancer cell RMG-1 and negative in human breast cancer cell SK-Br-3.

B. Biotinylation of Cell Surface Protein

The protein on the Has cell surface was biotinylated by the following procedures. For 1×10⁷ cells, 1.5 mg of EZ-Link® Sulfo-NHS-Biotin (Reagent for modification of molecules, PIERCE, Inc., Product No. 21217) was used in 15 ml of PBS(−). A mixture of the cells and biotin was reacted at room temperature for 30 minutes and then washed with 100 mM glycine PBS(−) to stop the reaction.

C. Immunoprecipitation

The biotinylated Has cells, 11×10$^7$, were recovered and washed with ice-cold phosphate buffered saline (PBS(−)). Finally, the cells were recovered by centrifugation in a 50 ml tube. Next, the cells were suspended in 20 ml of ice-cold lysis buffer (1% NP40, 50 mM Tris-HCl, pH 7.6, 150 mM NaCl; Complete EDTA-free (Roche: Catalog No. 11 873 580 001) was used as a protease inhibitor cocktail). The suspension was allowed to stand on ice for an hour for solubilization. Subsequently, the cell-visualized solution was centrifuged at 4° C. for 30 minutes at 15000 rpm (×17360 g) using a centrifugal machine (TOMY:MX-150: Rotar TMP-11), and the supernatant was transferred to a new 50 ml tube. After 1 ml of 50% (v/v) Protein G Sepharose® 4 Fast Flow (chromatographic medium, Amersham Biosciences: Code No. 17-0618-02) was added to the supernatant, the tube charged with this solution was fixed into a rotary shaker and rotated and stirred at 4° C. for 2 hours. Centrifugation was performed with a centrifugal machine (KUBOTA:8900: Rotar RS-3010M) at 1500 rpm (470×g) and 4° C. for 5 minutes, and the supernatant was transferred to a new 15 ml tube by 6 ml each.

Next, 5 μg each of the S11 antibody (IgG1k), the T13 antibody (IgG1k) and Mouse IgG1k Isotype Control (eBioscience: Clone P3: #16-4714-85) as a control antibody were added to the supernatant, followed by reacting them at 4° C. for an hour. To the solution mixture, 50 μl of 50% (v/v) Protein G Sepharose® 4 Fast Flow was added. The tube was fixed on a rotary shaker and rotated at 4° C. for an hour for agitation. Then, the above solution mixture was centrifuged at 5700 rpm (2500×g) and 4° C. for a minute using a centrifugal machine (TOMY:MX-150: Rotar TMP-11) to remove the supernatant.

After 10 ml of ice-cold lysis buffer was added and stirred, Sepharose® beads were precipitated by a centrifugal machine and the supernatant was removed. This washing operation was repeated 6 times.

To the beads collected by centrifugation 25 μl of (×1) SDS sample buffer-5% 2ME was added, and the mixture was heat-treated for 5 minutes on a heat block heated to 100° C. After centrifuging at 5700 rpm (2500×g) and 4° C. for a minute on a centrifugal machine (TOMY:MX-150: Rotar TMP-11), the supernatant was used as a sample for immunoprecipitation.

D. SDS-PAGE

Using the aforesaid sample for immunoprecipitation, SDS-PAGE was carried out. Mini-PROTEAN 3 Cell® (electrophoresis apparatus, Bio-Rad: Catalog No. 163-3301) was used as an electrophoretic tank. Ready Gels J® (precast electrophoretic gel, Bio-Rad: Catalog No. 161-J371) was used as a polyacrylamide gel (5-20% gradient). Precision Plus Protein Standards Dual Color (Bio-Rad: Catalog No. 161-0374) was used as a molecular weight marker. Electrophoresis was performed at a constant current of 20 mA for 50 minutes.

E. Silver Stain

Silver stain MS Kit (Wako: Code No. 299-58901) was used.

FIG. 4 is electrophoresis pictures showing the results of western blotting and silver stain of the sample for immunoprecipitation. S11 and T13 were found to exhibit the same patterns. Two bands were observed at 30 kDa and 37 kDa, which are the antibodies recognized by the antibodies. In the bands immunoprecipitated by S11, the band of about 30 kDa was used for mass spectrometry.

F. Mass Spectrometry and Homology Search

Mass spectrometry and homology search were outsourced to Hitachi Science Systems.

Briefly explaining, the bands from the western blots described above were cut out, digested with trypsin, desalted and provided for TOF and MS/MS measurements and database search.

The models used for mass spectrometry and database search, software for search and database are as follows.

Mass spectrometer: MULDI-Qq-TOF MS/MS QSTAR® Pulsar I (Mass Spectometer, Applied Biosystems)
Software for database search: MASCOT
Database: NCBInr (Human)

FIG. 5 shows the results of mass spectrometry. The amino acid sequences of two peptide fragments clarified by the mass spectrometry were subjected to homology search on the database and found to coincide with a part of the amino acid sequence of human PAP2a (the hit sequences in the homology search are underlined in FIG. 5). The results reveal that the antigen against S11 and T13 is highly likely to be PAP2a.

Example 5

Identification of Antigen: Run 1 for Confirmation of Results of Mass Spectrometry and Homology Search A. Preparation of Sample for Immunoprecipitation The biotinylated Has cells, 7×10$^7$, were recovered and washed with ice-cold phosphate buffered saline (PBS(−)). Finally, the cells were collected by centrifugation in a 15 ml tube. Next, the cells were suspended in 3.5 ml of ice-cold lysis buffer (1% NP40, 50 mM Tris-HCl, pH 7.6, 150 mM NaCl; Complete EDTA-free (Roche: Catalog No. 11 873 580 001) was used as a protease inhibitor cocktail). The suspension was allowed to stand on ice for 30 minutes for solubilization. Next, the cell-visualized solution was centrifuged at 15000 rpm (x 17360 g) and 4° C. for 30 minutes using a centrifugal machine (TOMY: MX-150: Rotar TMP-11), and the supernatant was transferred to a new 15 ml tube. A portion (100 μl) of the cell-visualized solution was taken from the supernatant (supernatant A) and 50 μl of (×3) SDS sample buffer-15% 2-mercaptoethanol (2ME) was added thereto, which was used as a whole cell lysate sample. To the remaining supernatant A, 200 μl of 50% (v/v) Protein G Sepharose® 4 Fast Flow (Amersham Biosciences: Code No. 17-0618-02) was added. The tube charged with the sample described above was fixed into a rotary shaker and rotated and stirred at 4° C. for 2 hours. Centrifugation was performed with a centrifugal machine (KUBOTA:8900: Rotar RS-3010M) at 1500 rpm (470×g) and 4° C. for 5 minutes, and the supernatant was transferred to a new 1.5 ml tube by 500 μl each. To the supernatant, 5 μg of each antibody below was added:
  anti-PAP2a antibody (rabbit polyclonal antibody)
  anti-PAP2b antibody (rabbit polyclonal antibody)
  S11 antibody (IgG$_{1k}$)
  T13 antibody (IgG$_{1k}$), and,
as control antibodies:
  mouse IgG$_{1k}$ isotype control (eBioscience:CloneP3:#16-4714-85), and
  normal rabbit serum (DAKO: Code No. X0902).

The reaction was carried out at 4° C. for an hour. To each solution, 40 μl of 50% (v/v) Protein G Sepharose® 4 Fast Flow was added. The tube was fixed on a rotary shaker and rotated and agitated at 4° C. for an hour. After centrifuging a centrifugal machine (TOMY: MX-150: Rotar TMP-11) at 5700 rpm (2500×g) and 4° C. for 1 minute, the supernatant was removed.

After 1 ml of ice-cold lysis buffer was added and stirred, Sepharose beads were precipitated by a centrifugal machine and the supernatant was removed. This washing operation was repeated 6 times.

To the beads collected by centrifugation 20 μl of (×1) SDS sample buffer-5% 2ME was added, and the mixture was heat-treated for 5 minutes on a heat block heated to 100° C. After centrifuging at 5700 rpm (2500×g) and 4° C. for a minute on a centrifugal machine (TOMY:MX-150: Rotar TMP-11), the supernatant was used as a sample for immunoprecipitation/SDS-PAGE analysis.

B. SDS-PAGE

Using the aforesaid sample for immunoprecipitation, SDS-PAGE was performed. Mini-PROTEAN® 3 cell (Bio-Rad: Catalog No. 163-3301) was used as an electrophoretic tank. Ready Gels J® (Bio-Rad: Catalog No. 161-J371) was used as a polyacrylamide gel (5-20% gradient). Precision Plus Protein Standards Dual Color (Bio-Rad: Catalog No. 161-0374) was used as a molecular weight marker. Electrophoresis was performed at a constant current of 20 mA for 50 minutes.

C. Immunoblotting Assay (Western Blot Assay)

Immunoblotting by western blot assay was performed in a conventional manner using the following materials.

Semi-dry transfer apparatus (ADVANTEC: EB-150)
PVDF membrane Immobilon® P (0.45 μm) (Millipore: IPVH20200)
Transfer at a constant current of 100 mA for 60 minutes.
Blocking was carried out in the following solution.
Blocking solution (5% skimmed milk/PBS-0.05% Tween 20), room temperature, 2 hours The primary antibody reaction was carried out at 4° C. overnight on a shaker using the following antibodies:
anti-PAP2a antibody (1 μg/ml-blocking solution) and
anti-PAP2b antibody (1 μg/ml-blocking solution).

The secondary antibody reaction was carried out using:
anti-rabbit Ig, horseradish peroxidase linked F(ab')$_2$ fragment (Amersham Bioscience: Code No. NA9340).

Detection by chemiluminescence was performed using the following reagent.
ECL Western Blotting Detection Reagents (Amersham Bioscience: Code No. RPN2106).

Figure 6:
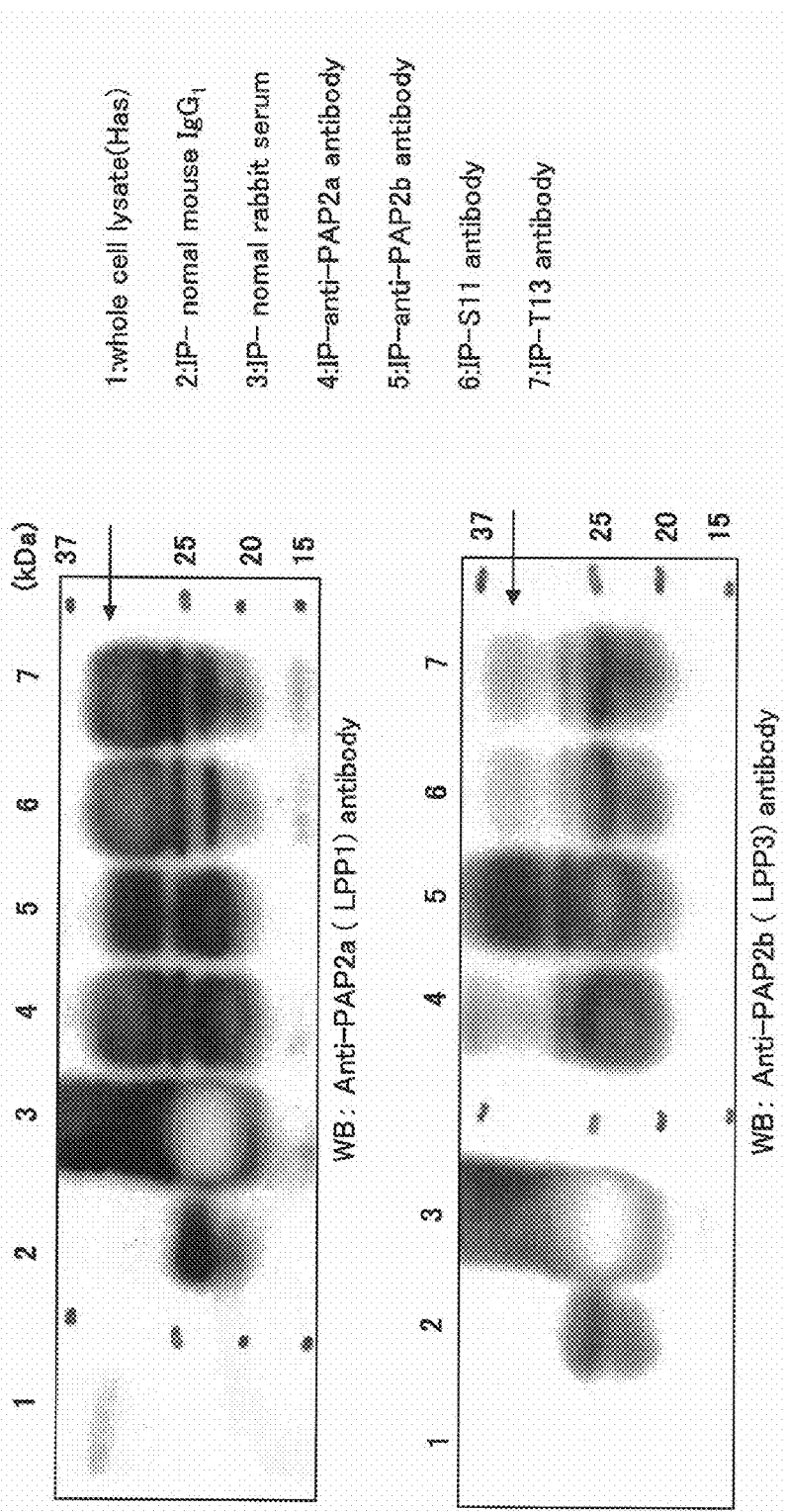
FIG. 6 shows electrophoretic photographs showing the western blots to confirm the results of mass spectrometry.

The results are shown in FIG. 6. Immunoprecipitation was performed by each antibody followed by immunoblotting analysis with anti-PAP2a polyclonal antibody (upper column) and anti-PAP2b polyclonal antibody (lower column), respectively. These polyclonal antibodies are rabbit antisera provided by Professor Hideo Kano, Second Department of Biochemistry, Sapporo Medical University.

Upper column: the anti-PAP2a polyclonal antibody was reacted with 4, 6 and 7.

Lower column: the anti-PAP2b polyclonal antibody was reacted only with 5.

In other words, the band of about 30 kDa, which was concentrated by S11 and T13 and immunoprecipitated, reacted with the anti-PAP2a polyclonal antibody. It was confirmed by the results that the antigen recognized by the S11 and T13 antibodies is PAP2a.

Example 6

Identification of Antigen: Run 2 for Confirming the Results of Mass Spectrometry and Homology Search A. Flow Cytometry Plasmids expressing PAP2a (LPP1), PAP2b (LPP3) and PAP2c (LPP2), respectively, were transfected into CHO cells, respectively, to examine by flow cytometry with which isoform the S11 antibody and the T13 antibody are reactive.

CHO cells (derived from Chinese hamster ovary) were seeded in a 6-well Microplate (IWAKI:3810-006) at $5 \times 10^5$. On the following day, the following plasmids were transfected into CHO cells using LipofectAMINE PLUS® Reagent (transfection reagent, Invitrogen:11514-015), respectively.

phPAP2aYFP
phPAP2bYFP
phPAP2cYFP

Forty eight hours after the gene delivery, the medium was removed from the well and each cell was suspended and recovered in Trypsin-EDTA solution (SIGMA: T3924). The cells were then washed with phosphate buffered saline (PBS (−)). Next, the CHO cells transfected with each gene was adjusted to $3 \times 10^5/100$ μl/1.5 ml tube, and 1 μg each of the S11 antibody and the T13 antibody was added as a primary antibody, followed by reacting on ice for 30 minutes. Mouse IgG1k Isotype Control (eBIOSCIENCE, P3 strain) was used as a control antibody.

After the reaction, centrifugation was performed at 2500 rpm (400×g) for 5 minutes using a centrifugal machine (TOMY: MX-150: Rotar TMP-11). After the supernatant was removed, the cell pellets were suspended and washed with 1 ml of PBS(−) and again centrifuged at 2500 rpm (400×g) for 5 minutes. This operation was repeated twice.

After washing the cells, the respective cells were suspended in 100 μl of PBS(−) and 0.5 μg of anti-mouse immunoglobulins/RPE (phycoerythrin) goat F(ab')$_2$ (DAKO: R 0480) was added thereto as a secondary antibody. The mixture was reacted on ice for 30 minutes. After the reaction, centrifugation was performed at 2500 rpm (×500 g) for 5 minutes with a centrifugal machine (TOMY: MX-150: Rotar TMP-11). After the supernatant was removed, the cell pellets were suspended and washed with 1 ml of PBS(−), followed by centrifugation again at 2500 rpm (500×g) for 5 minutes. This operation was repeated twice.

After washing the cells, the cells were suspended in 500 μl of PBS(−) and the suspension was transferred to a 5 ml polystyrene round tube (Becton Dickinson: 35 2235) with a cell strainer cap. Each sample adjusted was analyzed by a FACSCalibur (BD Bioscience). The results are shown in FIGS. 7-1 and 7-2.

Figures 1, 7:
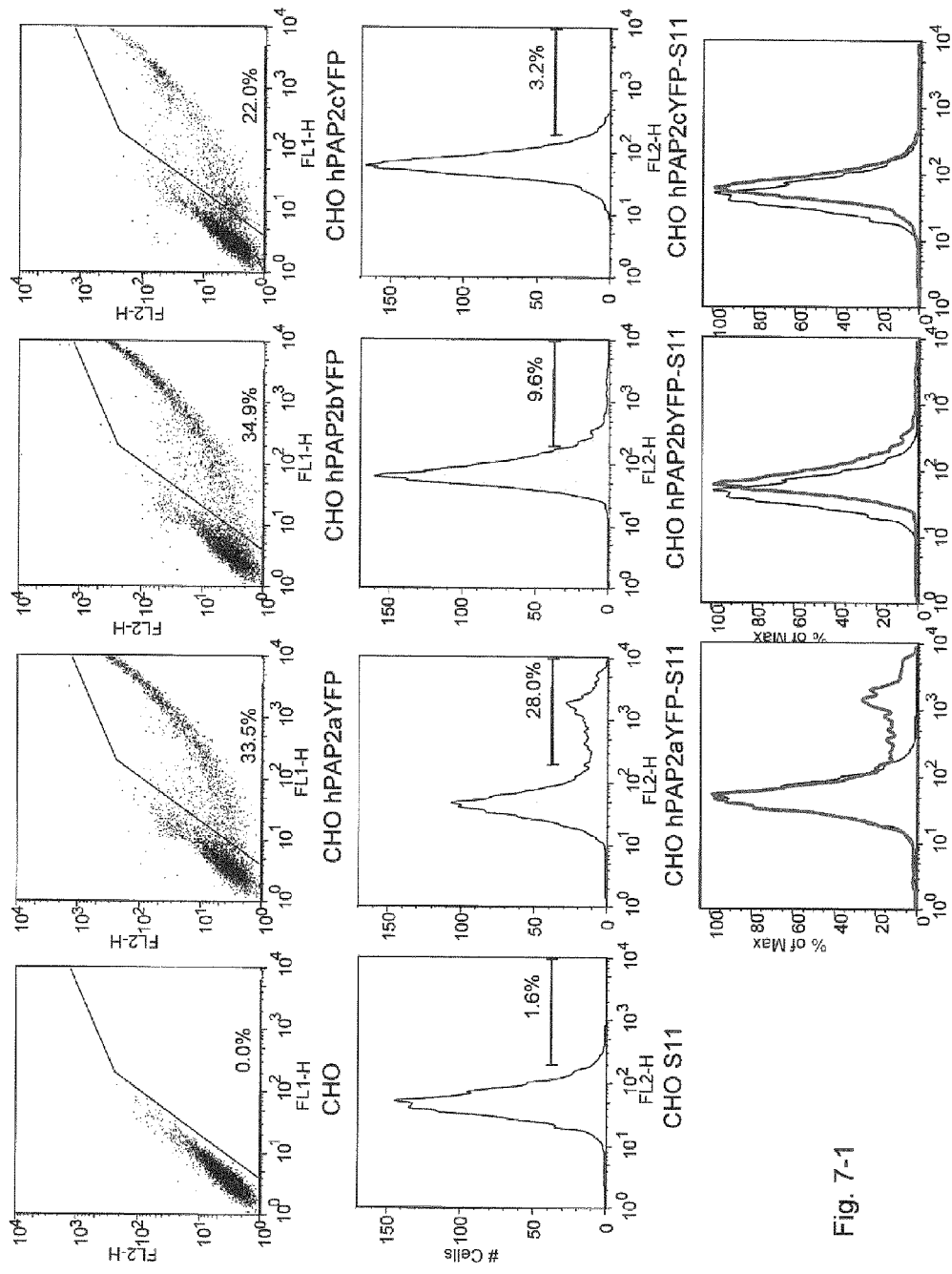
Figures 2, 7:
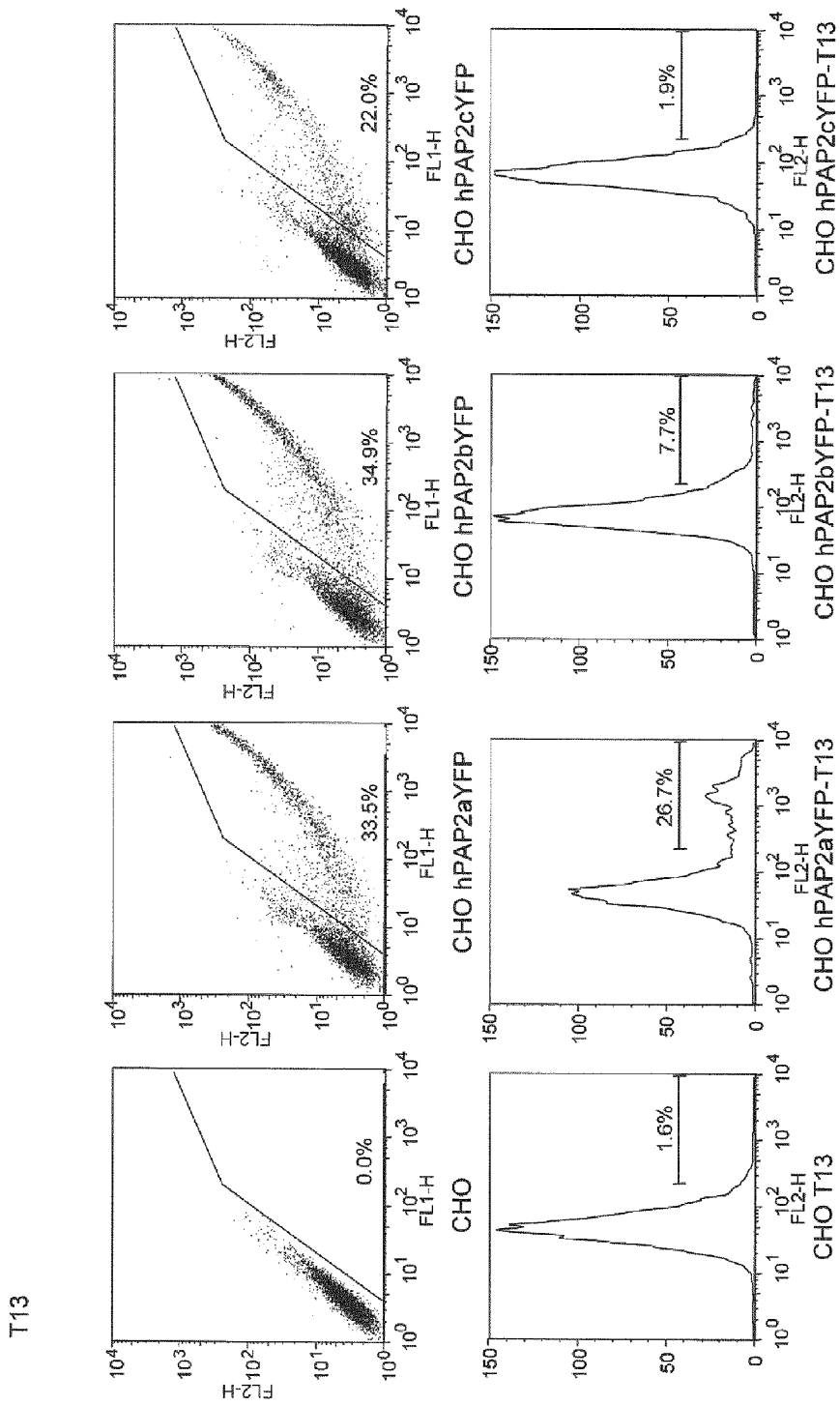

FIG. 7-1 is graphs showing the results that plasmids expressing PAP2a (LPP1), PAP2b (LPP3) and PAP2c (LPP2), respectively, were transfected and examined by flow cytometry to determine which isoform of PAP the S11 antibody reacted with.

The upper column indicates a transfection efficiency of each plasmid. The middle column shows the results of FACS analysis on each transfectant using S11. The lower column indicates that in the data at the middle column the data (the leftmost in the middle column) for control (CHO cells without plasmid transfection) were superimposed on the data of each transfectant. It was demonstrated that only the cells transfected with the plasmid expressing PAP2a-encoding cDNA acquired the reactivity with the S11 antibody. It was confirmed by the results that the antigen against the S11 antibody was PAP2a.

FIG. 7-2 is graphs showing the results that plasmids expressing PAP2a (LPP1), PAP2b (LPP3) and PAP2c (LPP2), respectively, were transfected and examined by flow cytometry, with which isoform of PAP the T13 antibody reacted. The upper column indicates a transfection efficiency of each plasmid. The lower column indicates the results that FACS analysis was performed on each transfectant using T13. It was demonstrated that only the cells transfected with the plasmid expressing PAP2a-encoding cDNA acquired the reactivity with the T13 antibody. It was confirmed thereby that the antigen against the T13 antibody was PAP2a.

B. Immunohistochemical Staining (Fluorescence Staining and Confocal Laser Scanning Microscopic Observation)

PAP2a (S11:IgG1) and Alexa Fluor488-Goat Anti-Mouse IgG (Invitrogen (MolecularProbes: A-11029) were used as primary and secondary antibodies, respectively. Has cells were seeded in a 2-well CultureSlide (Becton Dickinson: Catalog No. 354112) at $1 \times 10^4$ cells/well. On the following day, the cells were washed twice with PBS(−) and then fixed in each fixing solution described below for a given period of time.

4% Paraformaldehyde, room temperature, 30 mins.

10% Formalin neutral buffer solution, room temperature, 30 mins.

Next, after the CultureSlide described above was washed twice with PBS(−), the cells were incubated at room temperature for 5 minutes with 0.1% Triton X (PBS(−)) and then incubated at room temperature for 30 minutes with 10% normal goat serum (hereinafter referred to as "NGS") in PBS(−).

Next, to react with the primary antibody, the CultureSlide described above was incubated in NGS with 5 μg/ml of anti-PAP2a antibody S11 or control mouse IgG1 (P3 strain) at room temperature for 30 minutes, followed by washing 3 times with PBS(−). Next, to react with the secondary antibody, the CultureSlide described above was incubated with 5 μg/ml of Alexa Fluor488-Goat Anti-Mouse IgG (Invitrogen (Molecular Probes: A-11029) in NGS at room temperature for 30 minutes, followed by washing 3 times with PBS(−).

Next, the CultureSlide was nuclear counterstained and mounted with DAPI (4,6-diamidino-2-phenylindole) in VECTASHIELD® (chemical mixture for the retardance of photobleaching of fluorochromes in laboratory use, VECTOR: H-1200), which was observed by an upright confocal microscope BIORAD/R2100AG2. The results are shown in FIGS. 8 and 9.

FIG. 8 shows photographs of immunohistochemical staining by anti-PAP2a antibody S11. The photograph at the upper row in FIG. 8 indicates staining with S11 and the photograph at the lower row indicates staining with control mouse IgG1 (P3 strain). The figure reveals that Has cells 22Rv1 is PAP2a-positive. As such, the S11 antibody can stain the PAP2a-positive cells by tissue staining.

FIG. 9 shows photographs of immunohistochemical staining showing the state of PAP2a expression in Has cells using various fixation techniques. The photograph at the upper row in FIG. 9 indicates staining with S11 and the photograph at the lower row shows staining with control mouse IgG1. These photographs indicate that when S11 was used, PAP2a could be stained, respectively, even when fixed in paraformaldehyde, 10% formalin, etc. Similar results were obtained also when the T13 antibody was used.

C. Chemiluminescent β-Gal Reporter Gene Assay

FIG. 10 is graphs showing the multiplicity of infection of Ax3CAZ3-FZ33 on Has cells when Has cells were infected with Ax3CAZ3-FZ33, as the results of chemiluminescent β-Gal reporter gene assay. This run was performed by the procedures shown below.

(1) Dispense Has cells at a concentration of $1 \times 10^4$ cells/ 100 μl/well onto a 96-well microtiter plate (IWAKI).

(2) Incubate at 37° C. for 24 hours.

(3) Remove the culture medium.

(4) Wash once with 200 μl of PBS(−).

(5) Add the S11 or T13 antibody to PBS(−) at 0.1 μg/well/ 100 μl and incubate at 4° C. for an hour.

(6) Wash once with 200 μl of PBS(−).

(7) Infect with Ax3CAZ3-FZ33 (1000 vp/cell).

(8) Incubate at 4° C. for an hour.

(9) Wash twice in PBS(−).

(10) Add 100 μl/well of the culture medium (10% FBS-containing DMEM).

(11) Incubate at 37° C. for 24 hours.

Using the sample described above, chemiluminescent β-Gal reporter gene assay was performed using Galacto Light Plus Reporter Gene Assay System: (Roche: Code No. T1011). The assay was carried out in Wallac 1420 ARVO (Perkin Elmer). The protein level in each sample was measured using a BCA Protein Assay Kit (PIERCE: 23227).

In FIG. 10, NT denotes non-treatment, Ad denotes when Ax3CAZ3-FZ33 adenovirus alone was used, IgG1 denotes when control mouse IgG1 was used as an antibody, and S11 and T13 denote when the S11 and T13 monoclonal antibodies were used as antibodies, respectively. As shown in FIG. 10, when gene transfer of LacZ reporter by FZ33 adenovirus was performed using the S11 antibody or the T13 antibody, the transgene expression of LacZ reporter was as very high as about 70-fold, when compared with control (adenovirus alone Ad, control IgG1 added). The results reveal that the S11 and T13 antibodies are useful for gene delivery using adenoviral vector.

Figures 1A, 11:
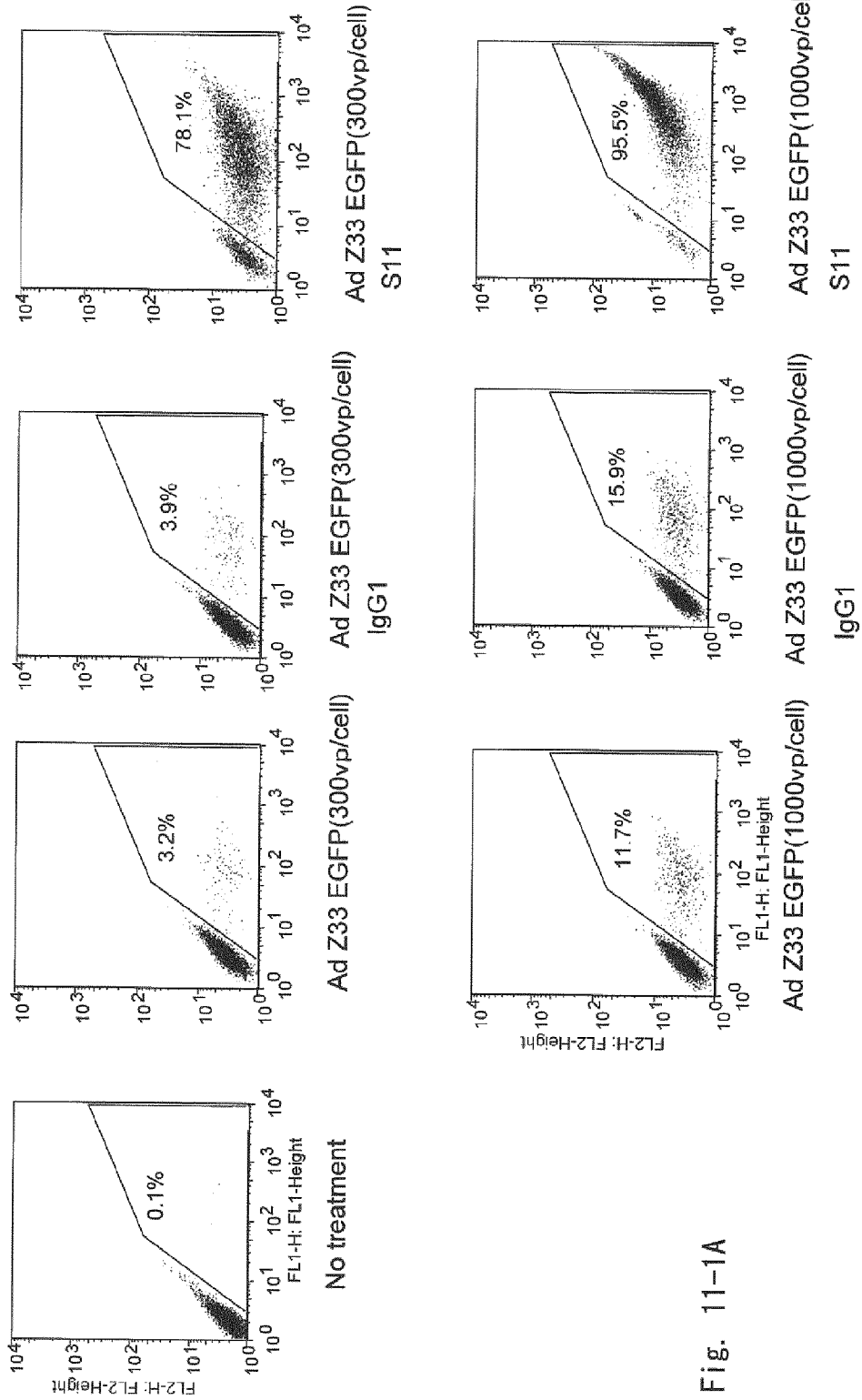
FIG. 11-1A is graphs showing the results of flow cytometry analysis of the EGFP fluorescent reporter gene expression assay for the multiplicity of infection of Ax3CAZ3-FZ33 on Has cells, when the cells were not previously treated using the antibody (second row from the left), when treated with IgG1 (third row from the left) and when treated with S11 (fourth row from the left), after Has cells were infected with Ax3CAEGFP-FZ33 at vector doses of 300 viral particles (vp)/cell and 1000 vp/cell thereby to express EGFP.

FIG. 11-1A is graphs showing the results of chemiluminescent β-Gal reporter gene expression assay for the multiplicity of infection of Ax3CAZ3-FZ33 on Has cells, when the cells were not previously treated using the antibody (second row from the left), when treated with IgG1 (third row from the left) and when treated with S11 (fourth row from the left), after Has cells were infected with Ax3CAZ3-FZ33 at vector doses of 300 viral particles (vp)/cell and 1000 vp/cell thereby to express EGFP. As illustrated, in 300 vp/cell, infection was 78.1% when S11 was used, whereas when control mouse IgG1 was used, the infection was observed only by 3.9%. Likewise, in 1000 vp/cell, the infection was observed by 95.5% when S11 was used, whereas the infection was only 15.9% when control mouse IgG1 was used.

The results indicate that when gene delivery by FZ33 adenovirus was performed using the S11 antibody, extremely high transgene expression efficiency of EGFP was obtained, as compared to control (adenovirus alone Ad, control IgG1 added).

Figures 1B, 11:
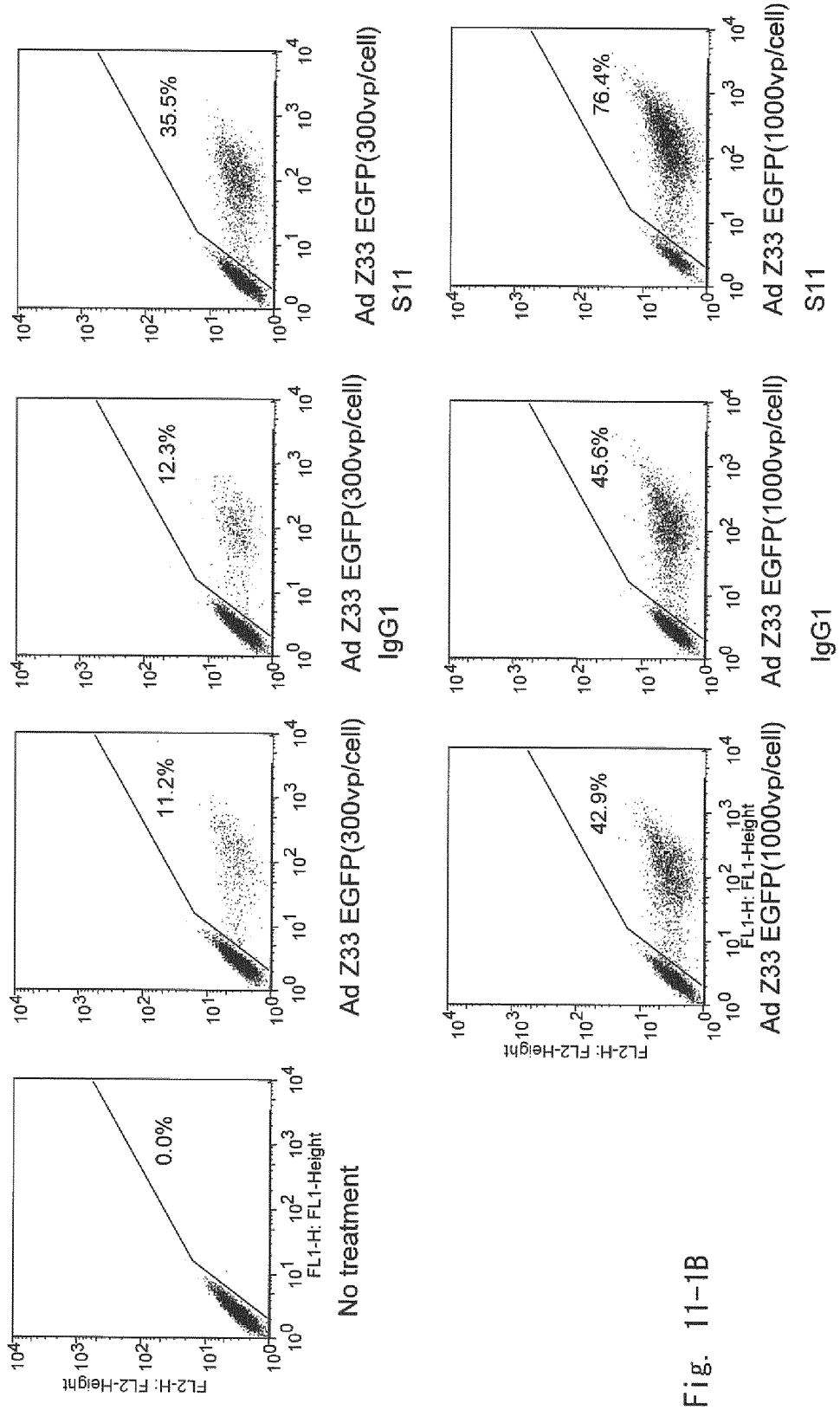

FIG. 11-1B is graphs showing the results of multiplicity of infection of adenoviral vectors against pancreatic cancer cell Miapaca2, when evaluated by flow cytometry using EGFP-expressing Ax3CAZ3-FZ33, as in FIG. 11-1A. As illustrated, in Miapaca2 previously treated with control mouse IgG1, the infection shown was 12.3% at a vector dose of 300 vp/cell and the multiplicity of infection was 45.6% at a vector dose of 1000 vp/cell, whereas in Miapaca2 previously treated with S11, the multiplicity of infection enhanced to 35.5% and 76.5% was exhibited at vector doses of 300 vp/cell and 1000 vp/cell, respectively.

Based on these results, when gene transfer by FZ33 adenovirus is performed using the S11 antibody, high enhanced gene delivery/expression efficiency of EGFP is obtained, as compared to control (adenovirus alone Ad, control IgG1 added).

Figures 1C, 11:
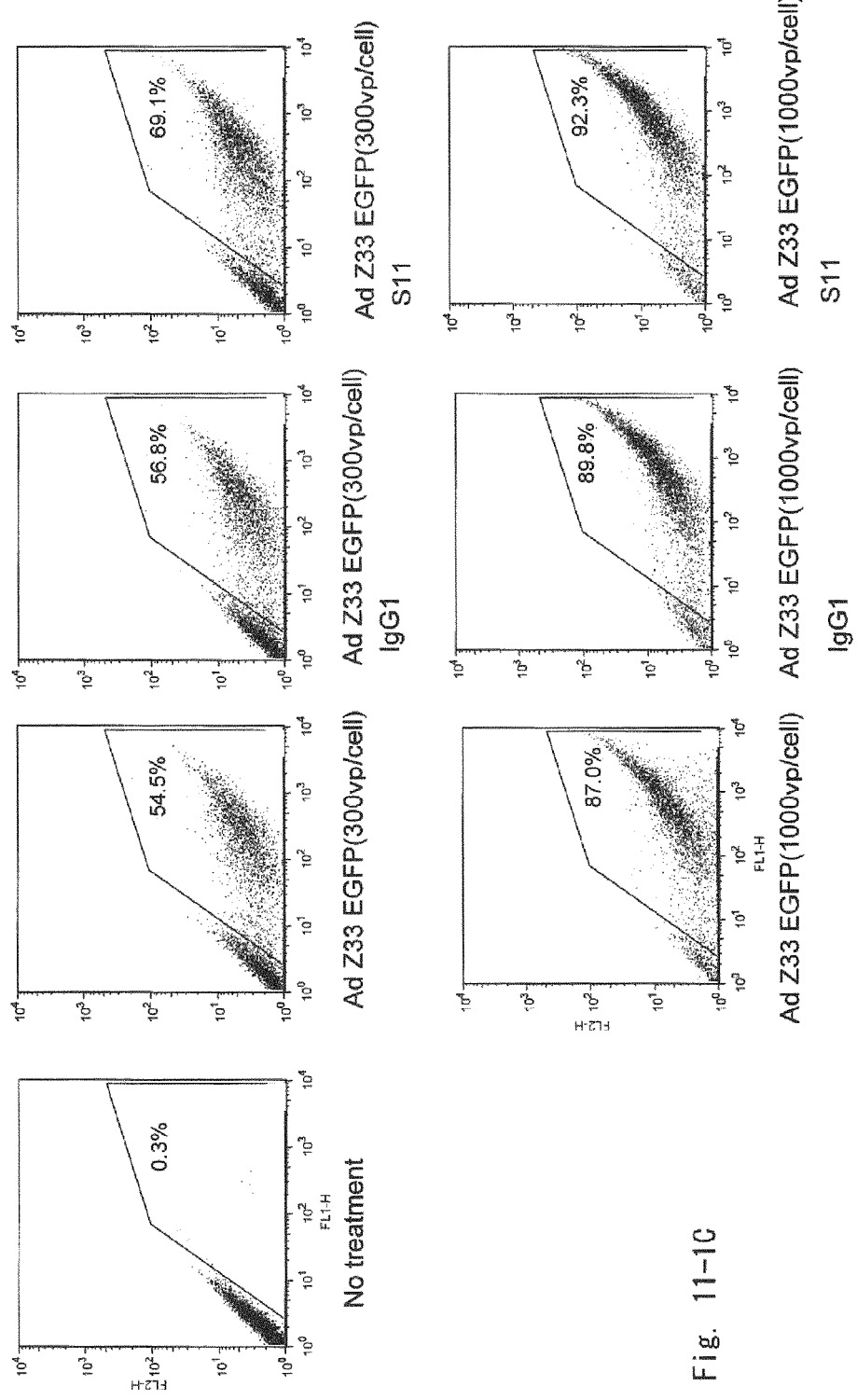

FIG. 11-1C is graphs obtained from flow cytometry runs, which demonstrate the multiplicity of infection of Ax3CAZ3-FZ33 on human prostate cancer cell 22Rv1 by comparison between when the cells were pre-treated with S11 and when the cells were pre-treated with control mouse IgG1. As illustrated, in 22Rv1 previously treated with control mouse IgG1, the infection shown was 56.8% and 89.8%, respectively, at vector doses of 300 vp/cell and 1000 vp/cell, whereas in 22Rv1 previously treated with S11, the infection shown was 69.1% and 92.3%, respectively, at vector doses of 300 vp/cell and 1000 vp/cell. As such, the multiplicity of infection of Ax3CAZ3-F33 on 22Rv1 were both high when previously treated with control mouse IgG1 and when previously treated with S11 but no substantial difference was found between them. In other words, it was speculated that particularly remarkable increase in multiplicity of infection would not be obtained with cells like prostate cancer 22Rv1, which originally has high transgene expression efficiency by adenovirus.

Figures 1D, 11:
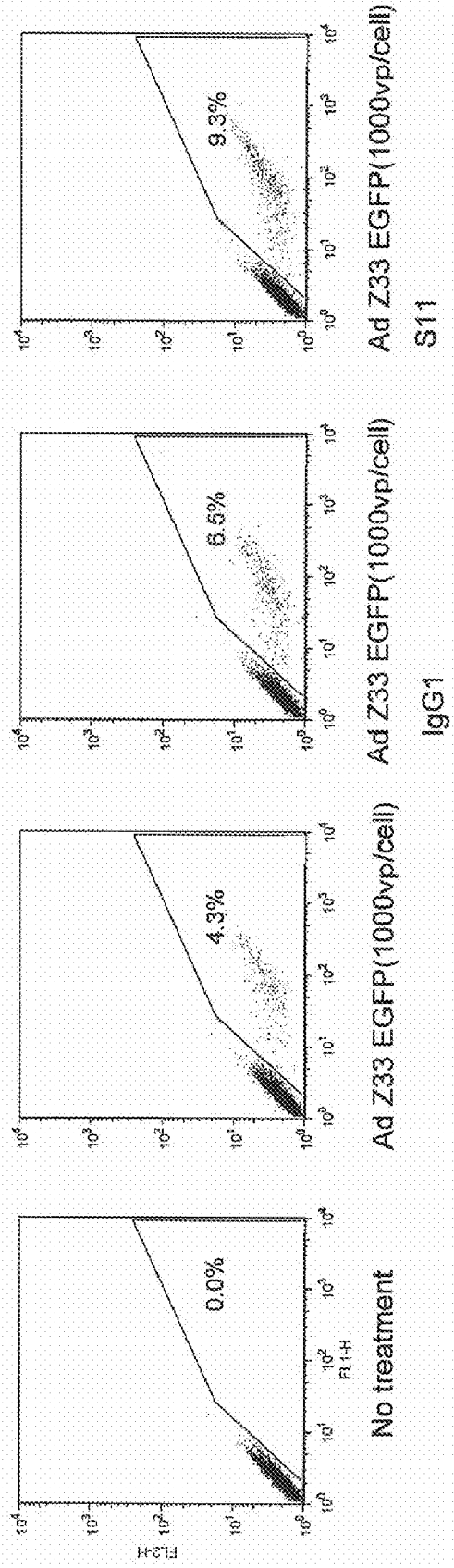

FIG. 11-1D is graphs showing the results obtained from flow cytometry runs by comparing the multiplicity of infection of Ax3CAZ3-F33 on another human prostate cancer cell PC3, between when the cells were pre-treated with control mouse IgG1 and when the cells were pre-treated with S11. As illustrated, the results obtained indicate that any significant change in the multiplicity of infection on PC3 was not observed either when control mouse IgG1 was used (third row from the left; 6.5%) or when S11 was used (fourth row from the left; 9.3%), as compared to the case where the cells were not pre-treated with the antibody (second row from the left; 4.3%). As such, even when gene transfer by FZ33 adenovirus is performed using the S11 antibody, significantly high transgene expression efficiency of EGFP is not obtained with the cells weakly positive or negative to PAP2a such as the prostate cancer PC3, when compared to control (adenovirus alone Ad, control IgG1 added). In other words, this means that selectivity of this antibody is high and it is expected that normal cells weakly positive or negative to PAP2a are less affected.

Figures 2A, 11:
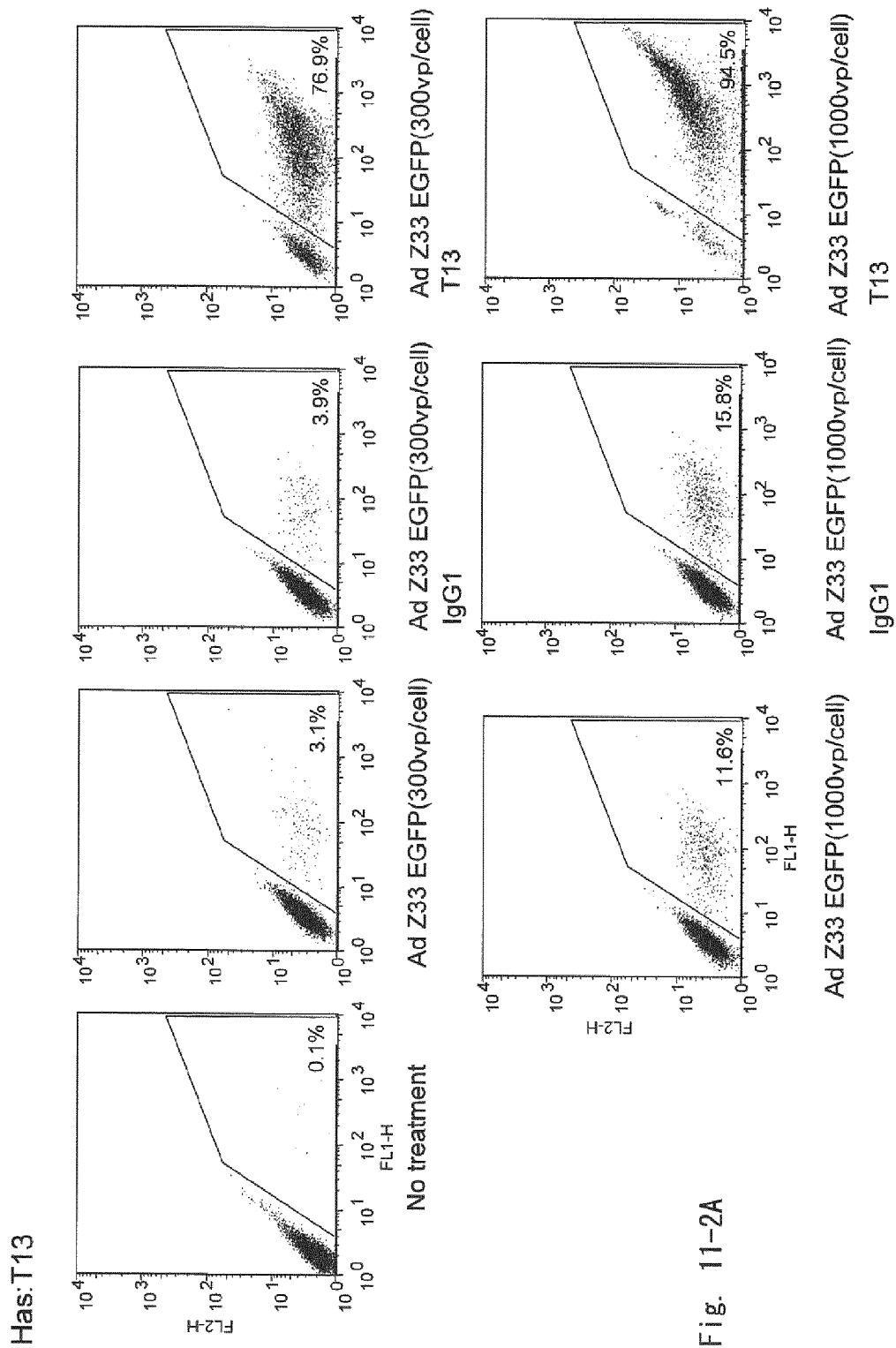

FIG. 11-2A is graphs showing the results of effects of T13 on the multiplicity of infection of FZ33 adenovirus for Has cells, which multiplicity of infection was evaluated by flow cytometry at vector doses of 300 vp/cell and 1000 vp/cell, using EGFP-expressing Ax3CAZ3-FZ33. As illustrated, it is understood that the multiplicity of infection was markedly enhanced, as compared to the case where the cells were pre-treated with T13 (76.9% at 300 vp/cell and 94.5% at 1000 vp/cell) and the case where the cells were pre-treated with control mouse IgG1 (3.9% at 300 vp/cell and 15.8% at 1000 vp/cell). The results demonstrate that in the case of Has cells, gene transfer by FZ33 adenovirus using the T13 antibody provides extremely high enhanced transgene expression efficiency of EGFP, as compared to control (adenovirus alone Ad, control IgG1 added).

Figures 2B, 11:
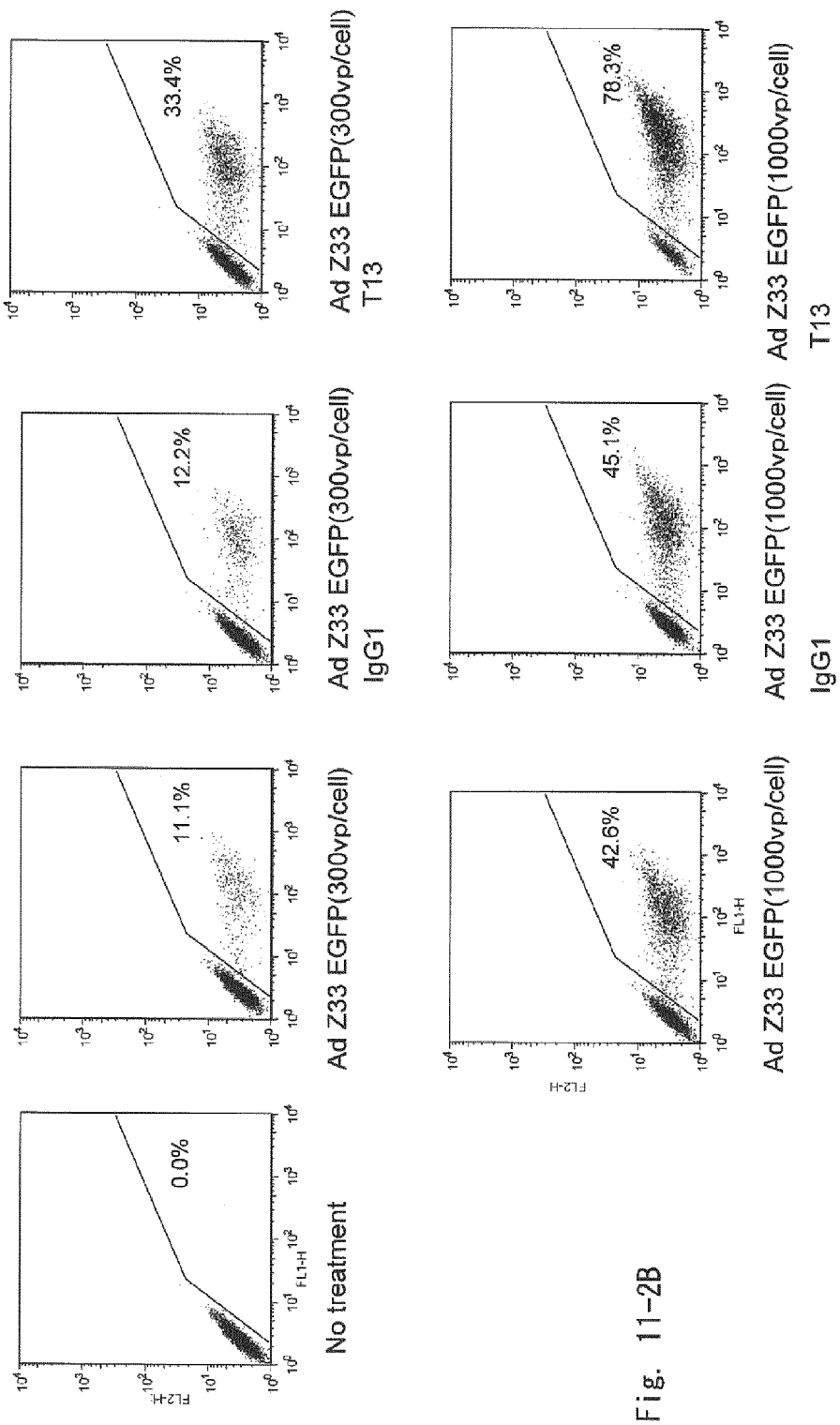

FIG. 11-2B is graphs showing the results of effects of T13 on the multiplicity of infection of FZ33 adenovirus for pancreatic cancer cell Miapaca2, which multiplicity of infection was evaluated by flow cytometry at vector doses of 300 vp/cell and 1000 vp/cell, using EGFP-expressing Ax3CAZ3-FZ33. As illustrated, it is understood that the multiplicity of infection was enhanced, as compared to the case where the cells were pre-treated with T13 (33.4% at 300 vp/cell and 78.3% at 1000 vp/cell) and the case where the cells were pre-treated with control mouse IgG1 (12.2% at 300 vp/cell and 45.1% at 1000 vp/cell). The results demonstrate that gene transfer for Miapaca2 cells by FZ33 adenovirus using the T13 antibody provides high enhanced transgene expression efficiency of EGFP, as compared to control (adenovirus alone Ad, control IgG1 added).

Figure 12:
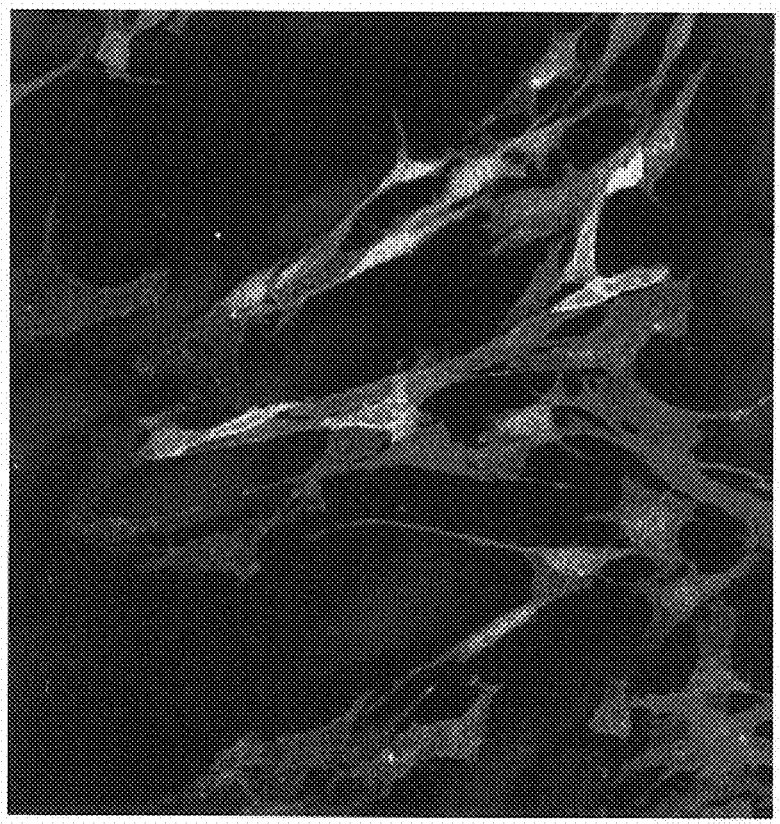
FIG. 12 shows photographs of immunohistochemical staining showing the results of analysis of mixed culture of Has cells and PDF in runs showing the multiplicity of infection of Ax3CAEGFP-FZ33 on various cells when pre-treated with S11.

FIG. 12 shows the results of analysis of mixed culture of Has cells and PDF in runs showing the multiplicity of infection of Ax3CAEGFP-FZ33 on various cells when pre-treated with S11. A blue dye (CellTracker® Blue CMAC (7-amino-4-chloromethylcoumarin): Molecular Probes) was incorporated into human PDF cells (primary culture human fibroblast) weakly positive to PAP2a by adding $2\times10^5$ of PDF and incubating in 5 ml of DMEM-FBS(−) 10 mM CMAC at 37° C. for 45 minutes. Next, a mixture of $2\times10^4$/well of PDF and $2\times10^4$/well of Has cells was seeded to a 2-well CultureSlide. On the following day, the cells were infected with adenovirus Ax3CAEGFP-FZ33 (EGFP expression) using anti-PAP2a antibody in combination with S11. Specifically, 1 µg/500 µl of the S11 antibody (DMEM-FBS(−)) per well was mixed with Ax3CAEGFP-FZ33 at a vector dose of 300/cell for each well, followed by incubation at 4° C. for an hour. The medium was exchanged and incubation was continued. On the following day, the cells were incubated with the S11 antibody (5 µg/ml) as a primary antibody at room temperature for 30 minutes. After washing, the cells were incubated at room temperature for 30 minutes with Alexa Fluor 594 goat anti-mouse IgG antibody (5 µg/ml) as a secondary antibody to stain the cells reacting with anti-PAP2a antibody S11, i.e., Has cells red. Even though Has cells and PDF cells were seeded in the same counts, Has cells grew more 2 days after because of difference in growth activity. Gene transfer was monitored in terms of EGFP expression (green fluorescence in the figure).

The transduced cells (i.e., cells emitting green fluorescence) in FIG. 12 are all shown in red (PAP2a-positive Has cells), whereas gene transfer is not made in blue PDF cells. This demonstrates that by the gene delivery method using the S11 antibody, gene transfer can be achieved selectively to PAP2a-positive cells with high efficiency, by distinctly distinguishing from the cells negative or weakly positive to PAP2a. The selective gene delivery method as such is considered to be effective for cancer therapy.

Example 7

Diagnosis of Pancreatic Cancer by Immunohistochemical Staining Using Anti-PAP2a Antibody FIGS. 14-1 and 14-2 are photographs showing the results of immunohistochemical staining of surgical specimens from human clinical cases with pancreatic cancer by anti-PAP2a antibody. The procedure for immunohistochemical staining is briefly described below.

Formalin-fixed, paraffin-embedded surgical specimens were deparaffinized in xylol/ethanol, soaked in 0.01 M citrate buffer (pH 6.4) and autoclaved at 121° C. for 5 minutes. Next, one or two drops of 10% normal rabbit serum was dropwise added to spread all over the tissue and reacted at room temperature for 10 minutes to block non-specific reactions. Next, the S11 anti-PAP2a antibody (1-2 µg/ml) was laid on the specimens in 50-100 µl/specimen to spread all over the tissue and allowed to stand in a moist chamber, followed by reacting at 4° C. overnight. After washing with PBS, biotinylated rabbit anti-mouse secondary antibody (secondary antibody is commercially available from Vector, DAKO, Nichirei, etc.) was laid on, followed by reacting at room temperature for an hour. After washing with PBS, an adequate amount of the avidin/enzyme reagent from Vector's peroxidase/avidin-biotin complex (Avidin Biotin Complex, ABC) stain kit was placed on, followed by reacting at room temperature for an hour. After washing with PBS, the slide was soaked in a DAB solution (solution obtained by dissolving 5 mg of DAB in 100 ml of 0.05 M Tris-HCl, pH 7.6 and adding thereto 0.1-0.2 ml of 0.3% aqueous hydrogen peroxide solution) for about 1 minutes and observed macroscopically or microscopically.

While monitoring color development, the reaction was terminated by distilled water. Nuclear staining was further performed with hematoxylin for 35 minutes to effect dehydration, infiltration and embedding. According to this method, the antigen-positive site turns dark brown by DAB color development.

In FIGS. 14-1 and 14-2, A, B and C are the results of immunohistochemical staining of surgical specimens from 3 other patients (cases A, B and C), respectively. The photographs at the upper column are staining of the region containing pancreatic cancer tissue and the photographs at the lower column are staining of the non-cancerous region around the pancreatic cancer tissue on the same slide. As shown in FIG. 14, the pancreatic cancer tissue was stained strongly positively in the surgical specimens from human clinical cases with pancreatic cancer by using the S11 antibody. On the other hand, by using the S11 antibody, the tissue around the pancreatic tissue consisting of the non-cancerous region was stained negatively or weakly positively (glandular portion). In other words, it was demonstrated that the PAP2a antigen molecule was strongly expressed specifically in the human pancreatic cancer tissue. It was thus demonstrated that pancreatic cancer can be diagnosed by anti-PAP2a antibody such as the S11 antibody and the targeting therapy by anti-PAP2a antibody such as the S11 antibody is effective for the treatment of human pancreatic cancer.

Example 8

Immunohistochemical Staining of Various Tissue Samples from Human Clinical Cases with Anti-PAP2a Antibody S11

In order to further demonstrate that PAP2a is expressed specifically in tumor tissues and the anti-PAP2a antibody is useful for the detection of such tumor tissues (diagnosis of tumors) and for the treatment of tumors, immunohistochemical staining tests with the anti-PAP2a antibody S11 of the present invention were performed using various human tumor tissues (prostate cancer tissue, human thyroid cancer tissue, human ovarian cancer tissue and human lung cancer tissue) as well as various human normal tissues (lymph node tissue, spleen tissue, bone marrow tissue, liver tissue, large intestinal mucosa tissue, bladder tissue, thyroid tissue, aorta tissue, heart tissue and skeletal muscle tissue).

Method

Tumor tissue and normal tissue samples were prepared as deparaffinized section slides from formalin-fixed, paraffin-embedded block specimens stored at Department of Pathology, Sapporo Medical University. The anti-PAP2a antibody S11 and peroxidase-conjugated anti-mouse immunoglobulin were used as primary and secondary antibodies, respectively, and reacted with the section slides described above, followed by color development with DAB (3,3'-diaminobenzidine tetrahydrochloride).

The results are shown in FIGS. 15-29 and FIGS. 31-40.

Results

Figure 15:
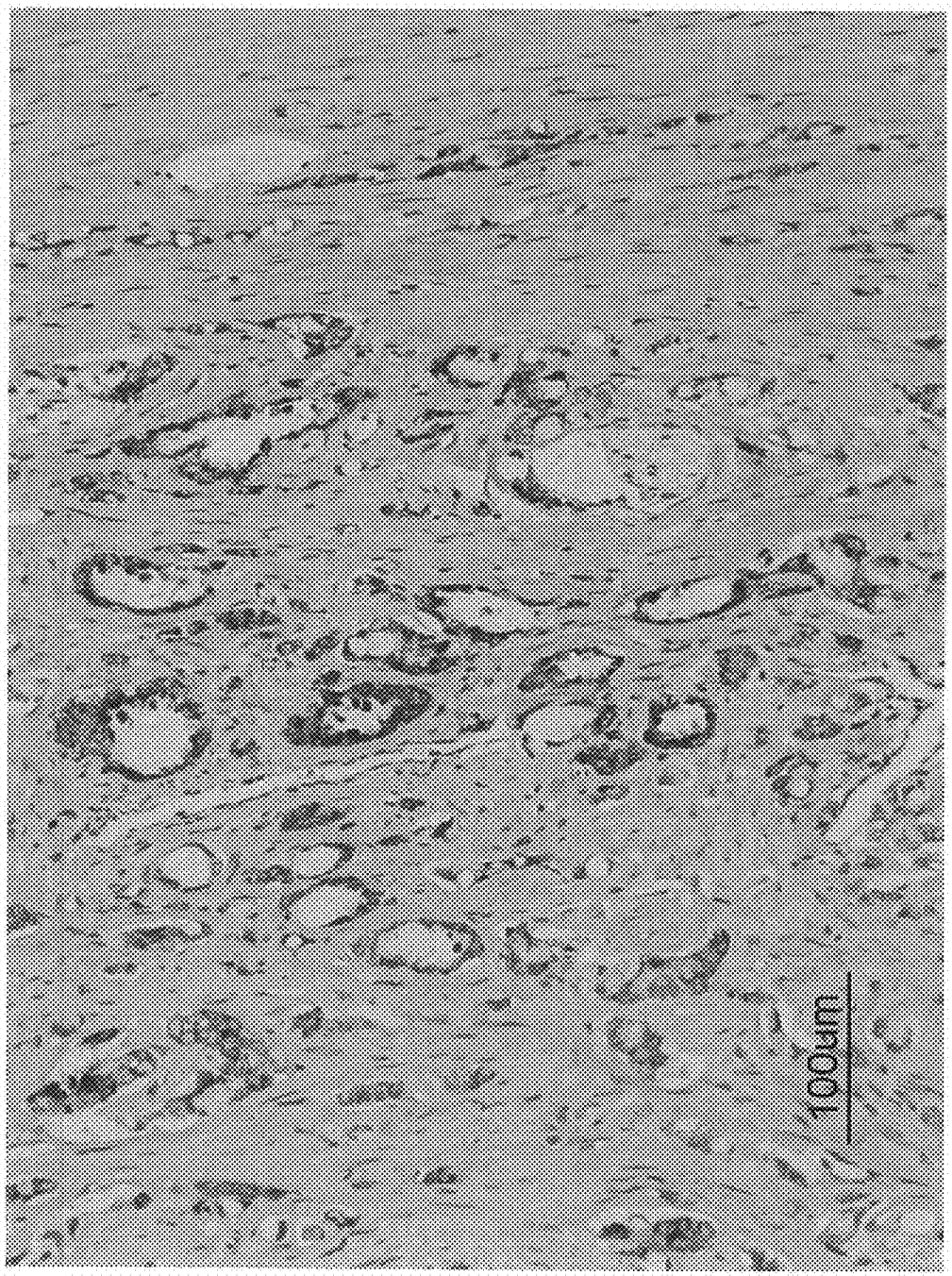
FIG. 15 is a microscopic photograph showing the results of the surgical specimen from the prostate cancer case (patient 03-1016-9), which underwent immunohistochemical staining by the S11 antibody.

FIG. 15 is a microscopic photograph showing the results of the surgical specimen from the prostate cancer case (patient 03-1016-9), which underwent immunohistochemical staining. Staining of tumor cells (positive) was observed.

Figure 16:
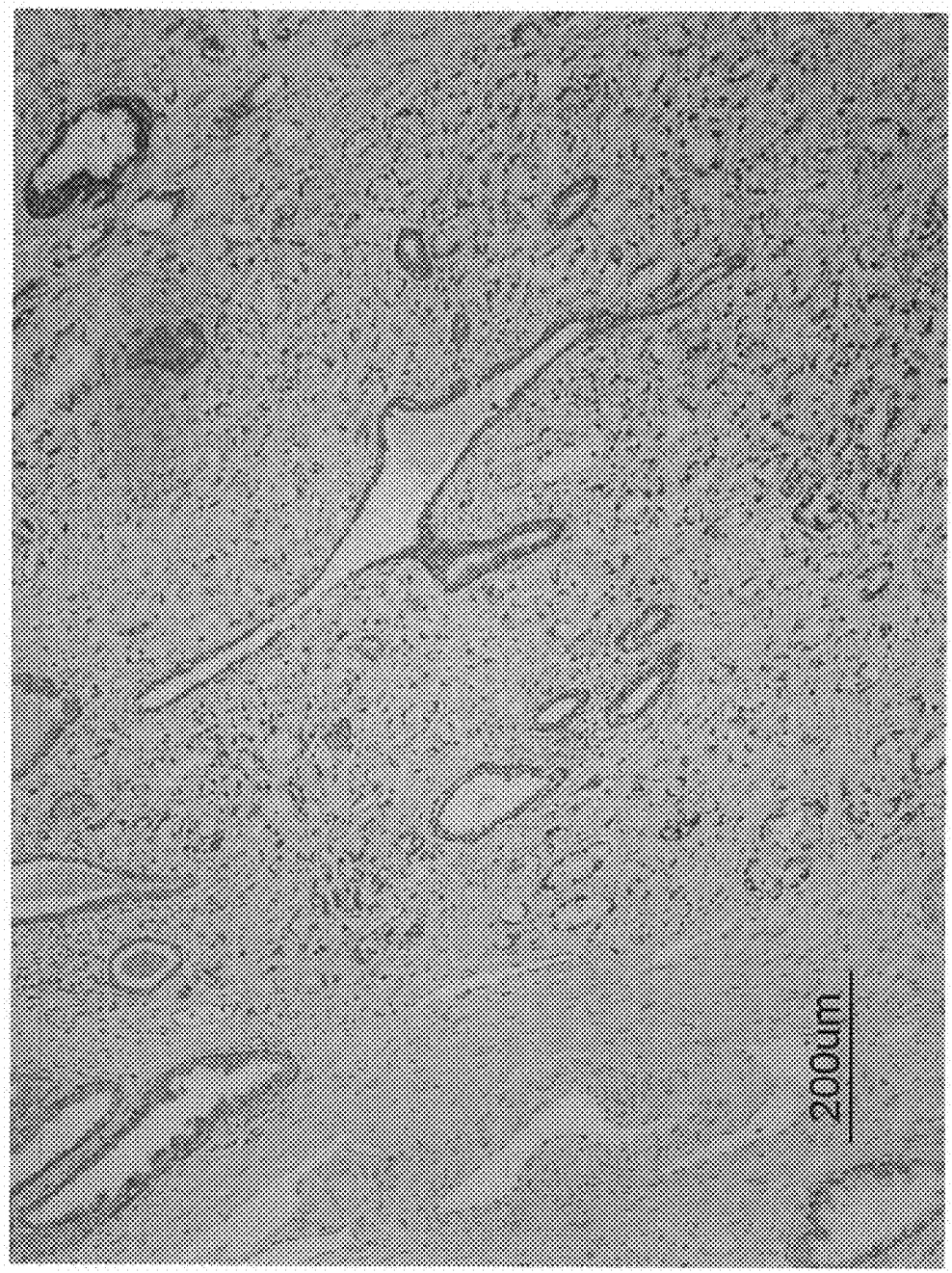
FIG. 16 is a microscopic photograph showing the results of immunohistochemical staining of the surgical specimen from the prostate cancer case (the same patient 03-1016-9 as in FIG. 15) by the S11 antibody.

FIG. 16 is a microscopic photograph showing the results of immunohistochemical staining of the surgical specimen from the prostate cancer case (the same patient 03-1016-9 as in FIG. 15). Staining of tumor cells (positive) is observed. Staining with S11 is positive in prostate cancer cells. On the other hand, the S11 staining is weakly positive in the prostate tissue with prostatic hypertrophy and the normal prostate tissue, and negative in the interstitial tissue.

Figure 17:
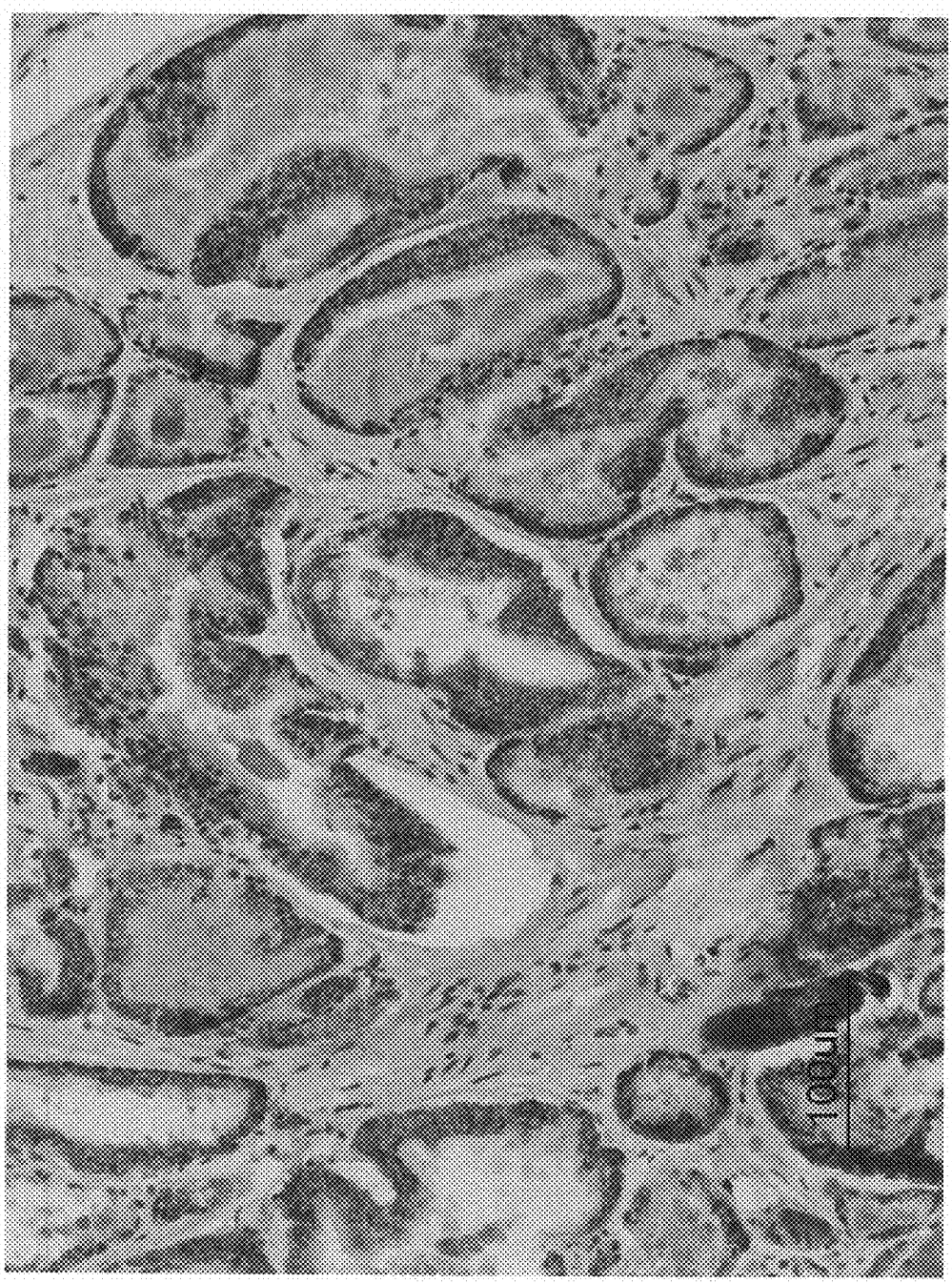
FIG. 17 is a microscopic photograph showing the results of immunohistochemical staining of the surgical specimen from the prostate cancer case (patient 03-2215-1) by the S11 antibody.

FIG. 17 is a microscopic photograph showing the results of immunohistochemical staining of the surgical specimen from the prostate cancer case (patient 03-2215-1). Staining of tumor cells (positive) is observed. The S11 staining is positive in prostate cancer cells. On the other hand, the S11 staining is negative in the prostate tissue with prostatic hypertrophy, normal prostate tissue and interstitial tissue.

Figure 18:
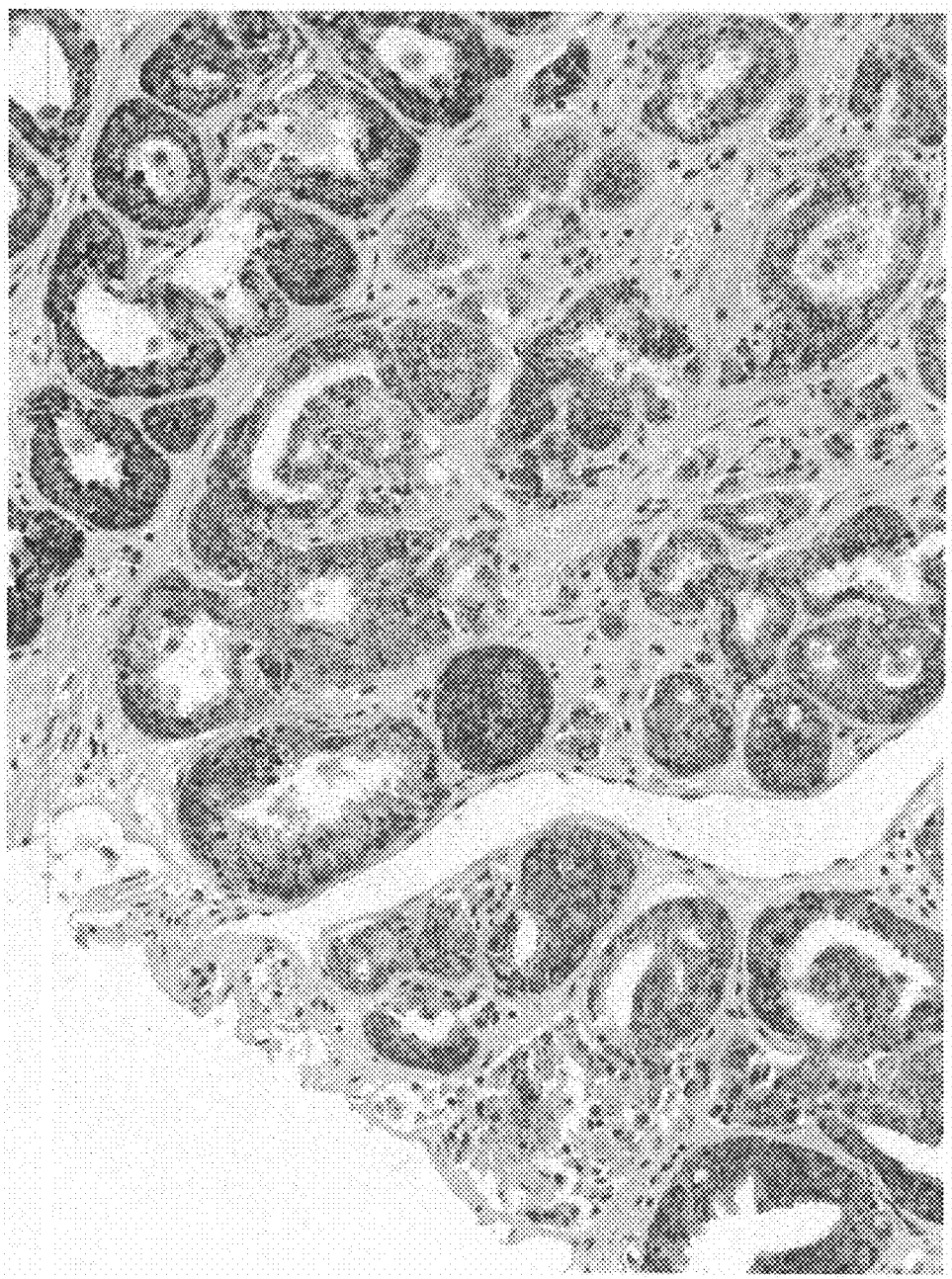
FIG. 18 is a microscopic photograph showing the results of immunohistochemical staining of the surgical specimen from the prostate cancer case (patient 03-2342-13) by the S11 antibody.

FIG. 18 is a microscopic photograph showing the results of immunohistochemical staining of the surgical specimen from the prostate cancer case (patient 03-2342-13). Staining of tumor cells (positive) is observed. The S11 staining is positive in prostate cancer cells. On the other hand, the S11 staining is negative in the prostate tissue with prostatic hypertrophy, normal prostate tissue and interstitial tissue.

Figure 19:
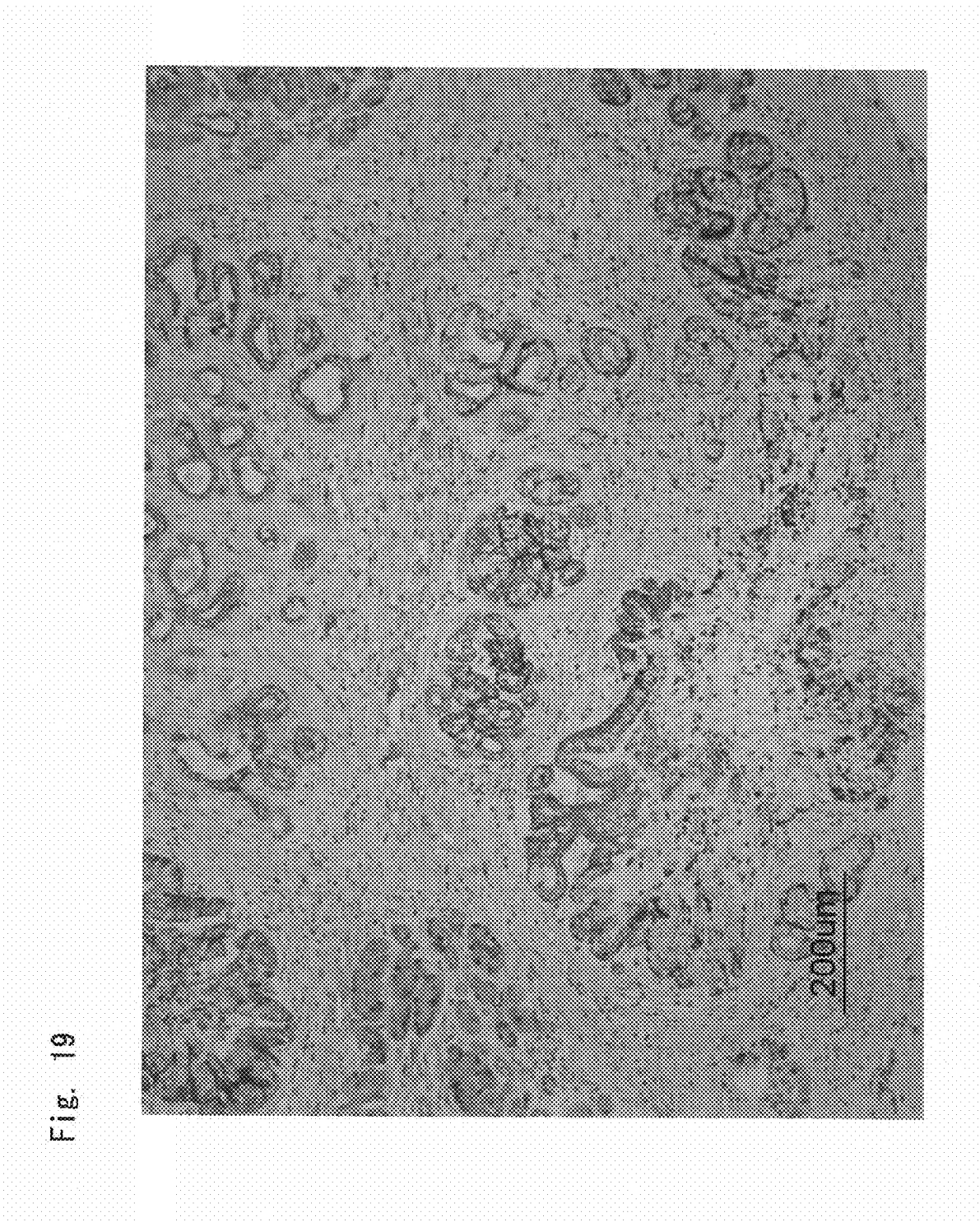
FIG. 19 is a microscopic photograph showing the staining of the surgical specimen from the prostate cancer case (patient 03-2767-14) by the S11 antibody.

FIG. 19 is a microscopic photograph showing the results of immunohistochemical staining of the surgical specimen from the prostate cancer case (patient 03-2767-14). Staining of tumor cells (positive) is observed. The S11 staining is positive in prostate cancer cells. On the other hand, the S11 staining is negative in the prostate tissue with prostatic hypertrophy, normal prostate tissue and interstitial tissue.

Figure 20:
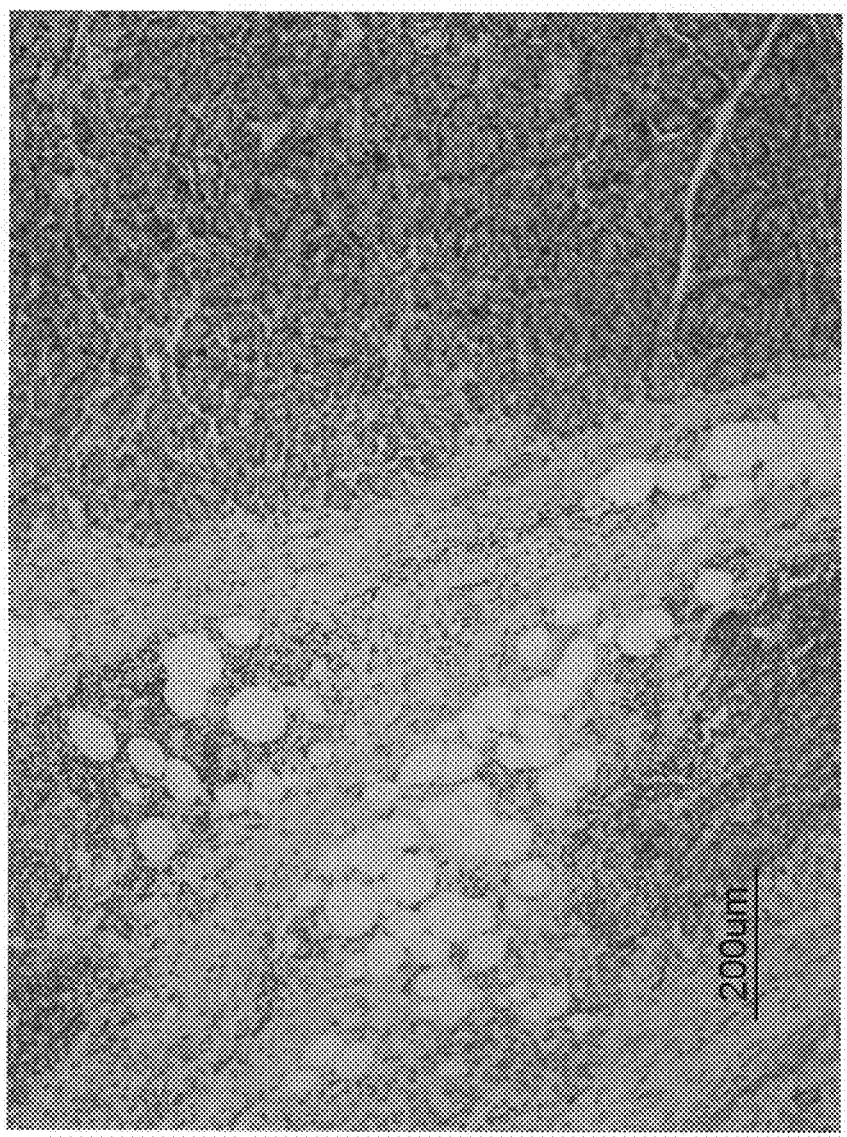
FIG. 20 is a microscopic photograph showing the results of immunohistochemical staining of the surgical specimen from the prostate cancer case by the S11 antibody. The prostate cancer tissue on the observers' right hand is PAP2a-positive, and the normal tissue and inflammatory cell infiltration cells on the observers' left hand are PAP2a-negative.

FIG. 20 is a microscopic photograph showing the results of immunohistochemical staining. Prostate cancer (PAP2a-positive) is on the observers' right hand and inflammatory cell infiltration (PAP2a-negative) on the observers' left hand. The PAP2a antibody does not react with inflammatory cells of the host such as normal lymphocytes, neutrophils, etc., and is suggested to be useful for the diagnosis and targeting therapy of prostate cancer.

Figure 21:
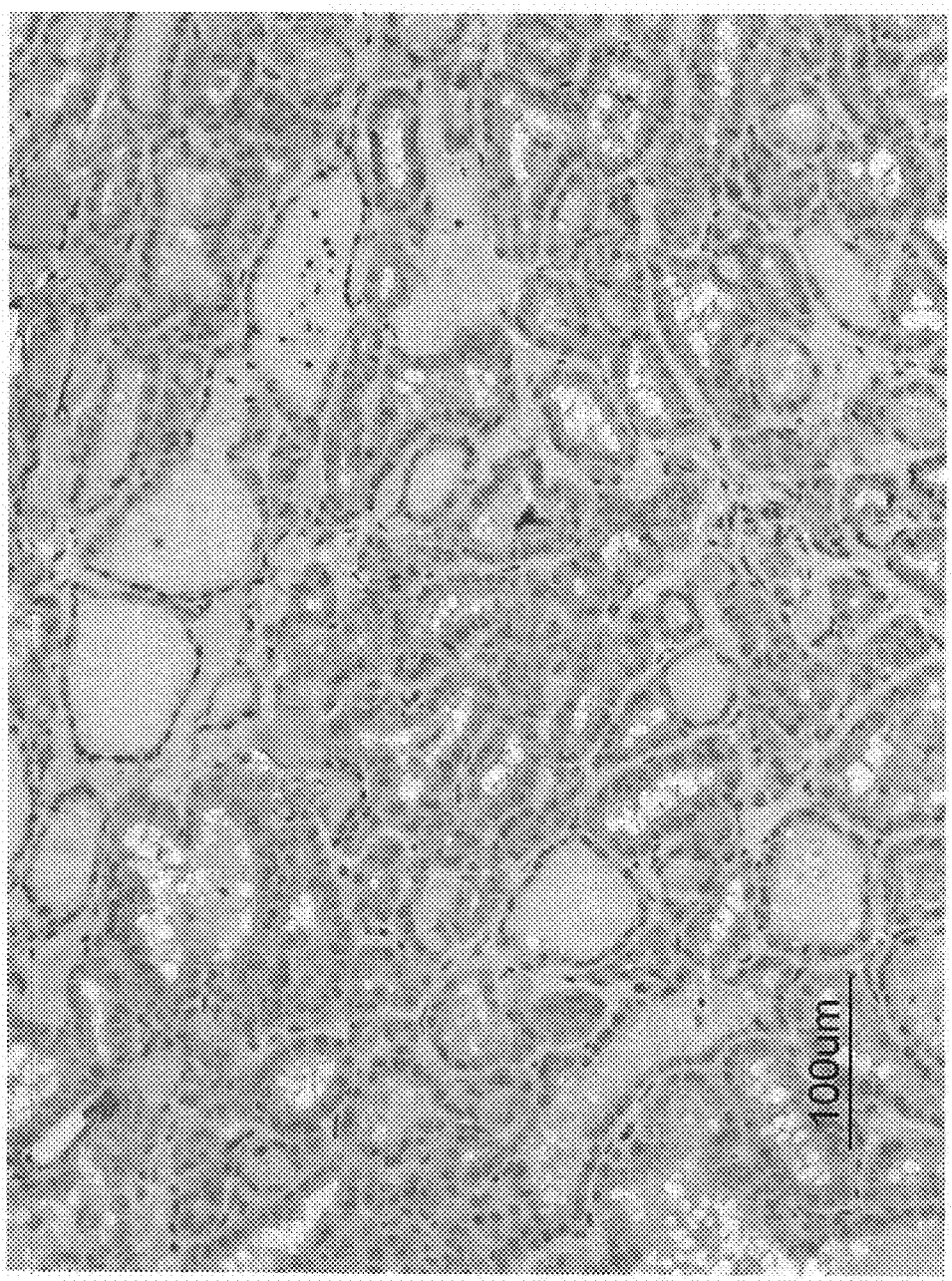
FIG. 21 is a microscopic photograph showing the results of immunohistochemical staining of the surgical specimen (follicular adenocarcinoma of the thyroid gland) from the thyroid cancer case collected from the patient (array A7) by the S11 antibody.

FIG. 21 is a microscopic photograph showing the results of immunohistochemical staining of the surgical specimen (follicular adenocarcinoma of the thyroid gland) from the thyroid cancer case collected from the patient (array A7). Staining of tumor cells (positive) is observed. The S11 staining is positive in thyroid cancer cells.

Figure 22:
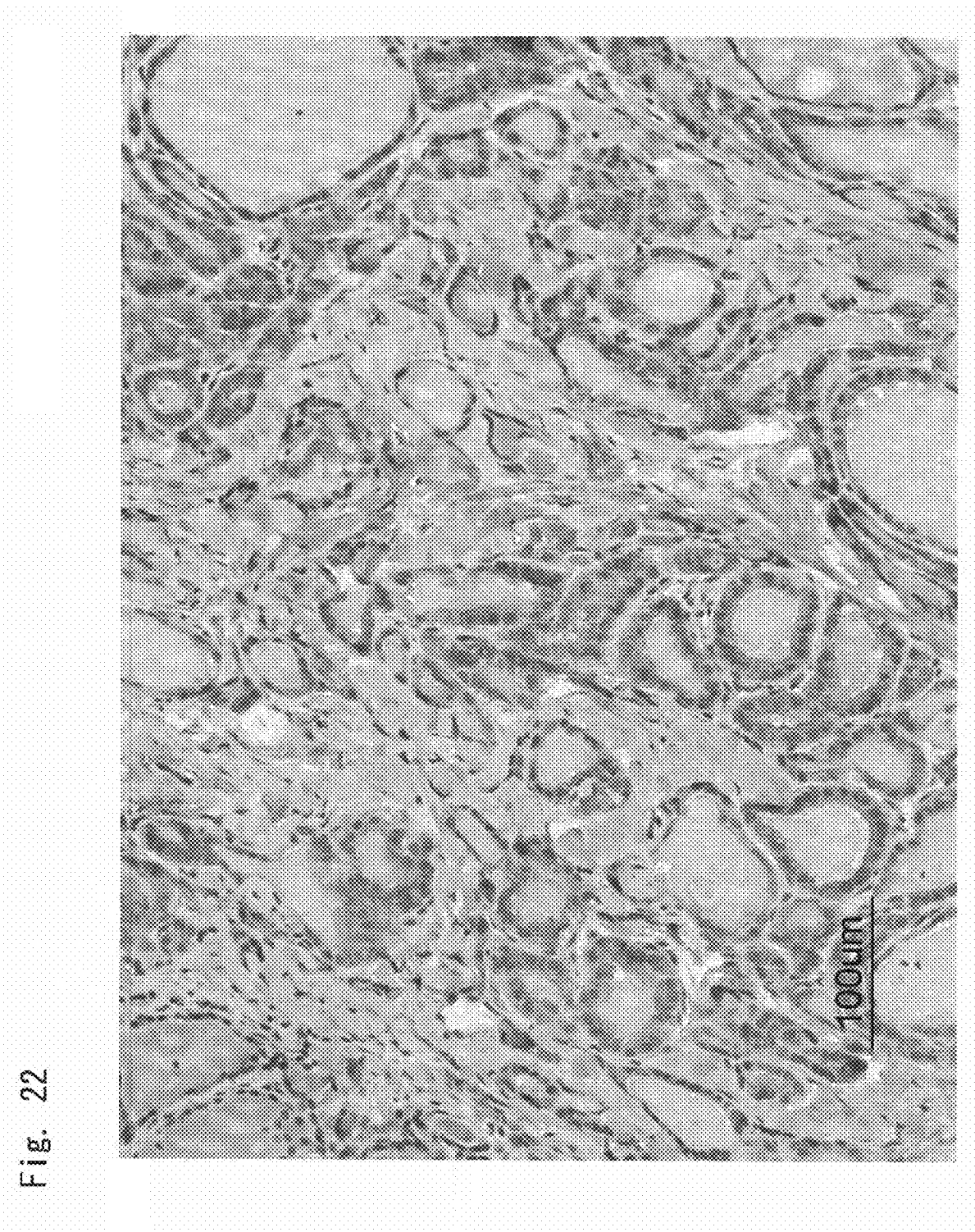
FIG. 22 is a microscopic photograph showing the results of immunohistochemical staining of the surgical specimen (follicular adenocarcinoma) from another thyroid cancer case different from FIG. 21, a sample collected from patient 2 (array B11) by the S11 antibody.

FIG. 22 is a microscopic photograph showing the results of immunohistochemical staining of the surgical specimen (follicular adenocarcinoma) from another thyroid cancer case different from FIG. 21, a sample collected from patient 2 (array B11), by the S11 antibody. Staining of tumor cells (positive) is observed. Brown staining within the follicles is background staining.

Figure 23:
FIG. 23 is a microscopic photograph showing the results of immunohistochemical staining of the surgical specimen (OvCa patient 03-241-5) from the ovarian cancer case by the S11 antibody.

FIG. 23 is a microscopic photograph showing the results of immunohistochemical staining of the surgical specimen (OvCa patient 03-241-5) from the ovarian cancer case. The S11 staining is positive in ovarian cancer cells. On the other hand, the S11 staining is negative in the interstitial tissue.

Figure 24:
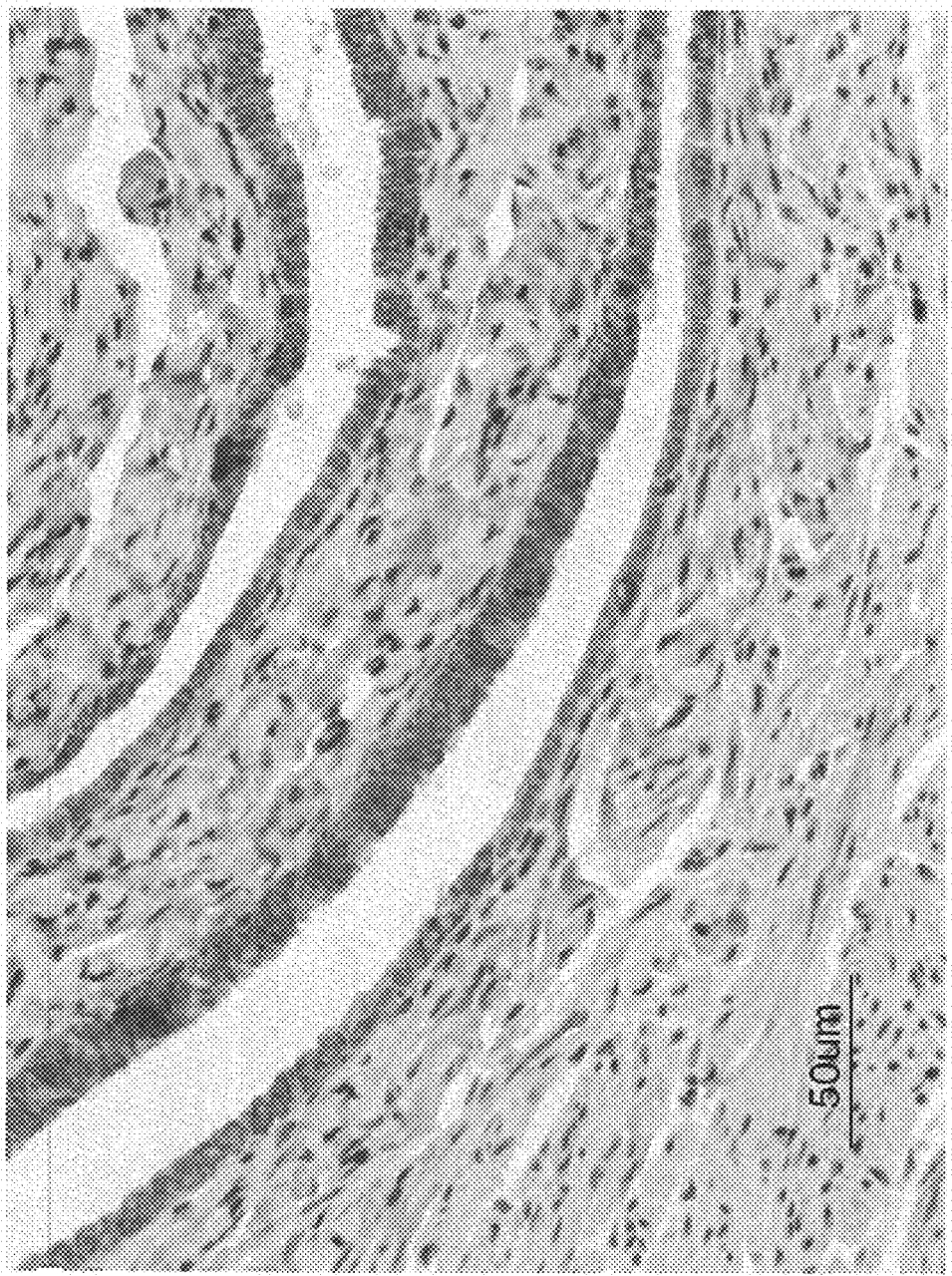
FIG. 24 is a microscopic photograph showing the results of immunohistochemical staining of another surgical specimen (OvCa patient 03-830-1) from the ovarian cancer case by the S11 antibody.

FIG. 24 is a microscopic photograph showing the results of immunohistochemical staining of the surgical specimen (OvCa patient 03-830-1) from another case with ovarian cancer. The S11 staining is positive in ovarian cancer cells. On the other hand, the S11 staining is negative in the interstitial tissue.

Figure 25:
FIG. 25 is a microscopic photograph showing the results of immunohistochemical staining of the surgical specimen (OvCa patient 03-1252-13) from another ovarian cancer case by the S11 antibody.

FIG. 25 is a microscopic photograph showing the results of immunohistochemical staining of the surgical specimen (OvCa patient 03-1252-13) from another case with ovarian cancer. The S11 staining is positive in ovarian cancer cells. On the other hand, the S11 staining is negative in the interstitial tissue.

Figure 26:
FIG. 26 is a microscopic photograph showing the results of immunohistochemical staining of the surgical specimen (OvCa patient 03-2881-4) from another ovarian cancer case by the S11 antibody.

FIG. 26 is a microscopic photograph showing the results of immunohistochemical staining of the surgical specimen (OvCa patient 03-2881-4) from another case with ovarian cancer. The S11 staining is positive in ovarian cancer cells.

Figure 27:
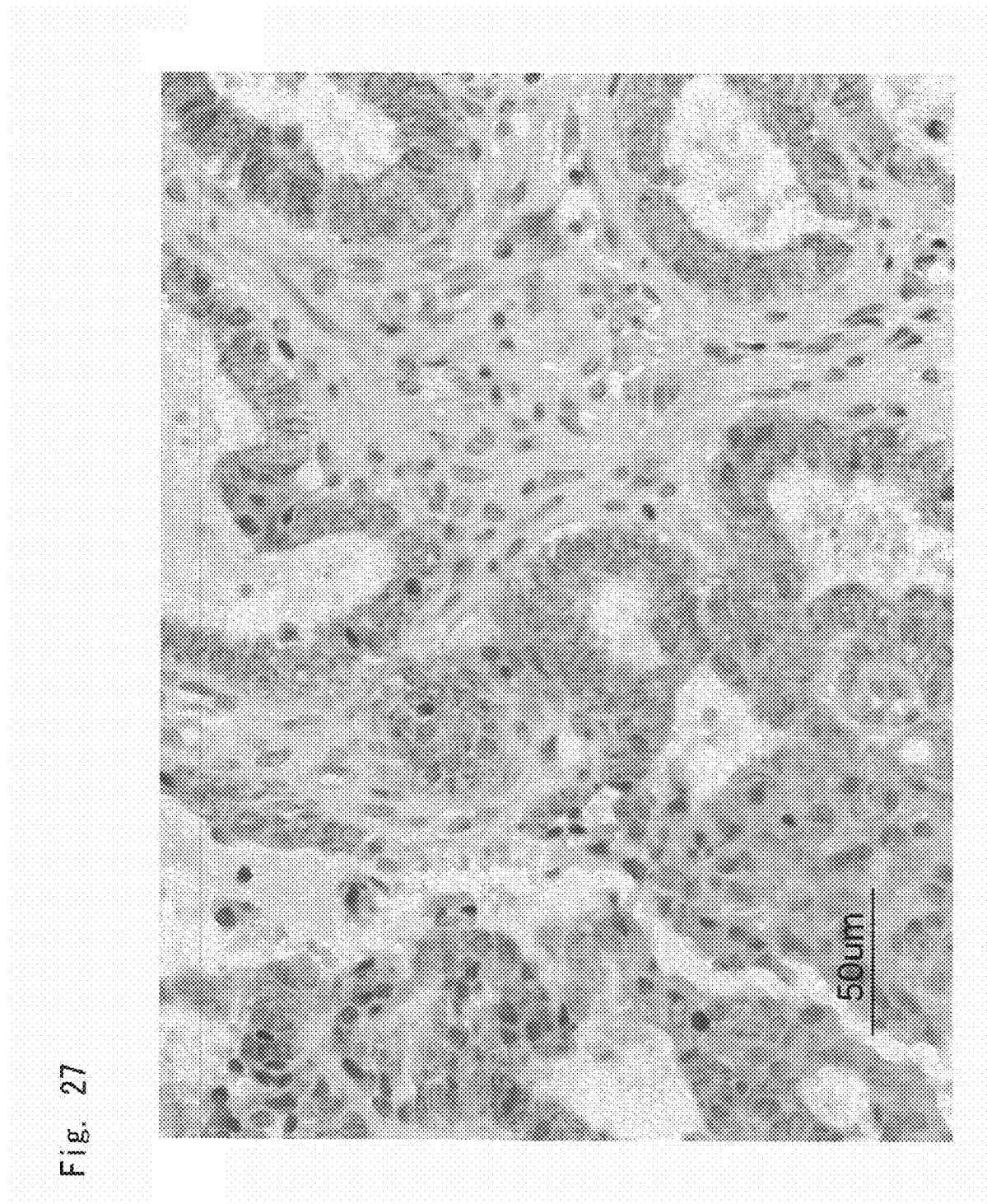
FIG. 27 is a microscopic photograph showing the results of immunohistochemical staining of the surgical specimen (OvCa patient 03-3655-9) from another ovarian cancer case by the S11 antibody.

FIG. 27 is a microscopic photograph showing the results of immunohistochemical staining of the surgical specimen (OvCa patient 03-3655-9) from another case with ovarian cancer. The S11 staining is positive in ovarian cancer cells. On the other hand, the S11 staining is negative in the interstitial tissue. The S11 staining is positive in differentiated adenocarcinoma forming glandular cavities. Formation of undifferentiated tumor cell mass forming no glandular cavity is observed in part and this part is also positive by the S11 staining.

Figure 28:
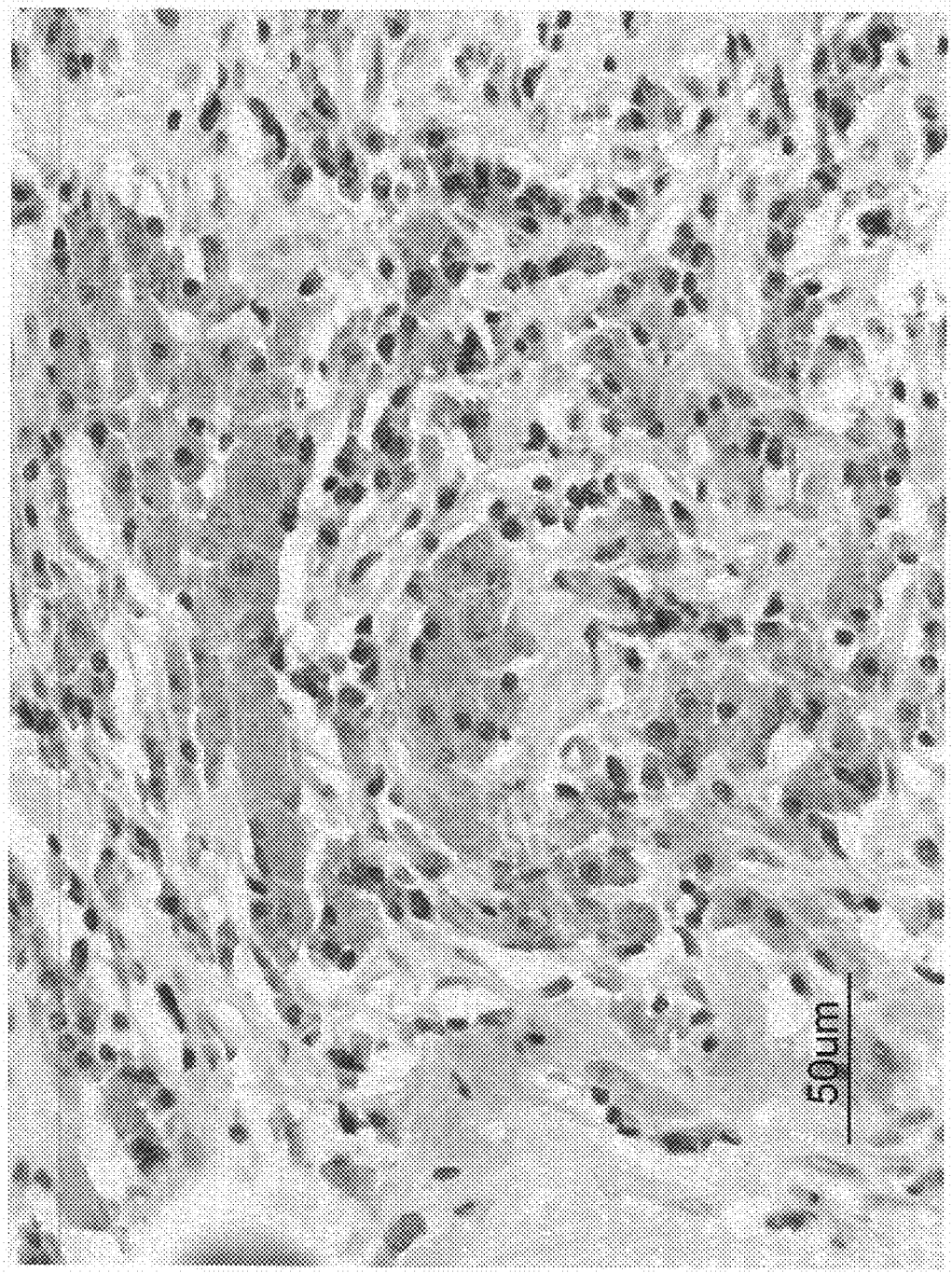
FIG. 28 is a photograph on the same slide as the specimen in FIG. 27 in another viewing field.

FIG. 28 is a photograph on the same slide as the specimen in FIG. 27 in another viewing field. The S11 staining is positive in ovarian cancer cells. On the other hand, the S11 staining is negative in the interstitial tissue. The S11 staining is also strongly positive in undifferentiated infiltration tumor tissue.

Figure 29:
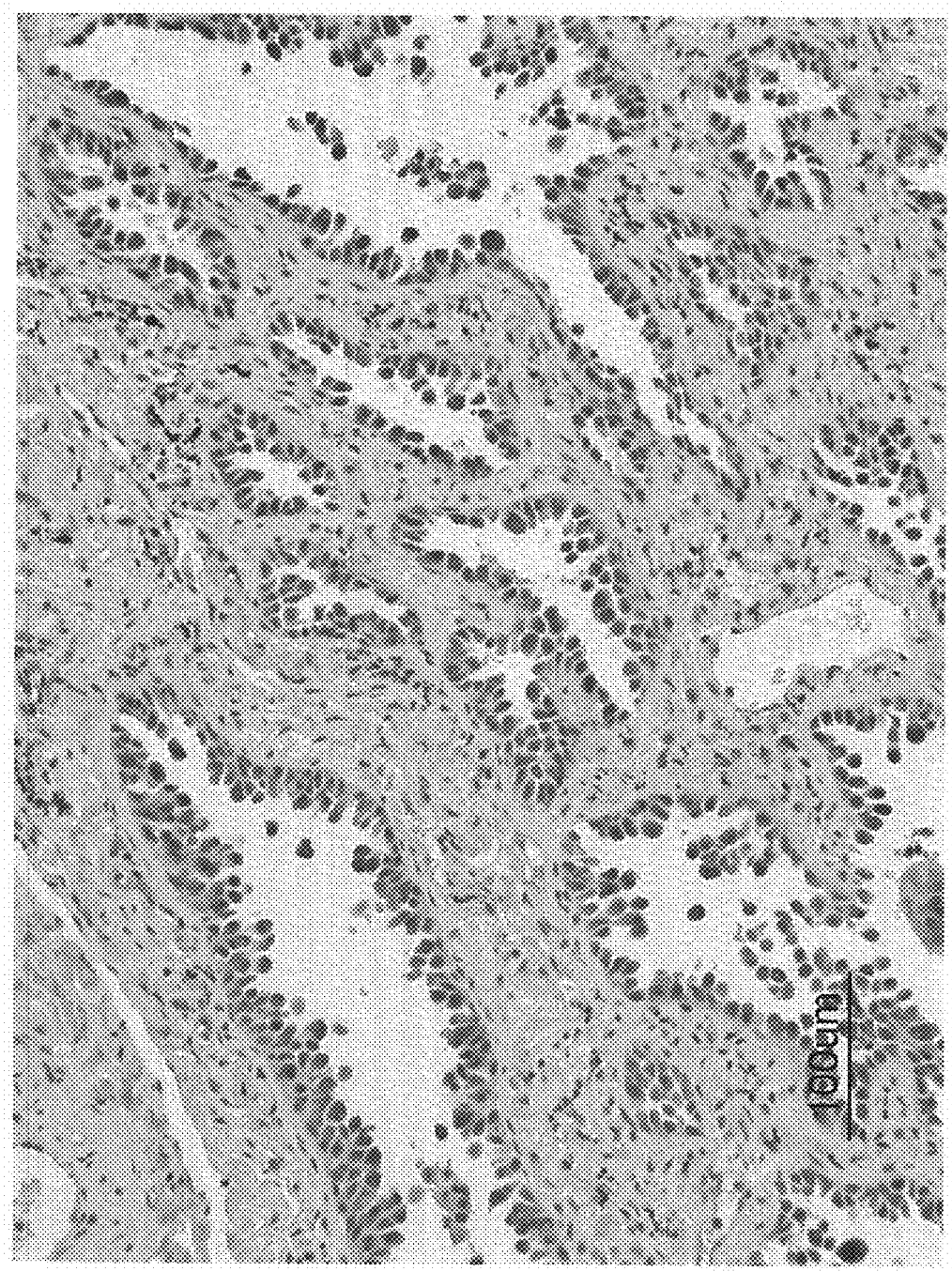
FIG. 29 is a microscopic photograph showing the results of immunohistochemical staining of the surgical specimen from the human lung cancer case (array B3) by the S11 antibody.

FIG. 29 is a microscopic photograph showing the results of immunohistochemical staining of the case of human lung cancer (array B3) by the S11 antibody. Staining of tumor cells (positive) is observed.

Figure 30:
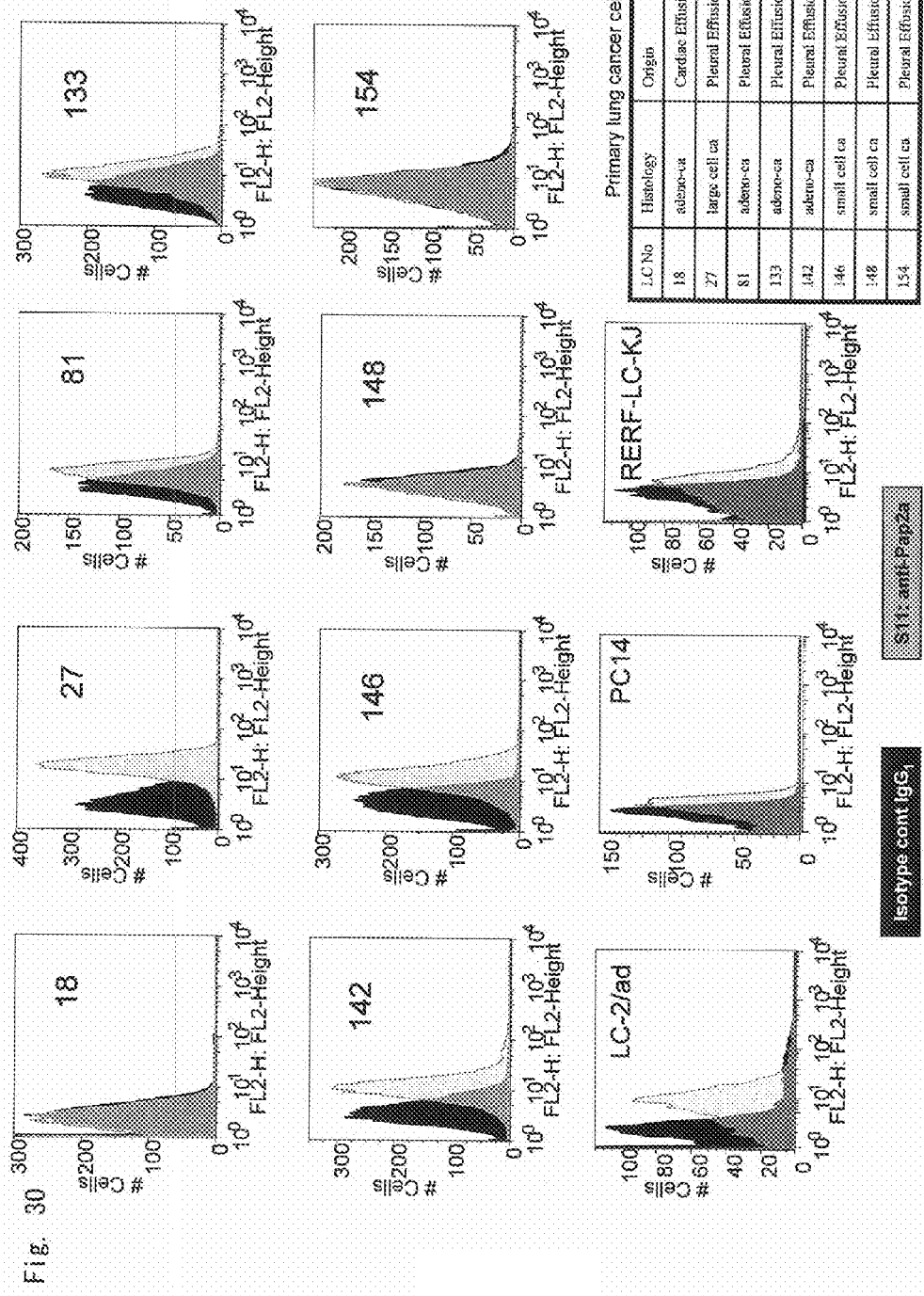
FIG. 30 shows the results of FACS analysis of various human lung cancer cells by the S11 antibody.

FIG. 30 shows the results of FACS analysis of the cells established from various clinical samples of human lung cancer or human lung cancer by the S11 staining. The analysis was performed as in EXAMPLE 6. Details of the cells used are described below.

18: Lung cancer cells derived from clinical samples from the lung or adenocarcinoma or in the pericardial effusion. The S11 staining is negative.

27: Lung cancer cells derived from clinical samples from the lung, large cell carcinoma or pleural effusion. The S11 staining is positive.

81: Lung cancer cells derived from clinical samples from the lung, adenocarcinoma or pleural effusion. The S11 staining is positive.

133: Lung cancer cells derived from clinical samples from the lung, adenocarcinoma or pleural effusion. The S11 staining is positive.

142: Lung cancer cells derived from clinical samples from the lung, adenocarcinoma or pleural effusion. The S11 staining is positive.

146: Lung cancer cells derived from clinical samples from the lung, small cell carcinoma or pleural effusion. The S11 staining is positive.

148: Lung cancer cells derived from clinical samples from the lung, small cell carcinoma or pleural effusion. The S11 staining is negative.

154: Lung cancer cells derived from clinical samples from the lung, small cell carcinoma or pleural effusion. The S11 staining is negative. (see the tables in the figure)

Three of LC-2/ad, PC14 and RERF-LC-KJ are human lung cancer cell lines purchased from ATCC. The S11 staining were all positive in the 3 cases. Based on the data shown in FIGS. 29 and 30 including immunohistochemical staining of lung cancer tissues, FACS analysis of lung cancer cells derived from the clinical samples, FACS analysis of human lung cancer cell lines, etc., it could be confirmed that the expression of PAP2a expressed in lung cancer cells by the S11 antibody can be detected, many positive cases are noted in lung cancer, S11 can be used for diagnosis using PAP2a as a marker, and S11 is applicable to the treatment for targeting PAP2a.

Next, immunohistochemical staining with S11 was attempted in normal tissues. The results are as described below.

Figure 31:
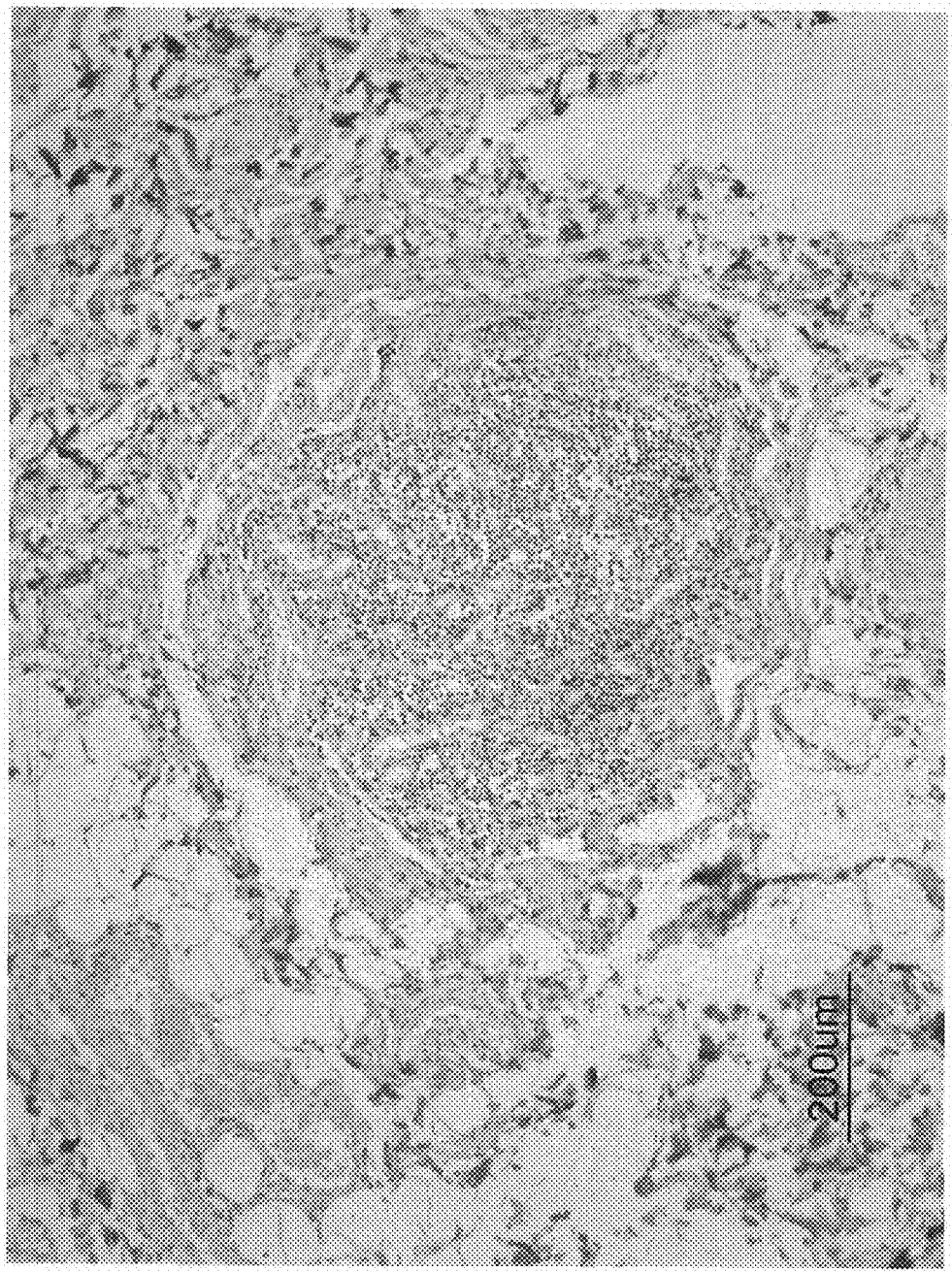
FIG. 31 is a microscopic photograph showing the results of immunohistochemical staining of human normal lymph node by the S11 antibody.

FIG. 31 is a microscopic photograph showing the results of immunohistochemical staining of human normal lymph node. The S11 staining is negative.

Figure 32:
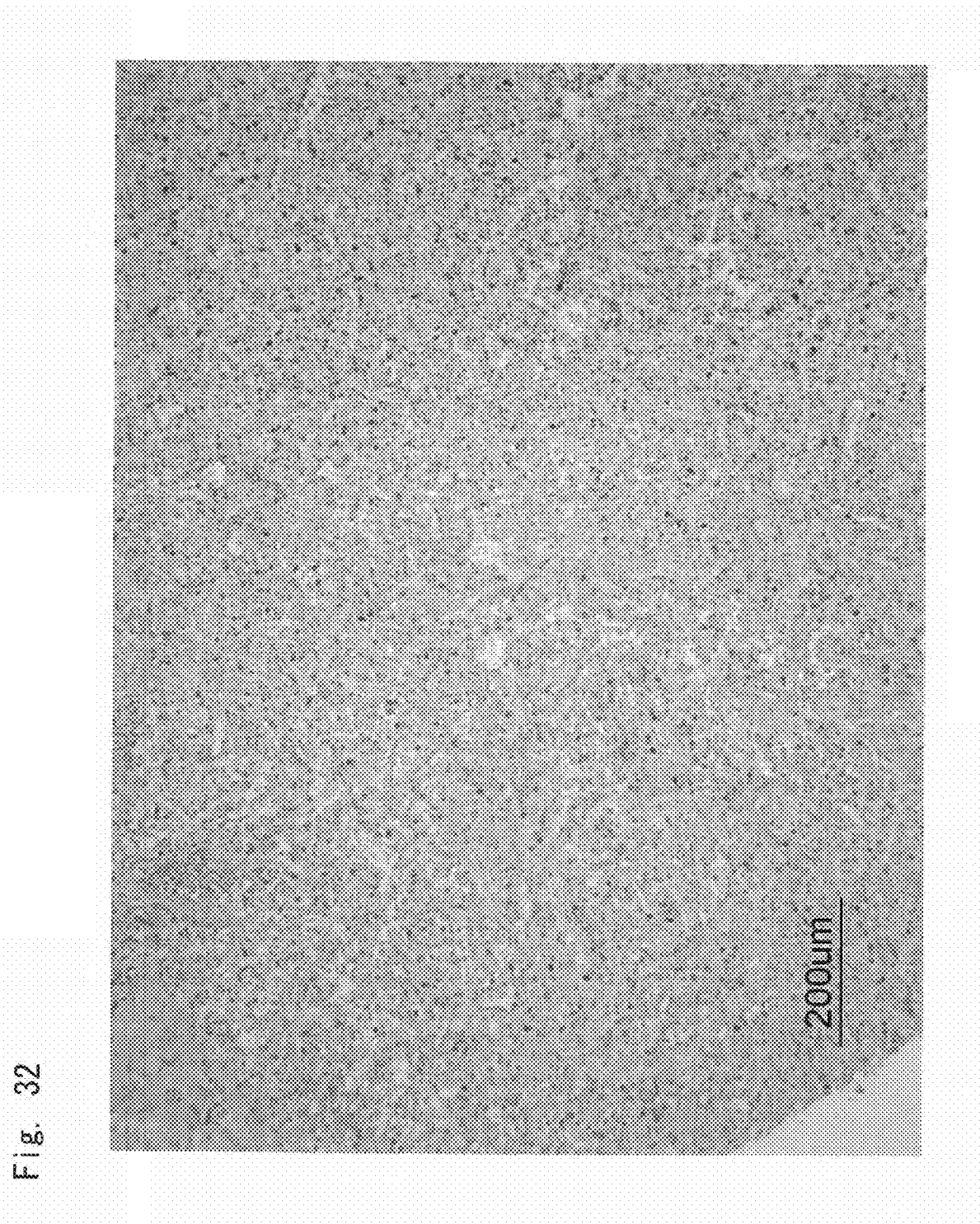
FIG. 32 is a microscopic photograph showing the results of immunohistochemical staining of human normal spleen by the S11 antibody.

FIG. 32 is a microscopic photograph showing the results of immunohistochemical staining of human normal spleen. The S11 staining is negative.

Figure 33:
FIG. 33 is a microscopic photograph showing the results of immunohistochemical staining of human normal bone marrow by the S11 antibody.

FIG. 33 is a microscopic photograph showing the results of immunohistochemical staining of human normal bone marrow. The S11 staining is negative.

Figure 34:
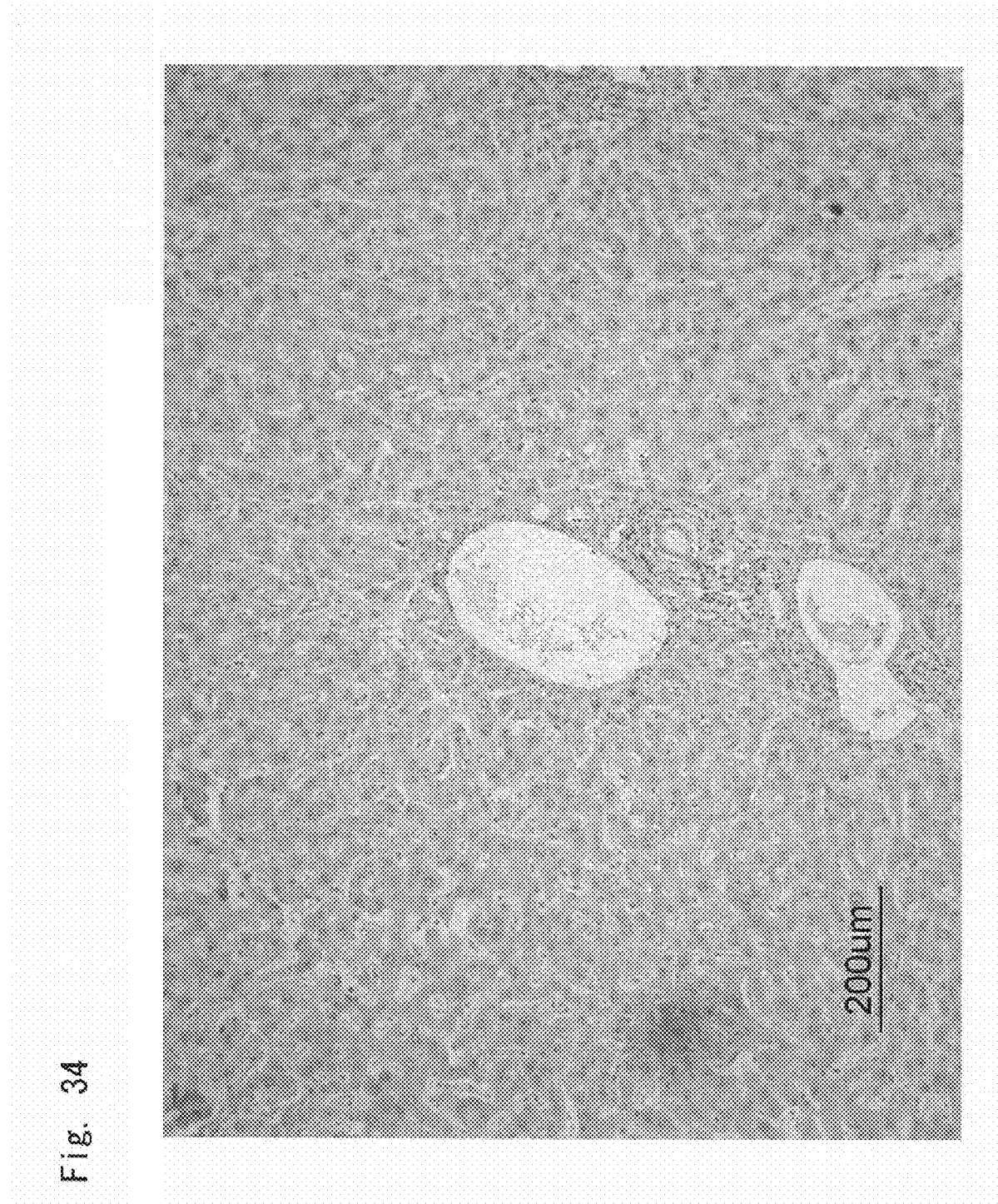
FIG. 34 is a microscopic photograph showing the results of immunohistochemical staining of human normal liver by the S11 antibody.

FIG. 34 is a photograph showing the results of immunohistochemical staining of human normal liver. The S11 staining is negative.

Figure 35:
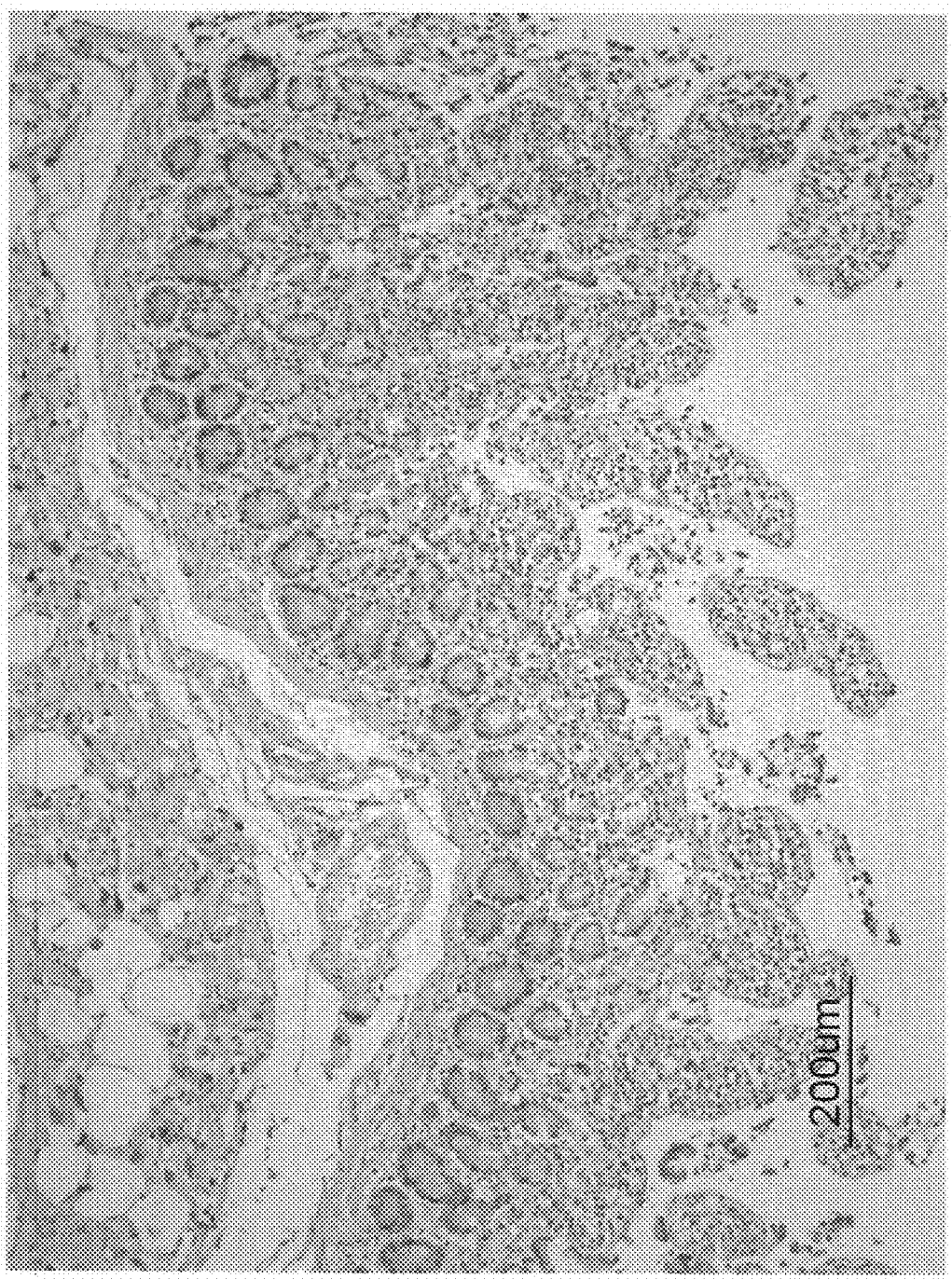
FIG. 35 is a microscopic photograph showing the results of immunohistochemical staining of normal human large intestinal mucosa by the S11 antibody.

FIG. 35 is a microscopic photograph showing the results of immunohistochemical staining of normal human large intestinal mucosa. The S11 staining is negative.

Figure 36:
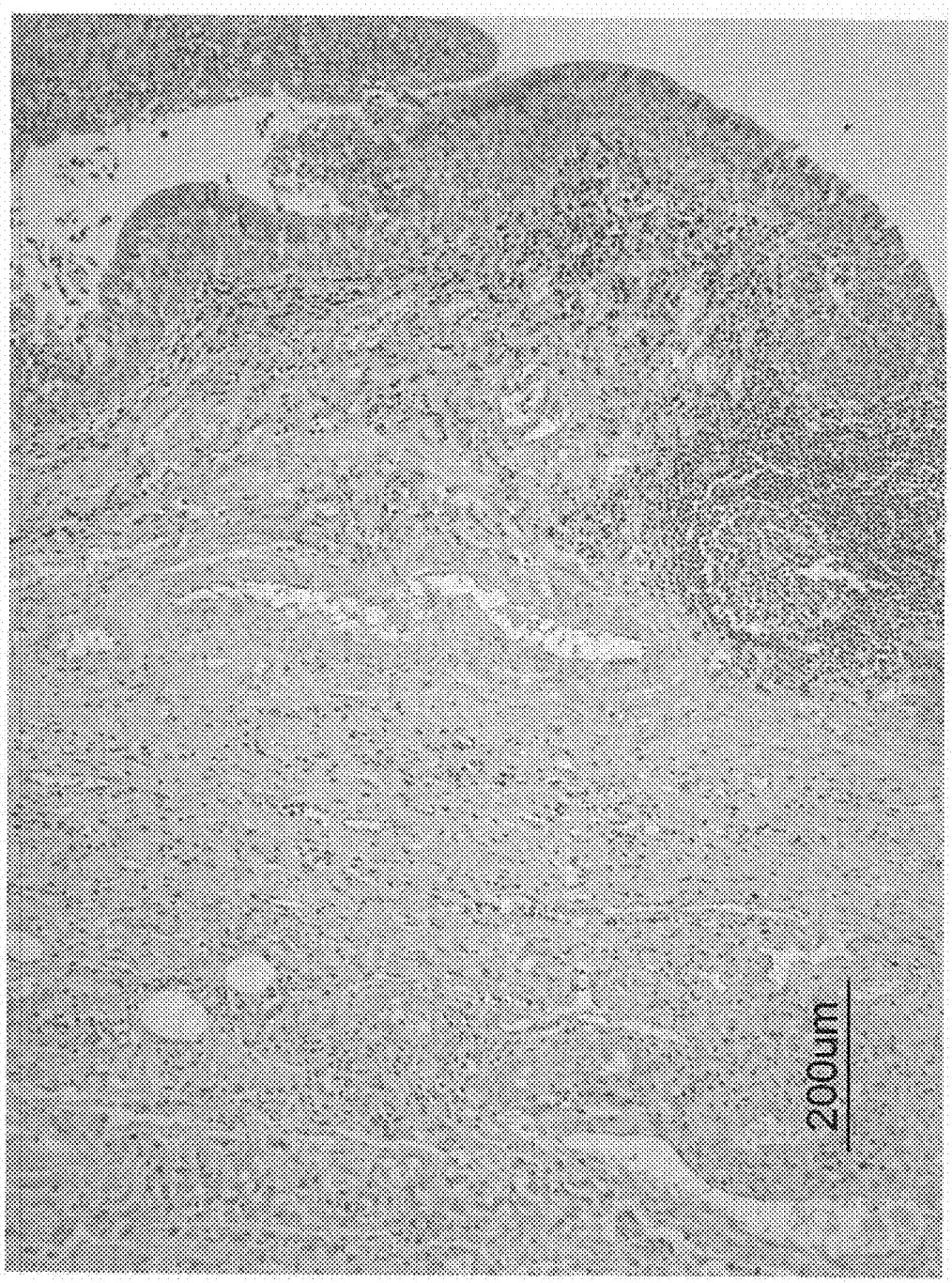
FIG. 36 is a microscopic photograph showing the results of immunohistochemical staining of human normal bladder by the S11 antibody.

FIG. 36 is a microscopic photograph showing the results of immunohistochemical staining of human normal bladder. The S11 staining is negative.

Figure 37:
FIG. 37 is a microscopic photograph showing the results of immunohistochemical staining of normal human thyroid gland by the S11 antibody.

FIG. 37 is a microscopic photograph showing the results of immunohistochemical staining of normal human thyroid gland. The S11 staining is negative in thyroid gland tissues. The staining inside of follicles is a background staining.

Figure 38:
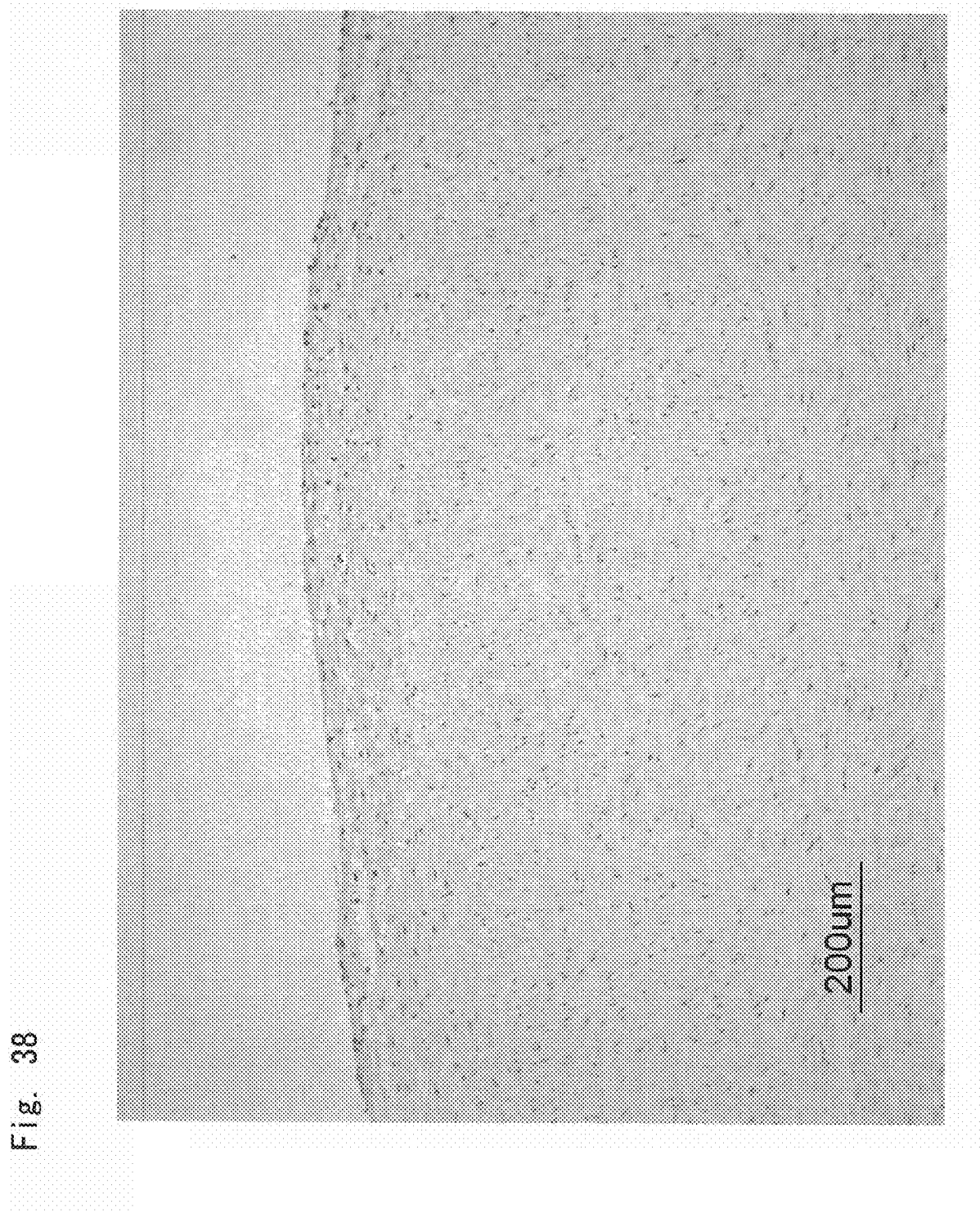
FIG. 38 is a microscopic photograph showing the results of immunohistochemical staining of normal human aorta by the S11 antibody.

FIG. 38 is a microscopic photograph showing the results of immunohistochemical staining of normal human aorta. The S11 staining is negative.

Figure 39:
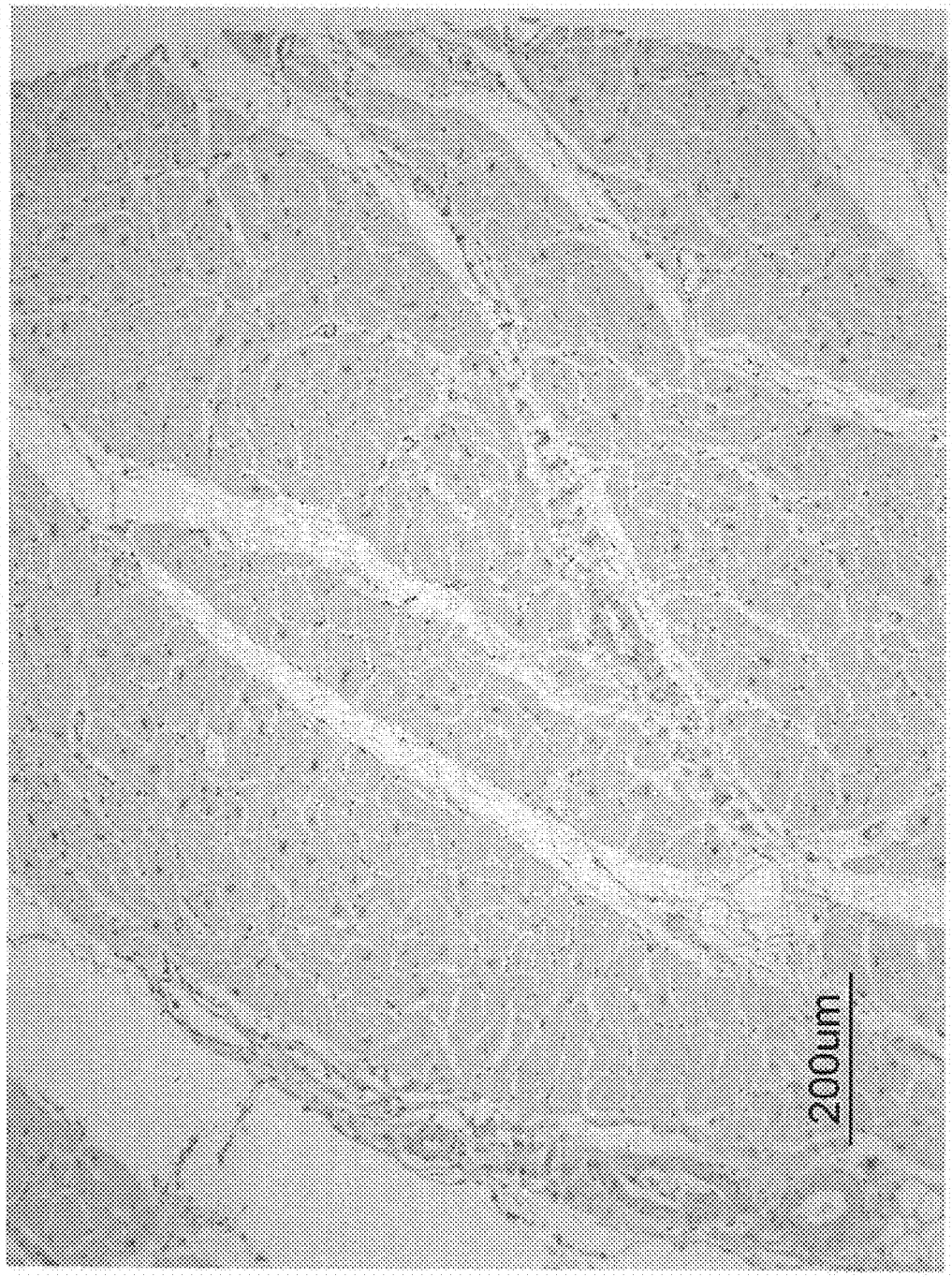
FIG. 39 is a microscopic photograph showing the results of immunohistochemical staining of human normal heart by the S11 antibody.

FIG. 39 is a microscopic photograph showing the results of immunohistochemical staining of human normal heart. The S11 staining is negative.

Figure 40:
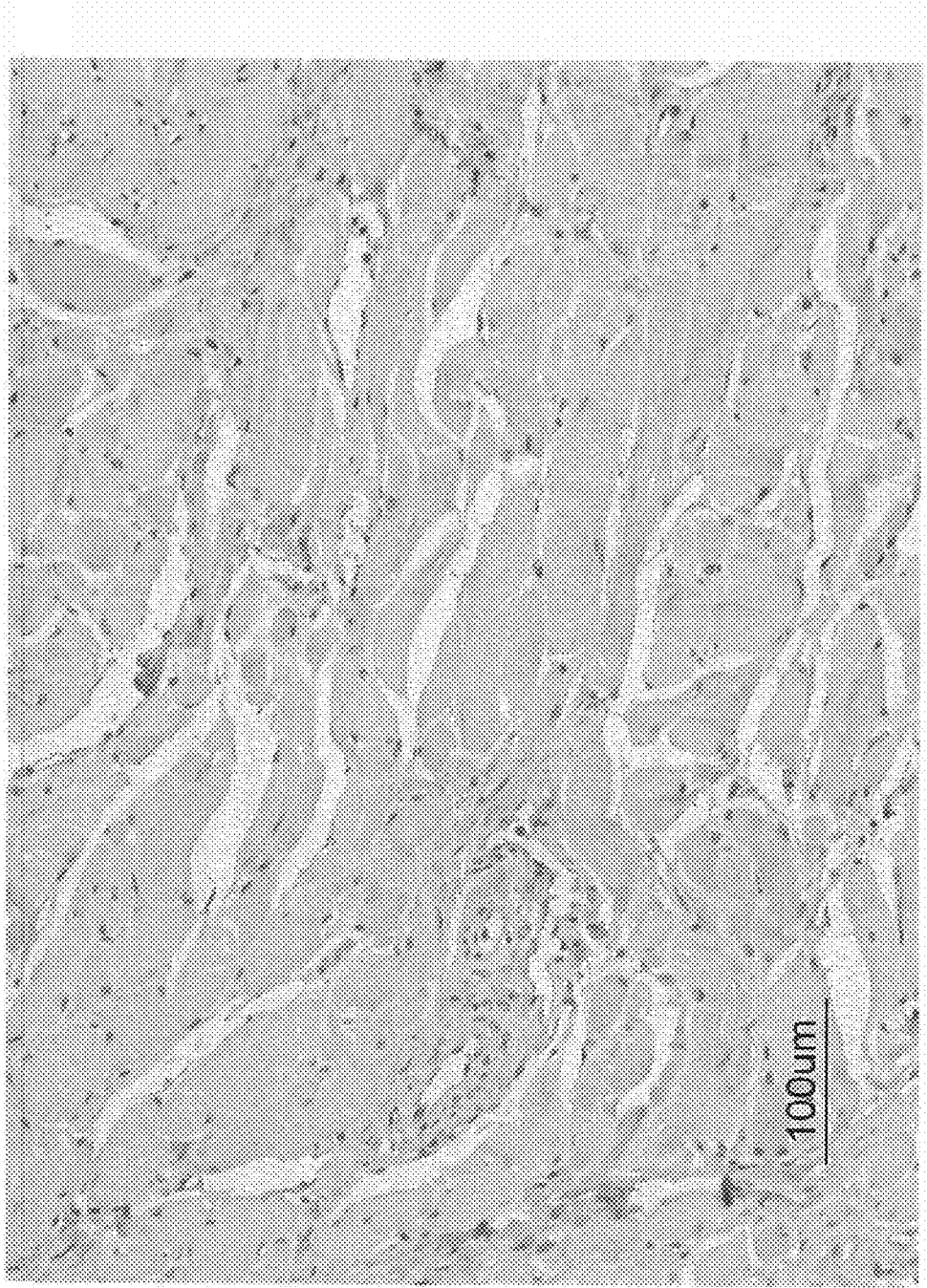
FIG. 40 is a microscopic photograph showing the results of immunohistochemical staining of human normal skeletal muscle by the S11 antibody.

FIG. 40 is a microscopic photograph showing the results of immunohistochemical staining of human normal skeletal muscle. The S11 staining is negative.

The foregoing results indicate that in the immunohistochemical staining with S11, tumor (especially adenocarcinoma) tissues are positive, whereas normal tissues are negative. It is thus demonstrated that PAP2a is specifically expressed in tumor tissues (especially adenocarcinoma tissues) and the anti-PAP2a antibody of the present invention is useful for the detection of PAP2a-positive tumor tissues (diagnosis of tumors) and for the treatment of tumors. Referring to the S11 staining described above, one skilled in the art can readily visually distinguish differences between negative to weakly positive and positive.

Example 9

Cell Growth Inhibition Effect by Saporin-Conjugated Secondary Antibody Using Anti-PAP2a Antibody as an Immunotoxin The materials used in the experiment are as follows.
Has cells (PAP2a-positive cell line)
Anti-PAP2a monoclonal antibody (S11, prepared at a concentration of 1 mg/ml)
Saporin-conjugated anti-mouse IgG, purchased from Mab-ZAP, FUNAKOSHI
10% FCS-containing DMEM
WST-1 (purchased from TAKARA)
96-Well plate (Corning)
The experimental procedures are as follows.
1. Recover Has cells in the exponential phase from a culture dish using a trypsin/EDTA solution.
2. Centrifuge and wash with DMEM.
3. Count the cell number.
4. Adjust to $2 \times 10^5$ cells/ml and dispense by 1 ml each into 15 ml tubes (2 tubes).
5. Add a) 10 μg of isotype control mouse IgG1 and b) 10 μg of anti-PAP2a antibody S11, respectively.
6. React at 4° C. for 30 minutes.
7. Add 10 ml of DMEM, centrifuge and wash to remove an excess of the antibody.

8. Prepare to a cell density of $2 \times 10^4$ cells/ml using DMEM.
9. Seed the cells into a 96-well plate by 100 μl each/well.
10. Add 100 μl/well of saporin-conjugated secondary antibody (Mab-ZAP) diluted to various concentrations.
11. Incubate at 37° C. for 72 hours.
12. Remove the medium by an aspirator and add WST-1 solution by 100 μl each/well.
13. Incubate at 37° C. for 2 hours.
14. Measure absorbance with a plate reader (measured at 415 nm, 655 nm as target)

Figure 41:
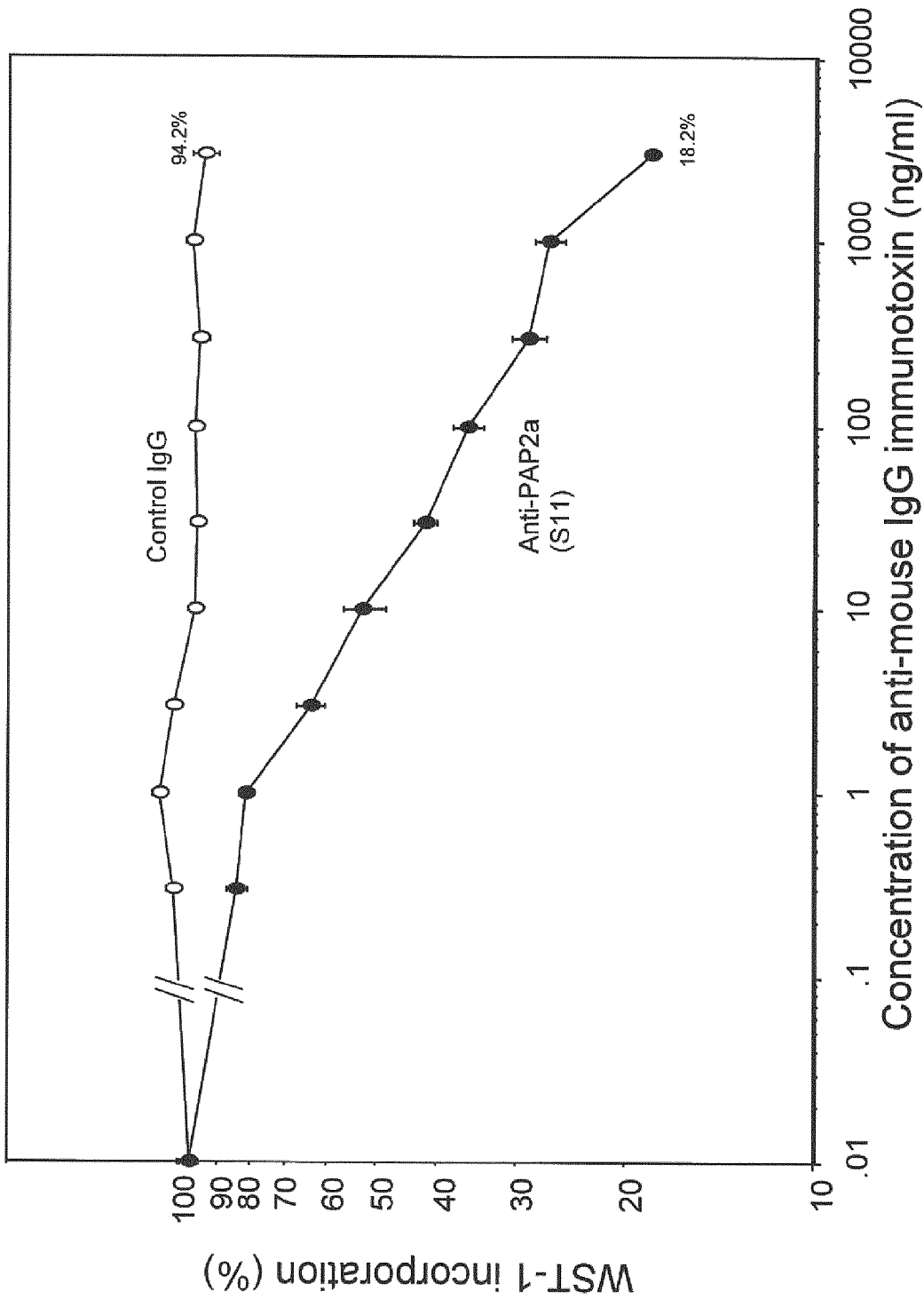
FIG. 41 is a graph showing the results of trials on cell growth inhibition using the anti-PAP2a antibody and the saporin-conjugated secondary antibody.

FIG. 41 is a graph showing the results of trials on Has cytotoxic treatment according to the method described above using anti-PAP2a antibody S11 as an immunotoxin. As shown in this figure, PAP2a-positive cells such as Has cells, etc. can be strongly injured S11-specifically using anti-PAP2a antibody as an immunotoxin. The results demonstrate that PAP2a-targeted immunotherapy using anti-PAP2a antibody has high selectivity to and effective for the treatment of cancer with PAP2a overexpression.

Example 10

Identification of Antigen for Antibody 8A9

The antigen for the 8A9 antibody obtained by the method of screening Adv-FZ33 of the present invention was identified in a manner similar to the procedures described in EXAMPLES 4 through 6. The results are shown in FIGS. 42A to C.

Figure 42A:
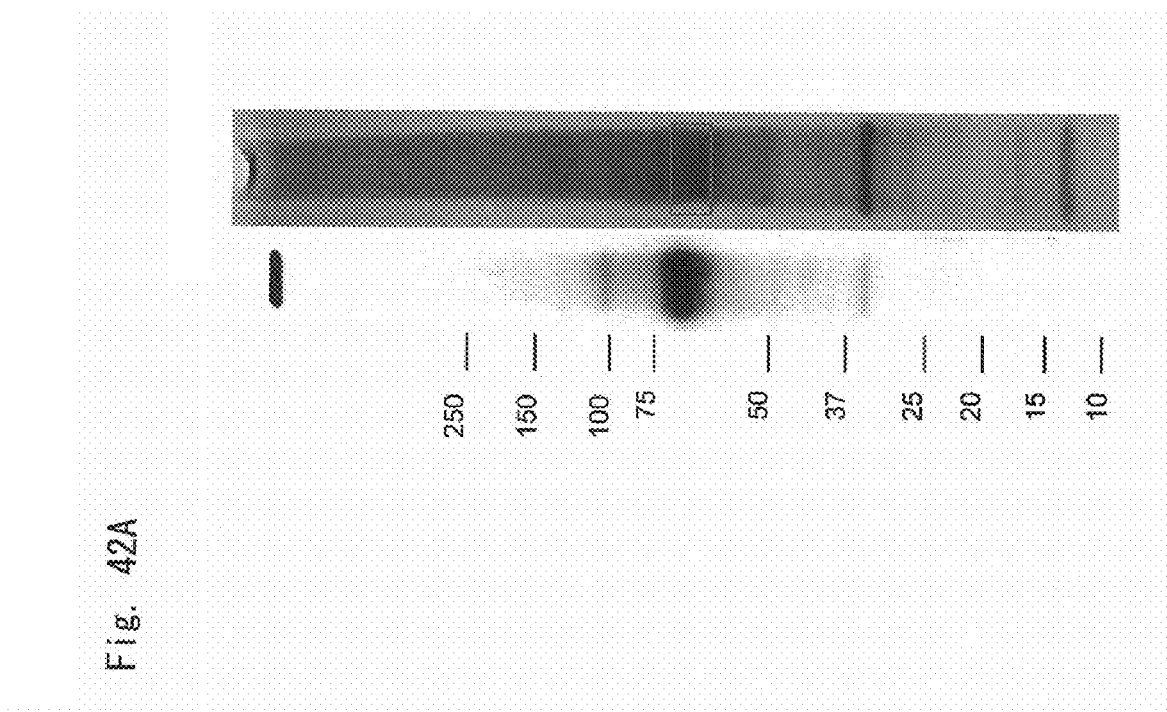
FIG. 42A is an electrophoretic photograph showing the results of immunoprecipitation and silver stain in determining the antigen for the 8A9 antibody.

FIG. 42A shows the results of immunoprecipitation and silver stain. The left lane indicates the results of immunoprecipitation of biotinylated cells by the 8A9 antibody and the right lane indicates the results of SDS-PAGE and silver stain of the immunoprecipitated product. In the figure, the band boxed was cut out and provided for mass spectrometry.

Figure 42B:
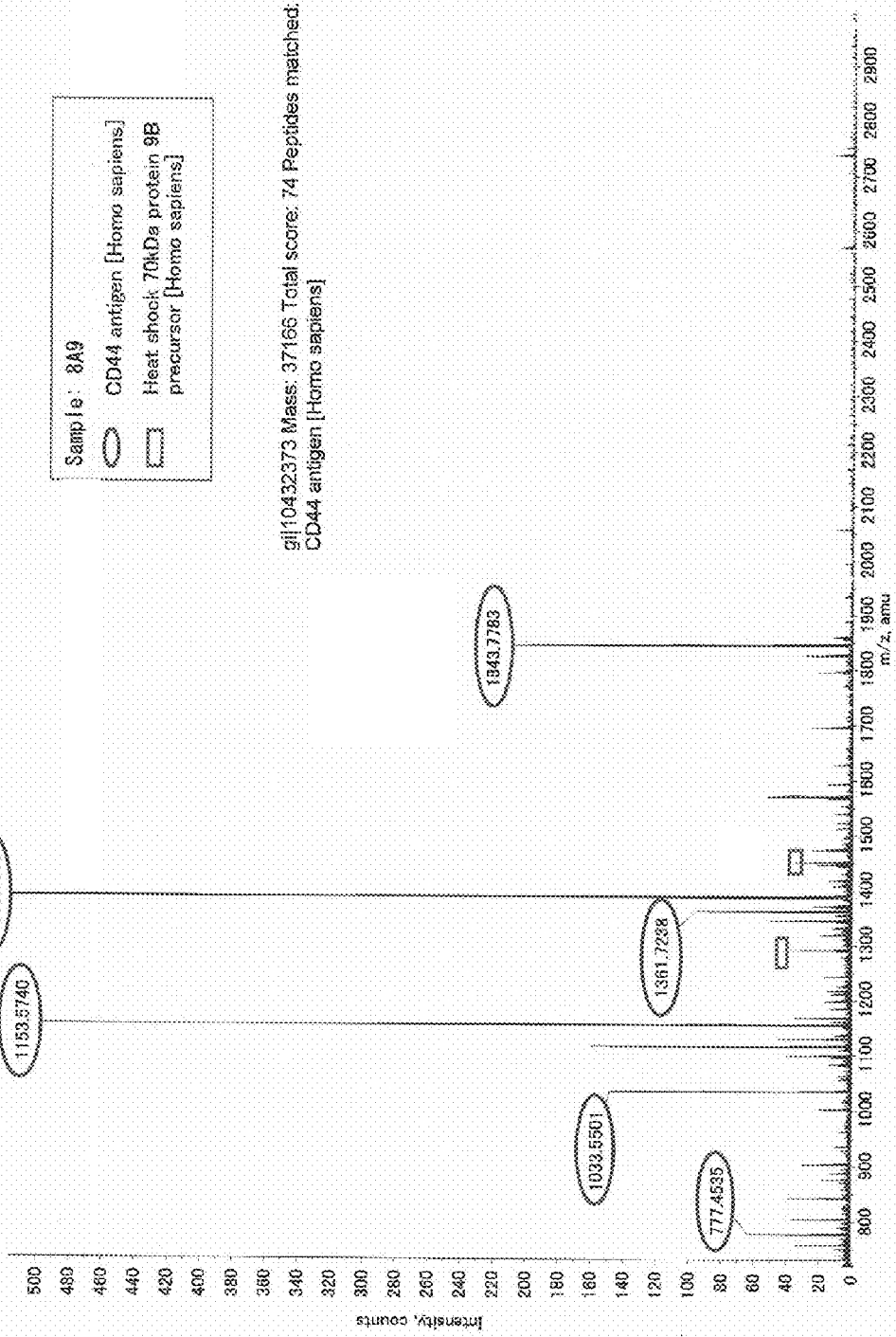
FIG. 42B shows the results of mass spectrometry in determining the antigen for the 8A9 antibody.
Figure 42C:
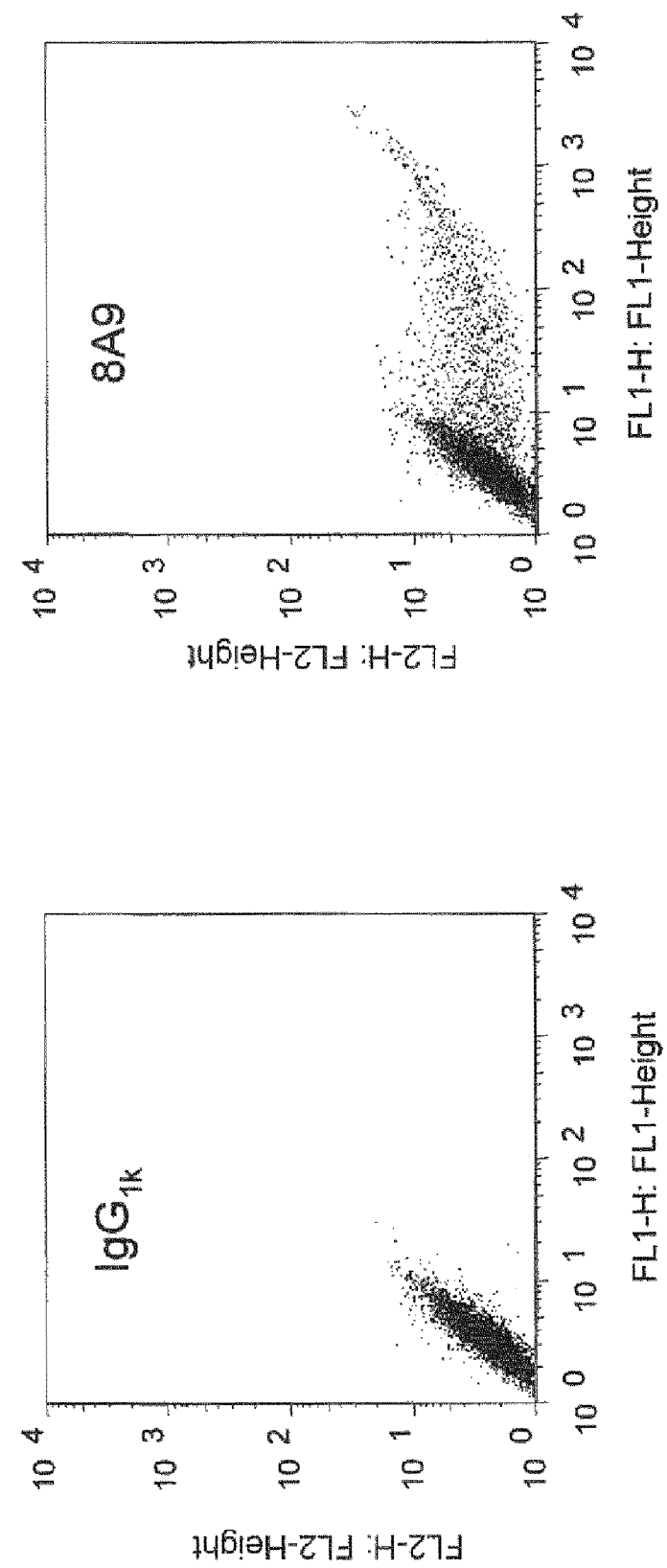
FIG. 42C shows the results of FACS analysis in determining the antigen for the 8A9 antibody.

FIG. 42B shows the results of the mass spectrometry. The amino acid sequence of peptide fragment clarified by the mass spectrometry was applied to homology search on the database and found to coincide with a part of the amino acid sequence of human CD44. Thus, the immunoprecipitated product by the 8A9 antibody was found to be human CD44 antigen molecule.

Furthermore, in order to confirm that human CD44 is an antigen molecule for the 8A9 antibody, the 8A9 antibody was contacted with CHO cells transfected with human CD44 antigen-expressing plasmid vector, followed by FACS analysis. The results are shown in FIG. 42C.

In FIG. 42C, the graph on the right shows the results obtained when the 8A9 antibody was used and the graph on the left shows the results obtained when $IgG_{1\kappa}$ was used as a control. As illustrated in the figure, the 8A9 antibody recognizes CHO cells which overexpress human CD44. It could thus been confirmed that the antigen for the 8A9 antibody is human CD44.

In the experiment illustrated in FIG. 42C, the following materials and method were used.
Materials Chinese hamster ovarian cell line CHO cells (purchased from ATCC) were used. Incubation was performed in an incubator of 37° C. charged with RPMI 1640 culture medium supplemented with 10% FCS, penicillin G potassium (100 U/ml) and streptomycin sulfate (100 μg/ml) in the air containing 5% $CO_2$. Plasmid: pTarget-hCD44 was used.

The cDNA encoding hCD44 was obtained by preparing total RNA from Hela cells (RNeasy®, reagent for RNA preparation:QIAGEN) followed by RT-PCR (SuperScript®II, reverse transcriptase and DNA polymerase: Invitrogen). The primers used were #2187 GCACAGACA-GAATCCCTGCTACC and #2188 GGGGTGGAATGT-GTCTTGGTCTC.

The resulting hCD44 cDNA was ligated to expression vector pTarget® (expression vector, Promega) to give pTarget-hCD44. Plasmid: pCMV-SPORT6-hCD147 was purchased from OpenBiosystem.
Method CHO cells were seeded in a 6-well plate at $5 \times 10^5$/well. On the following day, after it was confirmed that the cells were adhered to the plate, each plasmid was transfected into the cells using LipofectAMINE PLUS® (transfection reagent, Invitrogen) in accordance with the instructions. The cells were recovered 48 hours later. After each primary antibody was reacted at 4° C. for 30 minutes, the cells were washed twice with PBS(−). After anti-mouse-RPE (Dako) as a secondary antibody was reacted at 4° C. for 30 minutes, the cells were washed twice with PBS(−). Thereafter, measurement was carried out on FACSCalibur (BD).

Example 11

Comparison in Transgene Expression Level Using AxCAZ3-Z33 and Several Anti-Human CD44 Antibodies Using the 8A9 antibody prepared as described above and other several anti-human CD44 antibodies together with AxCAZ3-Z33, the transgene expression levels were compared and examined. The materials and method are described below.
Materials Human prostate cancer cell line PC3 (purchased from ATCC) was used as cells. Incubation was performed in an incubator of 37° C. charged with RPMI 1640 culture medium supplemented with 10% FCS, penicillin G potassium (100 U/ml) and streptomycin sulfate (100 μg/ml) in the air containing 5% $CO_2$.

The antibodies used were the three of anti-human CD44 (R & D: 2C5), anti-human CD44 (Santa Cruz: DF1485) and anti-human CD44 (the antibody 8A9 obtained by the Adv-FZ33 screening method of the present invention). Mouse $IgG_{1\kappa}$ isotype control (eBioscience: P3) was used as an isotype control antibody.

AxCAZ3-FZ33 expressing β-galactosidase was used as adenovirus.

Figure 43:
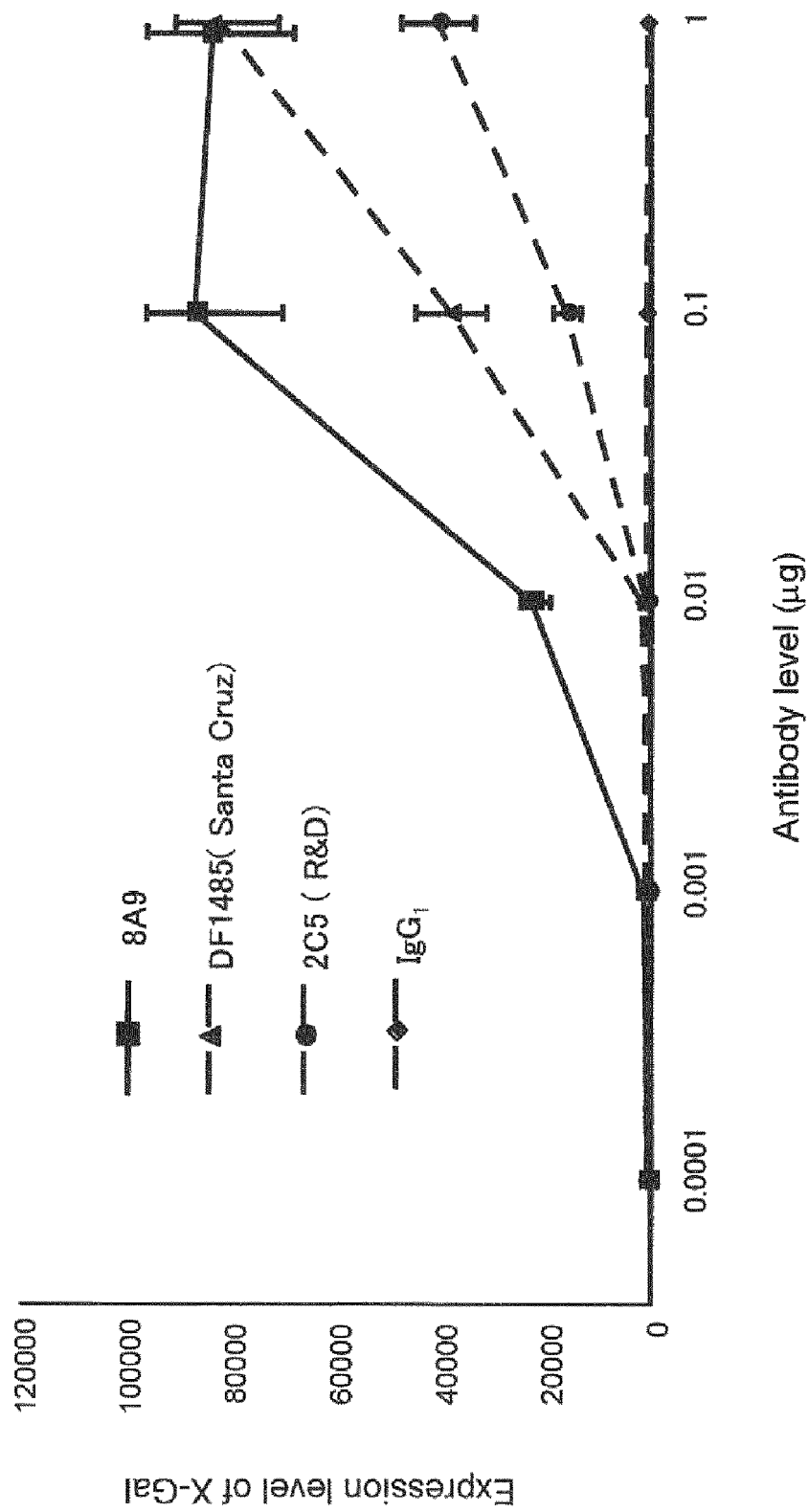
FIG. 43 is a graph showing the comparison in transgene expression level between the 8A9 antibody obtained by the Adv-FZ33 screening method of the present invention and other several anti-human CD44 antibodies, using AxCAZ3-Z33.

Chemiluminescent reporter gene assay was performed using Galacto-Light Plus (Applied Biosystems) in accordance with the instructions.
Method PC3 cells were seeded in a 96-well plate at $1 \times 10^4$/well. On the following day, it was confirmed that the cells were adhered to the plate and the wells were washed once with PBS(−). Next, each antibody was reacted at 4° C. for an hour at concentrations of 0.0001 μg, 0.001 μg, 0.01 μg, 0.1 μg and 1 μg. Thereafter washing was carried out twice with PBS(−). Next, the cells were reacted with AxCAZ3-FZ33 at 1000 vp/cell for 1 hour at 4° C. Thereafter, washing was carried out twice with PBS(−). The cell culture medium was added followed by incubation at 37° C. under 5% $CO_2$. Chemiluminescent reporter gene assay was performed 24 hours later, using Galacto-Light Plus to assay the expression level of β-gal.
Results The results are shown in FIG. 43. When the target gene expression was used as a marker, the anti-human CD44 antibody 8A9 obtained by the method of the present invention exhibited the activity of 5- to 30-fold or more in terms of the $ED_{50}$ values, as compared to commercially available anti-human CD44 antibody. In other words, more excellent antibodies having at least 5- to 30-fold $ED_{50}$ values than commercially available anti-human CD44 antibody could be screened and established by using the method of the present invention.

Example 12

Identification of Antigen for the Antibodies 10D8 and 8D12

The antigen for the 10D8 and 8D12 antibodies obtained by the Adv-FZ33 screening method of the present invention was identified in a manner similar to the procedures described in EXAMPLES 4 to 6. The results are shown in FIGS. 44A to C.

Figure 44A:
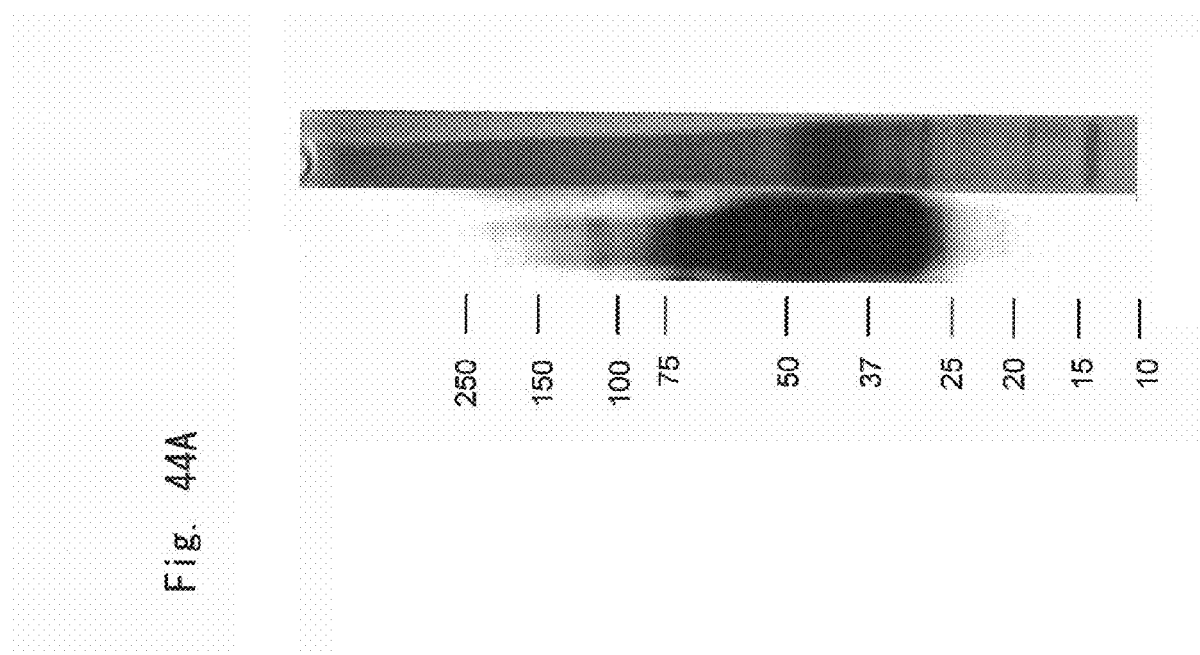
FIG. 44A is an electrophoretic photograph showing the results of immunoprecipitation and silver stain in determining the antigen for the 10D8 antibody.
Figure 44C:
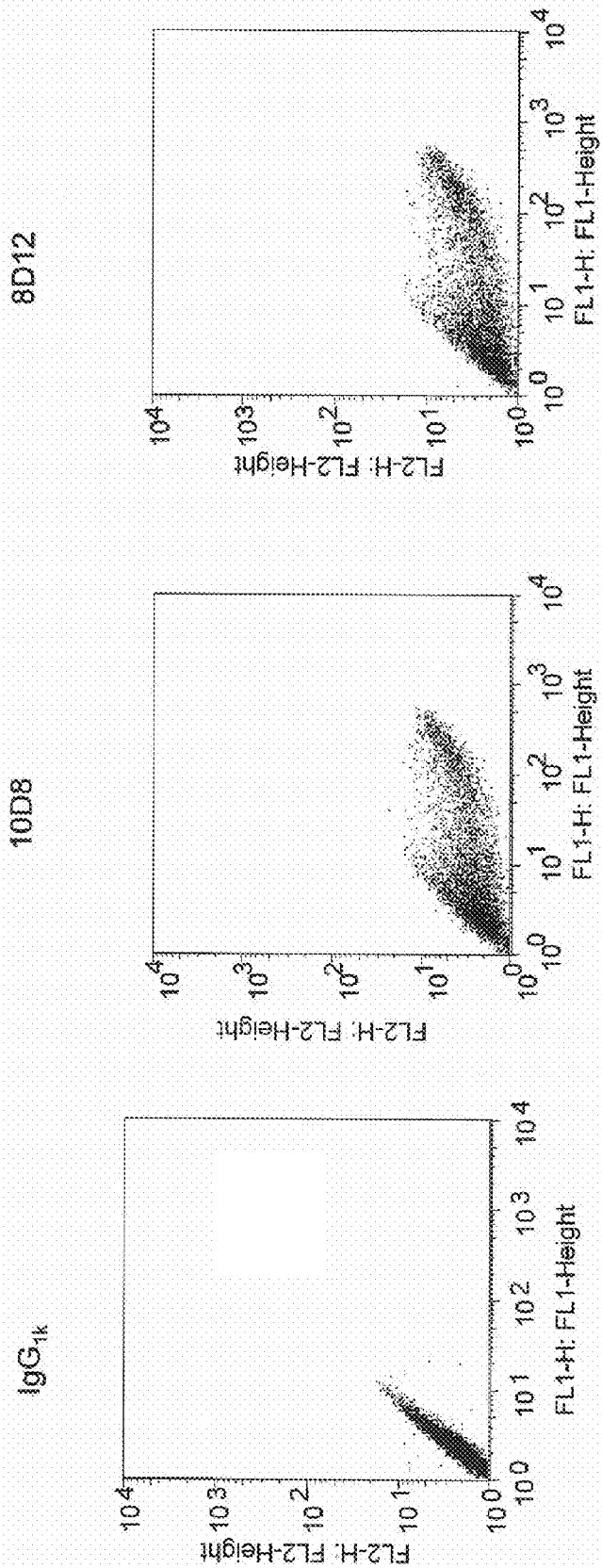
FIG. 44C shows the results of FACS analysis in determining the antigen for the 10D8 and 8D12 antibodies.

FIG. 44A shows the results of immunoprecipitation and silver stain. The left lane indicates the results of immunoprecipitation of biotinylated cells by the 10D8 antibody and the right lane indicates the results of SDS-PAGE and silver stain of the immunoprecipitated product. In the figure, the band boxed was cut out and subjected to mass spectrometry.

FIG. 44B shows the results of the mass spectrometry. The amino acid sequence of peptide fragment clarified by the mass spectrometry was applied to homology search on the database and found to coincide with a part of the amino acid sequence of human CD147. Thus, the immunoprecipitated product by the 10D8 antibody was found to be human CD147 antigen molecule.

Furthermore, in order to confirm that human CD147 is an antigen molecule for the 10D8 (and 8D12) antibodies, the 10D8 (and 8D12) antibodies were contacted with CHO cells transfected with human CD147 antigen-expressing plasmid vector, followed by FACS analysis. The results are shown in FIG. 44C.

In FIG. 44C, the graph on the center shows the results obtained when the 10D8 antibody was used, the graph on the right shows the results obtained when the 8D12 antibody was used and the graph at the left shows the results obtained when $IgG_{1k}$ was used as a control. As illustrated in the figure, both the 10D8 and 8D12 antibodies recognize human CD147-overexpressing CHO cells. It could thus been confirmed that the antigen for the 10D8 and 8D12 antibodies is human CD147.

In the experiment illustrated in FIG. 44C, the following materials and method were used.

Materials

Chinese hamster ovarian cell line CHO cells (purchased from ATCC) were used. Incubation was performed in an incubator of 37° C. charged with RPMI 1640 culture medium supplemented with 10% FCS, penicillin G potassium (100 U/ml) and streptomycin sulfate (100 µg/ml) in the air containing 5% $CO_2$. Plasmid: pCMV-SPORT6-hCD147 was purchased from OpenBiosystem.

Method

CHO cells were seeded in a 6-well plate at $5 \times 10^5$/well. On the following day, it was confirmed that the cells were adhered to the plate and each plasmid was transfected into the cells using LipofectAMINE PLUS® (transfection reagent, Invitrogen) in accordance with the instructions. The cells were recovered 48 hours later. After each primary antibody was reacted at 4° C. for 30 minutes, the cells were washed twice with PBS(−). After anti-mouse-RPE (Dako) as a secondary antibody was reacted at 4° C. for 30 minutes, the cells were washed twice with PBS(−). Thereafter, measurement was carried out on FACSCalibur (BD).

Example 13

Comparison in Transgene Expression Level Using AxCAZ3-Z33 and Several Anti-Human CD147 Antibodies Using the 10D8 and 8D12 antibodies prepared as described above and other several anti-human CD147 antibodies together with AxCAZ3-Z33, the transgene expression levels were compared and examined. The materials and method are described below.

Materials

Human prostate cancer cell line PC3 (purchased from ATCC) was used as cells. Incubation was performed in an incubator of 37° C. charged with RPMI 1640 culture medium supplemented with 10% FCS, penicillin G potassium (100 U/ml) and streptomycin sulfate (100 µg/ml) in the air containing 5% $CO_2$.

The antibodies used were the four of anti-human CD147 (CHEMICON: 1G6.2), anti-human CD147 (Abcam: ab666), anti-human CD147 (the antibody 8D12 obtained by the Adv-FZ33 screening method of the present invention) and anti-human CD147 (the antibody 10D8 obtained by the Adv-FZ33 screening method of the present invention). Mouse $IgG_{1K}$ isotype control (eBioscience: P3) was used as an isotype control antibody.

AxCAZ3-FZ33 expressing β-galactosidase was used as adenovirus.

Chemiluminescent reporter gene assay was performed using Galacto-Light Plus (Applied Biosystems) in accordance with the instructions.

Method

PC3 cells were seeded in a 96-well plate at $1 \times 10^4$/well. On the following day, it was confirmed that the cells were adhered to the plate and the wells were washed once with PBS(−). Next, each antibody was reacted at 4° C. for an hour at concentrations of 0.0001 µg, 0.001 µg, 0.01 µg, 0.1 µg and 1 µg. Thereafter washing was carried out twice with PBS(−). Next, AxCAZ3-FZ33 was reacted at 4° C. for an hour at 1000 vp/cell. Thereafter washing was carried out twice with PBS (−). The cell culture medium was added followed by incubation at 37° C. under 5% $CO_2$. Chemiluminescent reporter gene assay was performed 24 hours later, using Galacto-Light Plus to assay the expression level of β-gal.

Results

Figure 45:
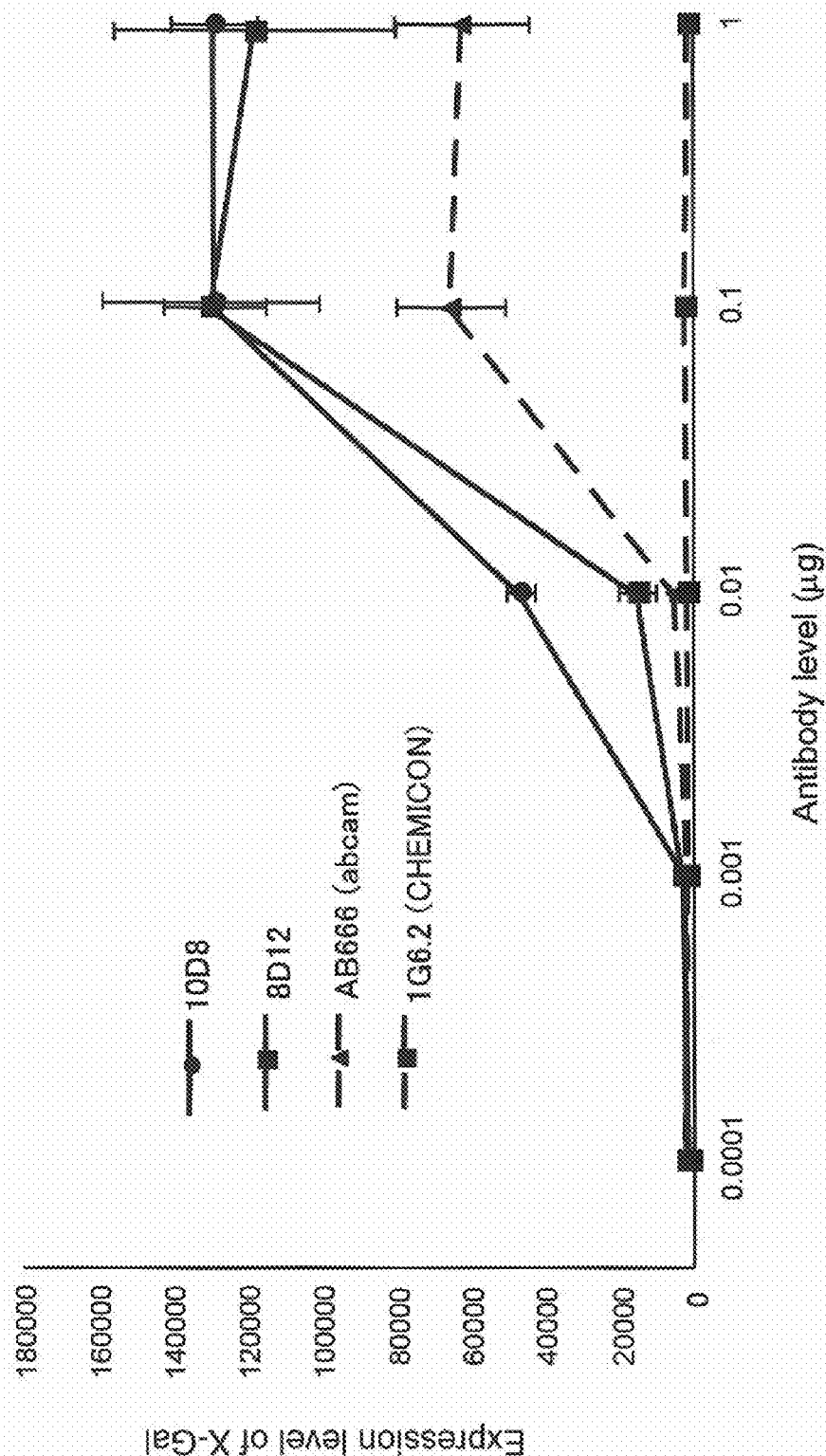
FIG. 45 is a graph showing the comparison in lacZ gene expression level between the 10D8 and 8D12 antibodies obtained by the Adv-FZ33 screening method of the present invention and other several anti-human CD147 antibodies, using AxCAZ3-Z33.

The results are shown in FIG. 45. When the target gene expression was used as a marker, the anti-human CD147 antibodies 10D8 and 8D12, obtained by the Adv-FZ33 screening method of the present invention exhibited markedly high activities, as compared to commercially available anti-human CD147 antibody. In other words, more markedly excellent antibodies than the commercially available anti-human CD147 antibody could be screened and established by using the Adv-FZ33 screening method of the present invention.

The 1G6.2 antibody (CHEMICON) was an antibody having little activity when the target gene expression was used as a marker. The AB666 antibody (Abcam) showed almost the same properties as the antibody obtained by the Adv-FZ33 screening method of the present invention in terms of the $ED_{50}$ values, and even though the antibody level was increased, the maximum activity (expression level) hit its peak and only reached the activity level of about 50% of the anti-human CD147 antibodies 10D8 and 8D12 obtained by the method of the present invention.

Comparison between the anti-human CD147 antibodies 10D8 and 8D12 obtained by the Adv-FZ33 screening method of the present invention indicates that the 10D8 antibody provides a quicker initial rise in its activity than the 8D12 antibody, showing that the 10D8 antibody has a higher target activity.

Example 14

Comparison in Efficiency of Gene Transfer by Adv-FZ33 Using Mouse Anti-CEA Monoclonal Antibodies The present inventors compared the efficiency of gene transfer by Adv-FZ33 using various mouse anti-CEA (human carcinoembryonic antigen) monoclonal antibodies. The procedures are described below.

One day before infection (Day-1), MKN-45 cell line was seeded in a 6-well plate at $1 \times 10^5$ cells/well. On Day 0, various mouse anti-CEA monoclonal antibodies provided by Dr. Kuroki (Fukuoka University) or commercially available were adjusted to the concentration of 3 µg/ml with serum-free RPMI-1640 and added to the various cells in a volume of 1000 µl. For positive control, human anti-CEA antibody C2-45 was used. For isotype control, mouse IgG1 (eBioscience, clone P3), mouse IgG2a (eBioscience, clone eBM2a), mouse IgG2b (eBioscience, clone eBMG2b) and mouse IgG3 (BD Pharmingen, Cat No 553484) were used, respectively. After addition of the antibody, the cells were washed twice with 1000 µl of serum-free RPMI-1640. Next, Ax3CAEGFP-FZ33 was diluted in serum-free RPMI-1640 to the concentration of 1000 VP/cell and the dilution was added to the various cells in a volume of 1000 µl, followed by incubation at 37° C. for an hour to effect infection. After incubation, the cells were washed twice with 1000 µl of serum-free PRMI-1640 and further incubated in RPMI-1640 supplemented with 10% FBS for 24 hours. On Day 1, the GFP activity was assayed on a FACSCalibur.

Figure 46:
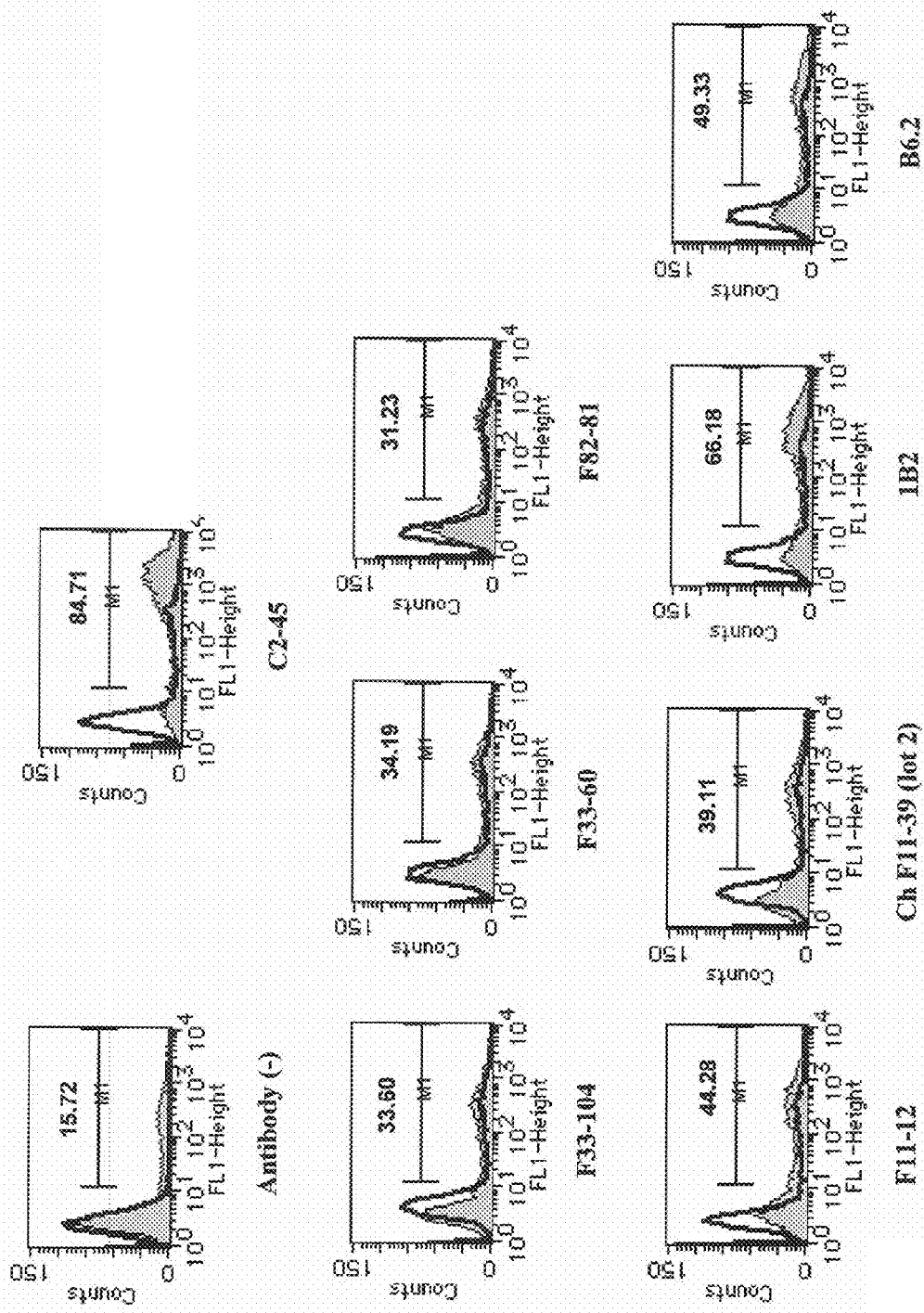
FIG. 46 is graphs showing the measurement results on FACSCalibur.

FIG. 46 is graphs showing the results of measurement on FACSCalibur. The gene transfer efficiency could be enhanced both with mouse anti-CEA antibodies and chimeric antibodies, as compared to control. Among others, C2-45 exhibited the gene transfer efficiency of EGFP as high as 10 to 100 times more than the other mouse anti-CEA monoclonal antibodies.

Figure 47:
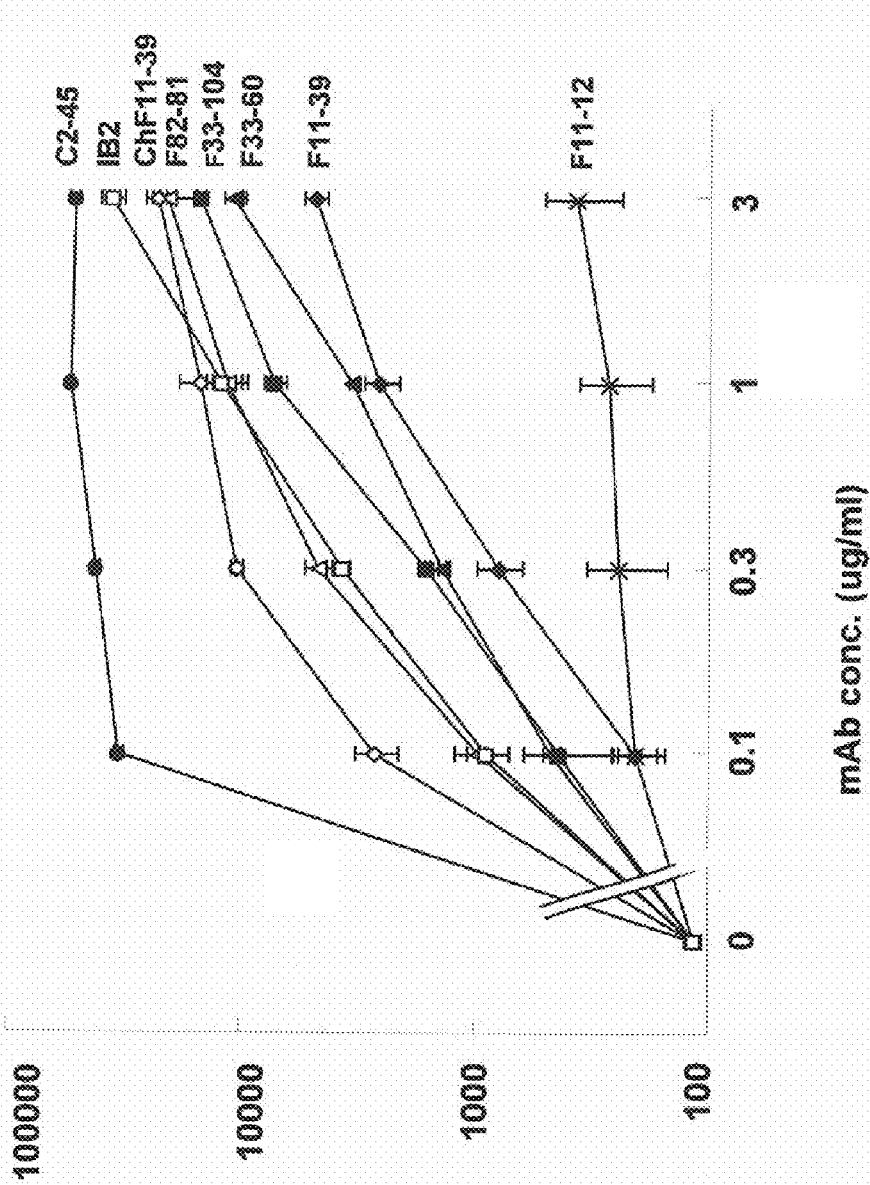
FIG. 47 is a graph showing the comparison in gene expression levels of β-galactosidase (β-gal expression levels) when the gene transfer was performed in CHO cells to express CEA, using various anti-CEA antibodies and Adv-FZ33 lacZ adenovirus.

FIG. 47 is a graph showing the comparison of lacZ gene expression levels when gene transfer was performed in CHO cells to express CEA, using various anti-CEA antibodies and Adv-FZ33 lacZ adenovirus. The gene transfer efficiency could be enhanced both with mouse anti-CEA antibodies and chimeric antibodies, as compared to control. In particular, C2-45 exhibited the gene transfer efficiency of EGFP as high as 10 to 100 times more than the other anti-CEA monoclonal antibodies. It is thus demonstrated that by using the assay method, antibodies can be compared in terms of activity with extremely high S/N ratio (high signal/noise ratio) over a wide dynamic range. It was found that the method provides comparison in the activities of antibodies with extremely high S/N ratio (high signal/noise ratio) over a wide dynamic range, as compared to conventional methods such as FACS, ELISA, etc.

The results shown in FIG. 46 and FIG. 47 also demonstrate that markedly excellent "targeted antibody with high efficiency" can be distinguished and selected from other antibodies with average activities, by using genetically modified Adv (Ax3CAEGFP-FZ33) carrying the IgG binding sequence in the fiber domain and encoding a marker gene such as EGFP gene, as described above. As such, the Adv-FZ33 screening method of the present invention is an assay method having a high S/N ratio (high signal/noise ratio) over a wide dynamic range, which can select particularly excellent "targeted antibodies with high efficiency" as compared to conventional methods (e.g., ELISA, etc.).

The mouse anti-CEA monoclonal antibodies used in the experiments, whose results are shown in FIGS. 46 and 47 are described below.

1. F33-104 (Ikeda S. et al, Mol. Immunol., 29: 229-240, 1992., Kuroki M. et al, Hybridoma, 11:391-407, 1992.)
   Class: IgG1 (k)
   Affinity constant: $3.5 \times 10^{(+8)}$/M
   OD=14.0 (Ab Conc.=10.0 mg/ml)
   Vol.=0.5 ml
   Total Ab=5.0 mg
   Buffer: 0.01 M BBS, pH 8.0

2. F33-60 (Ikeda S. et al, Mol. Immunol., 29: 229-240, 1992., Kuroki M. et al, Hybridoma, 11:391-407, 1992.)
   Class: IgG2a (k)
   Affinity constant: $3.4 \times 10^{(+8)}$/M
   OD=14.0 (Ab Conc.=10.0 mg/ml)
   Vol.=0.5 ml
   Total Ab=5.0 mg
   Buffer: 0.01 M BBS, pH 8.0

3. F82-81 (Ikeda S. et al, Mol. Immunol., 29: 229-240, 1992., Kuroki M. et al, Hybridoma, 11:391-407, 1992.)
   Class: IgG2b (k)
   Affinity constant: $9.5 \times 10^{(+8)}$/M
   OD=14.0 (Ab Conc.=10.0 mg/ml)
   Vol.=0.5 ml
   Total Ab=5.0 mg
   Buffer: 0.01 M BBS, pH 8.04. F11-12 (Ikeda S. et al, Mol. Immunol., 29: 229-240, 1992., Kuroki M. et al, Hybridoma, 11:391-407, 1992.)
   Class: IgG3 (k)
   Affinity constant: $11.2 \times 10^{(+8)}$/M
   OD=14.0 (Ab Conc.=10.0 mg/ml)
   Vol.=0.5 ml
   Total Ab=5.0 mg
   Buffer: 0.01 M BBS, pH 8.0

5. Ch F11-39 (Lot 2) (Arakawa F. et al, Hybridoma, 12: 365-379, 1993.)
   Class: ibid.
   Affinity constant: ibid.
   OD=2.10 (Ab Conc.=1.5 mg/ml)
   Vol.=0.5 ml
   Total Ab=0.75 mg
   Buffer: 0.01 M BBS, pH 8.0

6. IB2 (purchased from IBL: lot No. 9G-717)
   Class: IgG2a
   Ab Conc.=1 mg/ml

7. B6.2/CD66 (purchased from BD PharMingen: Catalog No. 551355)
   Class: IgG1
   Ab Conc. 0.5 mg/ml

INDUSTRIAL APPLICABILITY

The antibodies of the present invention are useful in use of target therapy for PAP2a-positive cancers (especially metastatic carcinoma, adenocarcinoma) including pancreatic cancer, lung cancer, prostate cancer, ovarian cancer and breast cancer. In particular, when the antibody is used in combination with fiber-modified adenovirus so as to bind to the Fc domain of the antibody, the multiplicity of adenoviral infection is enhanced. Thus, the antibodies are useful for targeted gene delivery using the fiber-modified adenovirus described above.

The antibodies are also useful as targeted antibodies for various purposes including antibody therapy using conjugates for anti-cancer agents or ADCC.

The cancer-specific antigens identified by the method of the present invention are useful not only as diagnostic markers but also as the target for target therapy, or as components of vaccine preparations, etc.

The antibodies of the present invention make immunological trials including immunoprecipitation, FACS, etc. easy and enable to stain tissues and are useful for both treatment and diagnosis of cancer.

The method for identifying the cancer-specific antigens of the present invention and their antibodies is useful for systematic search of the combination of molecule candidates, which become the target in drug targeting therapy, and their antibodies.

Moreover, the method for screening monoclonal antibodies for desired antigens of the present invention is useful for yielding highly efficient antibodies which can remarkably enhance the targeting efficiency of therapeutic substances toward target cells, as compared to conventional methods.

The invention claimed is:

1. A method for diagnosing pancreatic cancer in a patient, wherein said pancreatic cancer is characterized by overexpression of PAP2a comprising:
   (a) measuring the level of expression of the gene encoding PAP2a in a tissue sample that is suspected of comprising the pancreatic cancer cells and which is obtained from the patient;
   (b) comparing the level of expression measured in the tissue sample to the level of expression of the gene encoding PAP2a from corresponding normal cells or tissues of the patient and/or a control subject; and
   (c) determining the presence of the pancreatic cancer in the patient when the level of expression of PAP2a in the tissue sample is higher than the level of expression of PAP2a from the corresponding normal cells or tissues of the patient and/or a control subject.

2. The method according to claim 1, wherein the measuring comprises immunologically measuring the level of PAP2a protein in the tissue sample using an anti-PAP2a antibody.

3. The method according to claim 2, which comprises:
   the step of contacting the tissue sample with the anti-PAP2a antibody, and,
   the step of measuring the binding of the anti-PAP2a antibody to the PAP2a in the tissue sample.

4. The method according to claim 2, which follows an immunoassay selected from the group consisting of western blot assay, radioimmunoassay (RIA), enzyme-linked immunosorbent assay (ELISA), sandwich immunoassay, fluorescence immunoassay (FIA), time-resolved fluorescence immunoassay (TRFIA), enzyme-linked immunoassay (EIA), luminescence immunoassay (LIA), electrochemiluminescence immunoassay (ECLIA), latex agglutination assay, immunoprecipitation assay, precipitation reaction assay, gel-diffusion precipitation reaction assay, immunodiffusion assay, agglutination assay, complement fixation assay, immunoradiometric assay, fluoroimmunoassay and protein A immunoassay.

5. The method according to claim 2, wherein the anti-PAP2a antibody is an anti-PAP2a antibody produced from a hybridoma of Accession Number FERM P-20499 or a hybridoma of Accession Number FERM P-20498.

* * * * *

SEQUENCE LISTING

```
<160> NUMBER OF SEQ ID NOS: 37

<210> SEQ ID NO 1
<211> LENGTH: 284
<212> TYPE: PRT
<213> ORGANISM: Homo sapiens

<400> SEQUENCE: 1

Met Phe Asp Lys Thr Arg Leu Pro Tyr Val Ala Leu Asp Val Leu Cys
1               5                   10                  15

Val Leu Leu Ala Gly Leu Pro Phe Ala Ile Leu Thr Ser Arg His Thr
            20                  25                  30

Pro Phe Gln Arg Gly Val Phe Cys Asn Asp Glu Ser Ile Lys Tyr Pro
        35                  40                  45

Tyr Lys Glu Asp Thr Ile Pro Tyr Ala Leu Leu Gly Gly Ile Ile Ile
    50                  55                  60

Pro Phe Ser Ile Ile Val Ile Ile Leu Gly Glu Thr Leu Ser Val Tyr
65                  70                  75                  80

Cys Asn Leu Leu His Ser Asn Ser Phe Ile Arg Asn Asn Tyr Ile Ala
                85                  90                  95

Thr Ile Tyr Lys Ala Ile Gly Thr Phe Leu Phe Gly Ala Ala Ala Ser
            100                 105                 110

Gln Ser Leu Thr Asp Ile Ala Lys Tyr Ser Ile Gly Arg Leu Arg Pro
        115                 120                 125

His Phe Leu Asp Val Cys Asp Pro Asp Trp Ser Lys Ile Asn Cys Ser
    130                 135                 140

Asp Gly Tyr Ile Glu Tyr Tyr Ile Cys Arg Gly Asn Ala Glu Arg Val
145                 150                 155                 160

Lys Glu Gly Arg Leu Ser Phe Tyr Ser Gly His Ser Ser Phe Ser Met
                165                 170                 175

Tyr Cys Met Leu Phe Val Ala Leu Tyr Leu Gln Ala Arg Met Lys Gly
            180                 185                 190

Asp Trp Ala Arg Leu Leu Arg Pro Thr Leu Gln Phe Gly Leu Val Ala
        195                 200                 205

Val Ser Ile Tyr Val Gly Leu Ser Arg Val Ser Asp Tyr Lys His His
    210                 215                 220

Trp Ser Asp Val Leu Thr Gly Leu Ile Gln Gly Ala Leu Val Ala Ile
225                 230                 235                 240

Leu Val Ala Val Tyr Val Ser Asp Phe Phe Lys Glu Arg Thr Ser Phe
                245                 250                 255

Lys Glu Arg Lys Glu Glu Asp Ser His Thr Thr Leu His Glu Thr Pro
            260                 265                 270
```

Thr Thr Gly Asn His Tyr Pro Ser Asn His Gln Pro
        275                 280

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccgcaattgt taattaagga tccccatcat caataatata cctta            45

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccatcgattt aaatagatct gcggccctag acaaatatta cgcgc            45

<210> SEQ ID NO 4
<211> LENGTH: 401
<212> TYPE: DNA
<213> ORGANISM: Artificial Sequence
<220> FEATURE:
<223> OTHER INFORMATION: Description of Artificial Sequence: Synthetic
      401bp PCR fragment sequence

<400> SEQUENCE: 4
ccgcaattgt taattaagga tccccatcat caataatata ccttattttg gattgaagcc    60
aatatgataa tgaggggtg gagtttgtga cgtggcgcgg ggcgtgggaa cggggcgggt    120
gacgtagtag tgtggcggaa gtgtgatgtt gcaagtgtgg cggaacacat gtaagcgacg    180
gatgtggcaa aagtgacgtt tttggtgtgc gccggtgtac acaggaagtg acaattttcg    240
cgcggtttta ggcggatgtt gtagtaaatt tgggcgtaac cgagtaagat ttggccattt    300
tcgcgggaaa actgaataag aggaagtgaa atctgaataa ttttgtgtta ctcatagcgc    360
gtaatatttg tctagggccg cagatctatt taaatcgatg g                      401

<210> SEQ ID NO 5
<211> LENGTH: 166
<212> TYPE: DNA
<213> ORGANISM: Artificial Sequence
<220> FEATURE:
<223> OTHER INFORMATION: Description of Artificial Sequence: Synthetic
      HI loop fragment sequence

<400> SEQUENCE: 5
tgtgactgcc gcggagactg tttctgccca agtgcatact ctatgtcatt tcatgggac    60 tggtctggcc acaactacat taatgaaata tttgccacct cgagttacac ttttcatac    120 attgcccaag aataaggatc cacgcgtgtc gacaagaata aagaat                  166

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 6
cggggtacca atatctggaa cagttcaaag tgctcat                                37

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cggaattcgg cgcgccaccg gtttcctgtg taccgtttag tgtaatg                     47

<210> SEQ ID NO 8
<211> LENGTH: 314
<212> TYPE: DNA
<213> ORGANISM: Artificial Sequence
<220> FEATURE:
<223> OTHER INFORMATION: Description of Artificial Sequence: Synthetic
      314bp PCR fragment sequence

<400> SEQUENCE: 8
cggggtacca atatctggaa cagttcaaag tgctcatctt attataagat ttgacgaaaa       60
tggagtgcta ctaaacaatt ccttcctgga cccagaatat ggaacttta gaaatggaga      120 tcttactgaa ggcacagcct atacaaacgc tgttggattt atgcctaacc tatcagctta     180
tccaaaatct cacggtaaaa ctgccaaaag taacattgtc agtcaagttt acttaaacgg     240
agacaaaact aaacctgtaa cactaaccat tacactaaac ggtacacagg aaaccggtgg     300
cgcgccgaat tccg                                                       314

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgaattccg ctagcgacac aactccaagt gcatactcta tgtcattttc at              52

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atatggtacc gggaggtggt gaatta                                           26

<210> SEQ ID NO 11
<211> LENGTH: 974
<212> TYPE: DNA
<213> ORGANISM: Artificial Sequence
<220> FEATURE:
<223> OTHER INFORMATION: Description of Artificial Sequence: Synthetic
      974bp PCR fragment sequence

<400> SEQUENCE: 11
ccgaattccg ctagcgacac aactccaagt gcatactcta tgtcattttc atgggactgg      60
```

```
tctggccaca actacattaa tgaaatattt gccacctcga gttacacttt tcatacatt      120
gcccaagaat aaggatccac gcgtgtcgac aagaataaag aatcgtttgt gttatgtttc     180
aacgtgttta tttttcaatt gcagaaaatt tcaagtcatt tttcattcag tagtatagcc    240
ccaccaccac atagcttata cagatcaccg taccttaatc aaactcacag aaccctagta    300
ttcaacctgc cacctccctc caacacacag agtacacag tcctttctcc ccggctggcc     360
ttaaaaagca tcatatcatg ggtaacagac atattcttag gtgttatatt ccacacggtt    420
tcctgtcgag ccaaacgctc atcagtgata ttaataaact ccccgggcag ctcgcttaag    480
ttcatgtcgc tgtccagctg ctgagccaca ggctgctgtc aacttgcgg ttgctcaacg     540
ggcggcgaag gggaagtcca cgcctacatg ggggtagagt cataatcgtg catcaggata    600
gggcggtggt gctgcagcag cgcgcgaata aactgctgcc gccgccgctc cgtcctgcag    660
gaatacaaca tggcagtggt ctcctcagcg atgattcgca ccgcccgcag catgagacgc    720
cttgtcctcc gggcacagca gcgcaccctg atctcactta aatcagcaca gtaactgcag    780
cacagcacca caatattgtt caaaatccca cagtgcaagg cgctgtatcc aaagctcatg    840
gcggggacca cagaacccac gtggccatca taccacaagc gcaggtagat taagtggcga    900
cccctcataa acacgctgga cataaacatt acctcttttg gcatgttgta attcaccacc    960
tcccggtacc atat                                                      974

<210> SEQ ID NO 12
<211> LENGTH: 136
<212> TYPE: DNA
<213> ORGANISM: Artificial Sequence
<220> FEATURE:
<223> OTHER INFORMATION: Description of Artificial Sequence: Synthetic
      136bp fragment sequence

<400> SEQUENCE: 12
gaattccgct agcgcacaa ctccaagtgc atactctatg tcattttcat gggactggtc      60
tggccacaac tacattaatg aaatatttgc cacctcgagt tacactttt catacattgc     120 ccaagaataa ggatcc                                                    136

<210> SEQ ID NO 13
<211> LENGTH: 439
<212> TYPE: DNA
<213> ORGANISM: Artificial Sequence
<220> FEATURE:
<223> OTHER INFORMATION: Description of Artificial Sequence: Synthetic
      439bp PCR fragment sequence

<400> SEQUENCE: 13
ggtaccaata tctggaacag ttcaaagtgc tcatcttatt ataagatttg acgaaaatgg     60
agtgctacta aacaattcct tcctggaccc agaatattgg aactttagaa atggagatct    120
tactgaaggc acagcctata caaacgctgt tggatttatg cctaacctat cagcttatcc    180
aaaatctcac ggtaaaactg ccaaaagtaa cattgtcagt caagtttact taaacggaga    240
caaaactaaa cctgtaacac taaccattac actaaacggt acacaggaaa ccggtggcgc    300
gccgaattcc gctagcgaca caactccaag tgcatactct atgtcatttt catgggactg    360
gtctggccac aactacatta atgaaatatt gccacctcg agttacactt tttcatacat    420
tgcccaagaa taaggatcc                                                 439

<210> SEQ ID NO 14
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 14
gaaaccggtc tcatcaagtt taacatgcag cagcagcgcc gcttttac            48

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtcgctagca tctatgtcgt cgcgaatgct cttaatcttg gcgttgcg            48

<210> SEQ ID NO 16
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgcagcagc agcgccgctt ttacgaggcc ttgcacgacc ccaacctgaa cgaggagcag    60
cgcaacgcca agattaagag cattcg                                         86

<210> SEQ ID NO 17
<211> LENGTH: 132
<212> TYPE: DNA
<213> ORGANISM: Artificial Sequence
<220> FEATURE:
<223> OTHER INFORMATION: Description of Artificial Sequence: Synthetic
      132 PCR fragment sequence

<400> SEQUENCE: 17
gaaaccggtc tcatcaagtt taacatgcag cagcagcgcc gcttttacga ggccttgcac    60
gaccccaacc tgaacgagga gcagcgcaac gccaagatta agagcattcg cgacgacata   120
gatgctagcg ac                                                       132

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide sequence encoded by the 132bp PCR
      fragment sequence

<400> SEQUENCE: 18

Glu Thr Gly Leu Ile Lys Phe Asn Met Gln Gln Gln Arg Arg Phe Tyr
1               5                   10                  15

Glu Ala Leu His Asp Pro Asn Leu Asn Glu Glu Gln Arg Asn Ala Lys
            20                  25                  30

Ile Lys Ser Ile Arg Asp Asp Ile Asp Ala Ser Asp
        35                  40

<210> SEQ ID NO 19
<211> LENGTH: 538
<212> TYPE: DNA
<213> ORGANISM: Artificial Sequence
```

<220> FEATURE:
<223> OTHER INFORMATION: Description of Artificial Sequence: Synthetic 538bp fragment sequence containing the HI loop

<400> SEQUENCE: 19

```
ggtaccaata tctggaacag ttcaaagtgc tcatcttatt ataagatttg acgaaaatgg     60
agtgctacta aacaattcct tcctggaccc agaatattgg aactttagaa atggagatct    120
tactgaaggc acagcctata caaacgctgt tggatttatg cctaacctat cagcttatcc    180
aaaatctcac ggtaaaactg ccaaaagtaa cattgtcagt caagtttact taaacggaga    240
caaaactaaa cctgtaacac taaccattac actaaacggt acacaggaaa ccggtctcat    300
caagtttaac atgcagcagc agcgccgctt ttacgaggcc ttgcacgacc ccaacctgaa    360
cgaggagcag cgcaacgcca agattaagag cattcgcgac gacatagatg ctagcgacac    420
aactccaagt gcatactcta tgtcattttc atgggactgg tctggccaca actacattaa    480
tgaaatattt gccacctcga gttacacttt ttcatacatt gcccaagaat aaggatcc      538
```

<210> SEQ ID NO 20
<211> LENGTH: 176
<212> TYPE: PRT
<213> ORGANISM: Artificial Sequence
<220> FEATURE:
<223> OTHER INFORMATION: Description of Artificial Sequence: Synthetic polypeptide sequence encoded by the 538bp fragment sequence

<400> SEQUENCE: 20

```
Val Pro Ile Ser Gly Thr Val Gln Ser Ala His Leu Ile Ile Arg Phe
1               5                   10                  15

Asp Glu Asn Gly Val Leu Leu Asn Asn Ser Phe Leu Asp Pro Glu Tyr
            20                  25                  30

Trp Asn Phe Arg Asn Gly Asp Leu Thr Glu Gly Thr Ala Tyr Thr Asn
        35                  40                  45

Ala Val Gly Phe Met Pro Asn Leu Ser Ala Tyr Pro Lys Ser His Gly
    50                  55                  60

Lys Thr Ala Lys Ser Asn Ile Val Ser Gln Val Tyr Leu Asn Gly Asp
65                  70                  75                  80

Lys Thr Lys Pro Val Thr Leu Thr Ile Thr Leu Asn Gly Thr Gln Glu
                85                  90                  95

Thr Gly Leu Ile Lys Phe Asn Met Gln Gln Gln Arg Arg Phe Tyr Glu
            100                 105                 110

Ala Leu His Asp Pro Asn Leu Asn Glu Glu Gln Arg Asn Ala Lys Ile
        115                 120                 125

Lys Ser Ile Arg Asp Asp Ile Asp Ala Ser Asp Thr Thr Pro Ser Ala
    130                 135                 140

Tyr Ser Met Ser Phe Ser Trp Asp Trp Ser Gly His Asn Tyr Ile Asn
145                 150                 155                 160

Glu Ile Phe Ala Thr Ser Ser Tyr Thr Phe Ser Tyr Ile Ala Gln Glu
                165                 170                 175
```

<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: Synthetic Z33 amino acid sequence

<400> SEQUENCE: 21

Phe Asn Met Gln Gln Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
attaccgaag aaatggccgc                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cccatttaac acgccatgca                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cggctgctgt tgcttttttg                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtatcttcat cgctagagcc                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcgtttctca gcagctgttg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
catctgaact caaagcgtgg                                          20

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcacagacag aatccctgct acc                                      23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggggtggaat gtgtcttggt ctc                                      23

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Gly Thr Gln Glu Thr Gly Leu Ile Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Asp Ala Ser Asp Thr Thr Pro Ser Ala
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Asp Cys Arg Gly Asp Cys Phe Cys
1               5

<210> SEQ ID NO 33
<211> LENGTH: 53
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 33

Asn Gly Thr Gln Glu Thr Gly Leu Ile Lys Phe Asn Met Gln Gln Gln
1               5                   10                  15

Arg Arg Phe Tyr Glu Ala Leu His Asp Pro Asn Leu Asn Glu Glu Gln
            20                  25                  30

Arg Asn Ala Lys Ile Lys Ser Ile Arg Asp Asp Ile Asp Ala Ser Asp
        35                  40                  45

Thr Thr Pro Ser Ala
    50

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gccgcagatc tatttaaatc gattgtcgac                                    30

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgccgcggag actgt                                                    15

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atttaaatcg atattaccct gttatcccta atcgattgtc gac                     43

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ala Tyr Thr
1